(12) United States Patent
Soane et al.

(10) Patent No.: US 11,918,694 B2
(45) Date of Patent: Mar. 5, 2024

(54) ORALLY INGESTIBLE DELIVERY SYSTEM

(71) Applicant: Soane Pharma LLC, Riviera Beach, FL (US)

(72) Inventors: David S. Soane, Palm Beach, FL (US); Allison H. Greene, Hillsboro Beach, FL (US); Alexander V. Soane, Palm Beach, FL (US)

(73) Assignee: Soane Pharma LLC, Riviera Beach, FL (US)

( * ) Notice: Subject to any disclaimer, the term of this patent is extended or adjusted under 35 U.S.C. 154(b) by 199 days.

(21) Appl. No.: 17/075,030

(22) Filed: Oct. 20, 2020

(65) Prior Publication Data

US 2021/0113476 A1   Apr. 22, 2021

Related U.S. Application Data

(60) Provisional application No. 63/088,070, filed on Oct. 6, 2020, provisional application No. 63/058,231, filed
(Continued)

(51) Int. Cl.
*A61K 9/48* (2006.01)
*A61K 9/00* (2006.01)
(Continued)

(52) U.S. Cl.
CPC .......... *A61K 9/4816* (2013.01); *A61K 9/0053* (2013.01); *A61K 9/4808* (2013.01);
(Continued)

(58) Field of Classification Search
CPC .. A61K 9/4816; A61K 9/0053; A61K 9/4808; A61K 35/12; A61K 36/00;
(Continued)

(56) References Cited

U.S. PATENT DOCUMENTS

| | | |
|---|---|---|
| 2009/0214600 A1 | 8/2009 | Debrouse |
| 2011/0182954 A1 | 7/2011 | Takahashi et al. |
| 2018/0221286 A1 | 8/2018 | Kabadi et al. |

FOREIGN PATENT DOCUMENTS

| | | | | |
|---|---|---|---|---|
| EP | 2832352 A1 | 2/2015 | | |
| WO | 2014013006 A1 | 1/2014 | | |
| WO | WO-2014013006 A1 | * | 1/2014 | ........... A61K 31/192 |

OTHER PUBLICATIONS

Ichikawa, Masaki, Sumio Watanabe, and Yasuo Miyake. "A new multiple-unit oral floating dosage system. I: Preparation and in vitro evaluation of floating and sustained-release characteristics." Journal of pharmaceutical sciences 80.11 (1991): 1062-1066. (Year: 1991).*

(Continued)

*Primary Examiner* — Lora E Barnhart Driscoll
*Assistant Examiner* — Candice Lee Swift
(74) *Attorney, Agent, or Firm* — Elmore Patent Law Group, P.C.; Mahreen Chaudhry Hoda; Carolyn S. Elmore

(57) ABSTRACT

The invention includes an orally ingestible delivery system for releasing a therapeutic agent within an intestine of a mammal, where the system includes the therapeutic agent and a differentially permeable capsule system containing the therapeutic agent within a therapeutic agent compartment, with the differentially permeable capsule system dimensionally adapted for oral ingestion and for passage into a stomach of the mammal and thence into the intestine, wherein the differentially permeable capsule system comprises an acid-resistant shell and a dispersible acid barrier, wherein the dispersible acid barrier forms while the orally-ingestible delivery system is in the stomach; and wherein the dispersible acid barrier is dispersed in the intestine, thereby permitting enzymes in the intestine to reach the therapeutic agent compartment. The invention also includes methods of manufacturing the system and methods for its use.

16 Claims, 17 Drawing Sheets

Related U.S. Application Data on Jul. 29, 2020, provisional application No. 63/010,132, filed on Apr. 15, 2020, provisional application No. 62/981,651, filed on Feb. 26, 2020, provisional application No. 62/950,527, filed on Dec. 19, 2019, provisional application No. 62/923,783, filed on Oct. 21, 2019.

(51) Int. Cl.
*A61K 35/12* (2015.01)
*A61K 36/00* (2006.01)
*A61K 38/00* (2006.01)

(52) U.S. Cl.
CPC .............. *A61K 35/12* (2013.01); *A61K 36/00* (2013.01); *A61K 38/00* (2013.01)

(58) Field of Classification Search
CPC .... A61K 38/00; A61K 9/0007; A61K 9/2081; A61K 9/4866; A61K 9/485; A61K 9/4858
See application file for complete search history.

(56) References Cited

OTHER PUBLICATIONS

Rouge, Nathalie, et al. "Buoyancy and drug release patterns of floating minitablets containing piretanide and atenolol as model drugs." Pharmaceutical development and technology 3.1 (1998): 73-84. (Year: 1998).*
Choi, B. Y., et al. "Preparation of alginate beads for floating drug delivery system: effects of $CO_2$ gas-forming agents." International journal of pharmaceutics 239.1-2 (2002): 81-91. (Year: 2002).*
"Gas in the Digestive Tract", Wake Gastroenterology. Retrieved on May 17, 2023, online at https://wakegastro.com/patient-info/patient-education/gas-in-the-digestive-tract7 pgs.
"Intestinal Gas", Retrieved on May 17, 2023, online at https://www.britannica.com/science/intestinal-gas5 pgs.
Garg, V. et al., "Antacids revisited: review on contemporary facts and relevance for self-management", J. Int. Med. Res., 50(3), doi: 10.1177/03000605221086457., Mar. 2022, 1-22.
Le, J. "Drug Absorption", Merck Manual Professional Version. Retrieved on May 17, 2023, online at https://www.merckmanuals.com/professional/clinical-pharmacology/pharmacokinetics/drug-absorption. Modified Sep. 2022, 5 pgs.
Nokhodchi, A. et al., "The Role of Oral Controlled Release Matrix Tablets in Drug Delivery Systems", BioImpacts, 2(4), doi: 10.5681/bi.2012.027, 2012, 175-187.

* cited by examiner

ORALLY INGESTIBLE DELIVERY SYSTEM

RELATED APPLICATIONS

This application claims the benefit of U.S. Provisional Application Ser. No. 62/923,783 filed Oct. 21, 2019, U.S. Provisional Application Ser. No. 62/950,527 filed Dec. 19, 2019, U.S. Provisional Application Ser. No. 62/981,651 filed Feb. 26, 2020, U.S. Provisional Application No. 63/010,132 filed Apr. 15, 2020, U.S. Provisional Application Ser. No. 63/058,231 filed Jul. 29, 2020, and U.S. Provisional Application No. 63/088,070 filed Oct. 6, 2020. The entire contents of the above applications are incorporated by reference herein.

FIELD OF THE APPLICATION

This application relates to orally ingestible delivery systems for drugs, biologics, and other therapeutic agents.

BACKGROUND

Therapeutic agents for treating a medical condition are formulated to optimize the delivery and uptake of the agent when it is administered to a patient. As used herein, "therapeutic agent" is any substance, material, device, organism, or portion thereof, that is delivered to a person or animal to effect a therapeutic intervention. For avoidance of doubt, a therapeutic intervention can include diagnostic interventions and surveillance interventions (i.e., interventions to diagnose and thereby prevent an anticipated disorder, and interventions to gather data about states of wellness or disease, in order to facilitate prevention of an anticipated disorder).

Pharmacokinetics is the branch of pharmacology that deals with the movement of a pharmaceutical or biological therapeutic agent into, through, and out of the body: its absorption, distribution, metabolism, and excretion. Bioavailability is a subcategory of absorption, referring to the amount of the administered therapeutic agent that reaches systemic circulation. When the agent is administered intravenously, by definition, the entire dose enters the systemic circulation and it has 100% bioavailability. Agents administered by other routes besides intravenously (i.e., orally, intramuscularly, subcutaneously, transdermally, sublingually, rectally, etc.) typically have less absorption and therefore less bioavailability (i.e., less of the administered dose reaches the circulation and thus less is distributed to the target organs and cells). Bioavailability is measured by a pharmacokinetic study that measures the plasma concentration of the agent vs. time; the dose-corrected area under the curve for this plasma concentration vs. time curve represents the bioavailability. The bioavailability of an agent delivered via a non-intravenous route compared to its bioavailability when administered intravenously is termed its absolute bioavailability.

Routes of delivery for a therapeutic agent can involve the gastrointestinal tract (termed "enteral" or "enteric" administration) or other pathways that do not involve the gastrointestinal tract (termed "parenteral" administration). Intravenous administration is one parenteral delivery route, but there are others: examples include injections into body cavities, muscles, under the skin, into the skin, diffusion through mucous membranes or through the skin, and inhalation. Parenteral administration has certain well-recognized advantages. Most importantly, it allows the therapeutic agent to reach the systemic circulation quickly, without having to navigate the digestive tract, where its effective uptake can be unpredictable due to altered blood flow, low gastrointestinal motility, poor absorption, or effects of first pass metabolism. For these reasons, parenteral mechanisms typically result in greater absolute bioavailability. Moreover, therapeutic agents comprising proteins, peptides, and living organisms like viruses and cells have to date required parenteral administration, because they are susceptible to digestion in the stomach, which would render them ineffective.

While the bioavailability advantages of parenteral administration are important in intensive care and emergency situations, these routes have clear drawbacks for more routine or chronic treatments. Parenteral delivery commonly requires invasive interventions such as needle punctures and infusions that are carried out by skilled personnel using sterile techniques; under other circumstances, parenteral delivery relies on complex mechanisms such as specialized aerosols or pumps. These auxiliary requirements make parenteral delivery costly, inconvenient, and/or unpleasant for patients, especially when the treatment needs to be administered frequently. The need for invasive or technically complicated interventions makes parenteral delivery especially undesirable for certain patient populations, such as pediatric patients and patients in underserved areas that do not have access to the medical facilities for more complex delivery systems.

Despite these drawbacks, a large number of conditions requiring repeated or widespread treatment, for example chronic conditions, or population-based conditions such as disease prophylaxis via vaccination, are currently treated parenterally, in many cases because the treatment agent is not compatible with enteric—specifically oral—administration. Other conditions not treatable by oral administration are suitable for non-oral routes of enteric administration, for example via rectal delivery (enemas, suppositories, and the like). Examples of rectal delivery include diseases of the colon such as ulcerative colitis, where the active ingredient can act directly on the colon itself, and disorders treated by bacteriotherapy (for example, fecal transplant), where living organism are introduced into the colon to repopulate it with healthy bacteria. For many of these conditions treated parenterally or rectally, oral delivery would be preferable because it is convenient, familiar, and generally well-tolerated by the patient.

During oral administration, the therapeutic agent passes from the mouth through the esophagus into the stomach, then passing from the stomach into the duodenum and thereafter into the rest of the small intestine. The delivery vehicle for an oral agent needs to have sufficient mechanical integrity to survive passage from the mouth into the stomach, but this involves fairly standard pharmaceutical techniques. The stomach presents more daunting conditions for a drug or biologic. Cells in the stomach mucosa produce hydrochloric acid, leading to an acidic environment in the stomach (pH about 1.0). Furthermore, stomach cells secrete pepsinogen, a proenzyme for pepsin, an enzyme that breaks down proteins. The acid in the stomach hydrolyzes proteins, and further converts the proenzyme pepsinogen into its active form pepsin; pepsin digests proteins in the stomach, breaking them down into peptides that are further digested in the small intestine and then absorbed. Small molecules delivered orally are susceptible to hydrolysis by stomach acid. Proteins and peptides delivered orally are not only hydrolyzed by stomach acid, but they are also digested by pepsin. These conditions in the stomach prevent or impair the use of the oral delivery route for many therapeutic agents.

As pharmaceuticals and biopharmaceuticals are developed to treat chronic or population-specific conditions, it would be desirable to avoid the drawbacks associated with their mode of delivery. A wide range of disorders, from insulin-dependent diabetes to chronic inflammatory diseases can be treated with pharmaceutical and biopharmaceutical agents that are administered parenterally. Other disorders require widespread treatment measures across a large population, such as vaccines, or require access to populations such as children who find parenteral administration hard to tolerate. Certain disorders currently can only be treated with agents delivered rectally. Even though there are costs and drawbacks to these modes of delivery, they remain the only options for these agents at present, because they cannot survive passage through the stomach.

There remains a need in the art therefore for improved delivery vehicles for oral administration of therapeutic agents that do not tolerate exposure to stomach conditions, including biopharmaceuticals, living organisms, microdevices, and small molecules. There also exists a need for an alternative to rectal delivery to spare patients the discomfort and inconvenience that this route of administration involves. These improved delivery mechanisms would be particularly advantageous in chronic conditions requiring frequent dosing, or in specialized populations, because of increased patient convenience and acceptance, and decreased complexity and health care cost.

There remains a further need in the art therefore for improved delivery vehicles for oral administration of therapeutic agents that do not tolerate exposure to stomach conditions, including biopharmaceuticals, living organisms, microdevices, and small molecules. There also exists a need for an alternative to rectal delivery to spare patients the discomfort and inconvenience that this route of administration involves. These improved delivery mechanisms would be particularly advantageous in chronic conditions requiring frequent dosing, or in specialized populations, because of increased patient convenience and acceptance and decreased complexity and health care cost. Advantageously, the improved delivery vehicles can be optimized for easy ingestion, for example in palatable and easy-to-eat dosage forms or milieus. Pharmaceutical products in edible forms are well-known in the art, for example, vitamins as "gummies," cough drops as lozenges, calcium and Vitamin D in chocolates and caramels, and the like. Improving the consistency and flavor of the delivery vehicle can improve its overall acceptance by patients, especially for populations that are reluctant to or unable to swallow pills. It would be further advantageous to provide the delivery vehicles in a food item that facilitates ingestion. For example, a delivery vehicle that could be added to liquid, gel, or semi-solid media such as soups, drinks, milk shakes, ice cream, yogurt, jellies, and the like, would be appealing to consumers and easy to swallow. Such improved delivery mechanisms would be particularly desirable for those conditions that require frequent dosing, or in specialized populations such as children or patients with dysphagias, because of increased patient convenience and acceptance and decreased complexity and health care cost.

SUMMARY OF THE INVENTION

In certain aspects, the invention is directed to an orally ingestible delivery system for releasing a therapeutic agent within an intestine of a mammal, comprising: the therapeutic agent and a differentially permeable capsule system containing the therapeutic agent within a therapeutic agent compartment, wherein the differentially permeable capsule system is dimensionally adapted for oral ingestion and for passage into a stomach of the mammal and thence into the intestine; wherein the differentially permeable capsule system comprises an acid-resistant shell and a dispersible acid barrier; wherein the dispersible acid barrier is deployed in a locus selected from the group consisting of an external aspect of the acid-resistant shell, an internal aspect within the acid-resistant shell, and an inferior region below the acid-resistant shell, said dispersible acid barrier inhibiting contact between the acid-resistant shell and the gastric juice in the stomach; wherein the dispersible acid barrier forms while the orally-ingestible delivery system is in the stomach; and wherein the dispersible acid barrier is dispersed in the intestine, thereby permitting enzymes in the intestine to reach the therapeutic agent compartment.

In further aspects, the invention is directed to the orally ingestible delivery system, wherein the acid-resistant shell is an acid resistant protease digestible membrane. In yet additional aspects, the acid-resistant shell comprises or consists essentially of a waxy substance. In further aspects, the acid-resistant shell comprises fibers, optionally wherein the fibers are digestible or hydrolyzable.

In yet additional aspects, the dispersible acid barrier is a gas barrier, for example, the gas barrier can be formed by the reaction of stomach acid with gas-producing substances, wherein the gas-producing substances are deployed in at least one of the external aspect of the acid-resistant shell, the internal aspect within the acid-resistant shell, and the inferior region below the acid-resistant shell; optionally, the acid-resistant shell is perforated with a system of pores containing deposits of the gas-producing substances. In certain aspects, the gas barrier comprises carbon dioxide. In yet additional embodiments, the gas barrier is dispersed by interaction of the carbon dioxide with bicarbonate in the intestine.

In further aspects, the acid-resistant shell comprises space-occupying fluids or space-occupying solids. The space-occupying fluid or space-occupying solid can, for example, be deployed within the system of pores. In certain aspects, the space-occupying fluid is a nonpolar liquid. In yet additional aspects, the space-occupying solid reacts with the gastric juice to produce a second space-occupying fluid comprising a liquid or a gas; for example, the space-occupying solid comprises solid bicarbonate, and the gas comprises carbon dioxide.

The invention also includes a method of delivering a therapeutic agent into an intestine of a mammal, comprising providing the orally ingestible delivery system described herein; administering the orally ingestible delivery system to the mammal by mouth; wherein the orally ingestible delivery system passes into the stomach, wherein the orally ingestible delivery system is exposed to stomach acid that interacts with it to form the dispersible acid barrier; and wherein the orally ingestible delivery system then passes into the intestine, wherein the dispersible acid barrier is dispersed by interaction with intestinal fluids, and whereby intestinal fluids penetrate the acid-resistant shell following dispersal of the dispersible acid barrier to release the therapeutic agent from the therapeutic agent compartment; thereby delivering the therapeutic agent to the intestine. In certain aspects, the intestinal fluids impair integrity of the acid-resistant shell, thereby facilitating release of the therapeutic agent from the therapeutic agent compartment. In certain additional aspects, the therapeutic agent is susceptible to degradation in the stomach. The therapeutic agent can be a protein or a peptide, or a living organism.

The invention also encompasses a method of delivering an effective amount of a therapeutic agent to a patient in need thereof, comprising: providing the orally ingestible delivery system as described herein, wherein the orally ingestible delivery system contains the effective amount of the therapeutic agent; administering the orally ingestible delivery system to the patient by mouth; wherein the orally ingestible delivery system passes into a stomach of the patient, wherein the orally ingestible delivery system is exposed to stomach acid that interacts with the orally ingestible delivery system to form the dispersible acid barrier; and wherein the orally ingestible delivery system then passes into the intestine of the patient, wherein the dispersible acid barrier is dispersed by interaction with intestinal fluids, and whereby intestinal fluids penetrate the acid-resistant shell following dispersal of the dispersible acid barrier to release the therapeutic agent from the therapeutic agent compartment, thereby delivering the effective amount of the therapeutic agent to the patient.

In certain aspects, the patient is undergoing treatment with the therapeutic agent for a condition selected from the group consisting of cancers, metabolic disorders, allergic disorders, hormonal disorders, dermatological disorders, cardiovascular disorders, respiratory disorders, hematological disorders, musculoskeletal disorders, inflammatory disorders, rheumatological disorders, autoimmune disorders, gastrointestinal disorders, urological disorders, sexual and reproductive disorders, neurological disorders, and genetic disorders.

The invention further encompasses an orally ingestible delivery system, comprising an acid-resistant shell surrounding a therapeutic agent compartment, and further comprising space-occupying fluids or space-occupying solids disposed in a locus selected from the group consisting of an external aspect of the acid-resistant shell, an internal aspect within the acid-resistant shell, and an inferior region below the acid-resistant shell, wherein the space-occupying fluids or space-occupying solids provide mechanical obstruction to the penetration of the acid-resistant shell by stomach acid. In certain aspects, the acid-resistant shell is perforated by a system of pores; optionally, wherein at least a portion of the space-occupying fluids or space-occupying solids resides within the system of pores. In additional aspects, the therapeutic agent compartment is dimensionally adapted for containing a therapeutic agent deliverable; for example, the therapeutic agent compartment is a void. In yet further aspects, the therapeutic agent compartment contains a therapeutic agent deliverable, and optionally, wherein the therapeutic agent deliverable comprises at least one therapeutic agent. In certain aspects, the space-occupying fluids or space-occupying solids are acid-reactive substances. For example, the acid-reactive substances can comprise gas-forming substances that produce or release gas upon contact with the hydrochloric acid in the stomach, and wherein the gas provides mechanical obstruction to the penetration of the acid-resistant shell by stomach acid. In certain aspects, the gas is carbon dioxide.

The invention also includes an orally ingestible delivery system, comprising: a digestible capsule system surrounding a therapeutic agent compartment, wherein the digestible capsule system comprises an acid-resistant shell and a dispersible acid barrier; wherein the dispersible acid barrier is disposed in a locus selected from the group consisting of an external aspect of the acid-resistant shell, an internal aspect within the acid-resistant shell, and an inferior region below the acid-resistant shell; wherein the dispersible acid barrier prevents at least one of acid and enzymes from reaching the therapeutic agent compartment to impair the integrity thereof; wherein the dispersible acid barrier, once formed, is dispersed by exposure to a component of duodenal fluid; and wherein the therapeutic agent compartment contains a therapeutic agent deliverable. In certain aspects, the dispersible acid barrier comprises a space-occupying solid or space-occupying fluid. In certain aspects, wherein the space-occupying fluid is a gas. In yet further aspects, the space-occupying solid or space-occupying fluid comprises an acid-reactive substance; optionally, wherein the space-occupying solid or space-occupying fluid produces a second space-occupying material upon contact with acid in the stomach, wherein the second space-occupying material forms in whole or in part the dispersible acid barrier; and/or further optionally, wherein the second space-occupying material is a gas. In yet further aspects, the integrity of the therapeutic agent compartment is impaired by enzymatic activity following dispersal of the dispersible acid barrier. In additional aspects, the component of duodenal fluid is bicarbonate or bile salts.

The invention also encompasses a method of delivering a therapeutic agent into an intestine of a mammal, comprising: providing the orally ingestible delivery system described above; administering the orally ingestible delivery system to the mammal by mouth; exposing the orally ingestible delivery system to an acid before, during, or after the step of administering the orally ingestible delivery system by mouth, wherein the acid interacts with acid-reactive space-occupying fluids or space-occupying solids to form a second space-occupying fluid that forms the dispersible acid barrier; permitting the orally ingestible delivery system to pass through a stomach of the mammal into an intestine; and contacting the orally ingestible delivery system with duodenal fluid, wherein the component of the duodenal fluid disperses the dispersible acid barrier, thereby exposing the orally ingestible delivery system to enzymatic activity within the intestine, and wherein the enzymatic activity impairs integrity of the therapeutic agent compartment, thereby releasing the therapeutic agent from the therapeutic agent compartment and delivering it into the intestine. In certain aspects, the orally ingestible delivery system is exposed to the acid after the step of administering the orally ingestible delivery system by mouth, and the acid is a gastric acid. The invention also includes a method of manufacturing a differentially permeable capsule system, comprising providing an acid-resistant shell; and affixing one or more deposits of an acid-reactive substances to the acid-resistant shell or embedding one or more deposits of the acid-reactive substance within the acid-resistant shell, wherein the deposits are disposed in a locus selected from the group consisting of an external aspect of the acid-resistant shell, an internal aspect within the acid-resistant shell, and an inferior region below the acid-resistant shell. The acid-resistant shell can contain fibers or can comprise a waxy substance. In certain aspects, the acid-resistant shell is perforated by a system of pores; optionally, wherein the deposits are at least partially deployed within the system of pores. In certain additional aspects, the acid-reactive substances comprises gas-producing substances; optionally, wherein the gas-producing substances form carbon dioxide upon exposure to hydrochloric acid. In yet further aspects, the method further comprises the step of forming the acid-resistant shell to enclose a therapeutic agent compartment, wherein the therapeutic agent compartment is dimensionally adapted to contain a therapeutic agent deliverable. The method can further comprise including a therapeutic agent deliverable in the therapeutic agent compartment.

The invention additionally includes an orally ingestible delivery system for releasing a therapeutic agent within an intestine of a mammal, comprising the therapeutic agent and a digestible capsule system containing the therapeutic agent within a therapeutic agent compartment, the digestible capsule system being dimensionally adapted for oral ingestion, and for passage into a stomach of the mammal and thence into the intestine, and the digestible capsule system comprising an acid-resistant protease-digestible membrane and a dispersible acid barrier, wherein the dispersible acid barrier is deployed in a locus selected from the group consisting of an exterior surface of the acid-resistant protease-digestible membrane and an internal region within the acid-resistant protease-digestible membrane, said dispersible acid barrier inhibiting contact with gastric juice in a stomach, wherein the dispersible acid barrier forms in the stomach and is dispersed in the intestine to expose the acid-resistant protease-digestible membrane to enzyme activity in the intestine, and wherein the acid-resistant protease-digestible membrane exposed to enzyme activity in the intestine is digested in whole or in part by the enzyme activity, thereby releasing the therapeutic agent within the intestine.

In certain aspects, the acid-resistant protease-digestible membrane comprises an inner protease-digestible layer and an outer acid-resistant layer. In additional aspects, the dispersible acid barrier deployed on the exterior surface of the acid-resistant protease-digestible membrane or within the internal region of the acid-resistant protease-digestible membrane is a gas barrier. The gas barrier can be, for example, formed by the reaction of stomach acid with gas-producing substances, wherein the gas-producing substances are contained within the internal region of the acid-resistant protease-digestible membrane. Optionally, the acid-resistant protease-digestible membrane is perforated with a system of pores containing deposits of a gas-producing substance, wherein a reaction of stomach acid with the gas-producing substance produces the gas barrier. In additional aspects, the gas barrier comprises carbon dioxide. In yet additional aspects, the gas barrier is dispersed by interaction of the carbon dioxide with bicarbonate in the intestine. In yet further aspects, the dispersible acid barrier deployed on the exterior surface of the acid-resistant protease-digestible membrane or within the internal region of the acid-resistant protease-digestible membrane comprises space-occupying fluids or space-occupying solids, for example a nonpolar liquid. In certain aspects, the space-occupying fluid or space-occupying solid is deployed within the system of pores and/or the space-occupying solid reacts with the gastric juice to produce a space-occupying fluid comprising a liquid or a gas. In specific aspects, the space-occupying solid comprises solid bicarbonate, and the gas is carbon dioxide.

The invention encompasses a method of delivering a therapeutic agent into an intestine of a mammal, comprising providing the orally ingestible delivery system described herein; administering the orally ingestible delivery system to the mammal by mouth; permitting passage of the orally ingestible delivery system into the stomach, wherein the orally ingestible delivery system is exposed to stomach acid that interacts with it to form the dispersible acid barrier within and/or upon the orally ingestible delivery system; and permitting further passage of the orally ingestible delivery system into the intestine, wherein the dispersible acid barrier is dispersed by interaction with secretions in the intestine, and whereby enzyme activity in the intestine contacts the acid-resistant protease-digestible membrane following dispersal of the dispersible acid barrier, thereby impairing the integrity of the acid-resistant protease-digestible membrane and permitting egress of the therapeutic agent contained therein; thereby delivering the therapeutic agent to the intestine. In certain aspects, the therapeutic agent, for example, a protein or a peptide, is susceptible to degradation in the stomach. In additional aspects, the therapeutic agent is a living organism.

In yet further aspects, the invention is directed to a method of delivering an effective amount of a therapeutic agent to a patient in need thereof, comprising: providing the orally ingestible delivery system described herein, wherein the orally ingestible delivery system contains the effective amount of the therapeutic agent; administering the orally ingestible delivery system to the patient by mouth; permitting passage of the orally ingestible delivery system into a stomach of the patient, wherein the orally ingestible delivery system is exposed to stomach acid that interacts with the orally ingestible delivery system to form the dispersible acid barrier; and permitting further passage of the orally ingestible delivery system into an intestine of the patient, wherein the dispersible acid barrier is dispersed by interaction with secretions in the intestine, wherein enzyme activity in the intestine contacts the acid-resistant protease-digestible membrane following dispersal of the dispersible acid barrier, thereby impairing the integrity of the acid-resistant protease-digestible membrane and permitting egress of the therapeutic agent from the therapeutic agent compartment; thereby delivering the effective amount of the therapeutic agent to the patient. In certain aspects, the patient is undergoing treatment with the therapeutic agent for a condition selected from the group consisting of cancers, metabolic disorders, allergic disorders, hormonal disorders, dermatological disorders, cardiovascular disorders, respiratory disorders, hematological disorders, musculoskeletal disorders, inflammatory disorders, rheumatological disorders, autoimmune disorders, gastrointestinal disorders, urological disorders, sexual and reproductive disorders, neurological disorders, and genetic disorders.

The invention additionally encompasses an orally ingestible delivery system, comprising a digestible capsule system surrounding a therapeutic agent compartment, wherein the therapeutic agent compartment is dimensionally adapted for containing a therapeutic agent deliverable, the digestible capsule system comprising an acid-resistant protease digestible membrane within which are disposed space-occupying fluids or solids. In certain aspects, the therapeutic agent compartment is a void. In yet additional aspects, the therapeutic agent compartment contains a therapeutic agent deliverable, for example, the therapeutic agent deliverable comprises at least one therapeutic agent. In yet further aspects, the acid-resistant protease digestible membrane is perforated by a system of pores. In certain embodiments, the acid-resistant protease digestible membrane comprises an inner protease-digestible layer and an outer acid-resistant layer, and wherein the system of pores is disposed in whole or in part within the outer acid-resistant layer. In additional aspects, at least a portion of the space-occupying fluids or solids resides within the system of pores.

The invention additionally encompasses an orally ingestible delivery system, comprising: a digestible capsule system surrounding a therapeutic agent compartment, wherein the digestible capsule system comprises an acid-resistant protease digestible membrane and a dispersible acid barrier, wherein the dispersible acid barrier is formed on or within at least one of an external surface of the acid-resistant protease digestible membrane and an internal system of pores contained within the acid-resistant protease digestible membrane; wherein the dispersible acid barrier prevents at least one of acid and enzymes from reaching the therapeutic agent compartment to impair the integrity thereof; wherein the dispersible acid barrier, once formed, is dispersed by exposure to a component of duodenal fluid; and wherein the therapeutic agent compartment contains a therapeutic agent deliverable. In certain aspects, the dispersible acid barrier comprises a space-occupying solid or fluid. The space-occupying solid or fluid can, for example, product a second space-occupying material upon contact with acid in the stomach, wherein the second space-occupying material forms in whole or in part the dispersible acid barrier. In yet additional aspects, the integrity of the therapeutic agent compartment is impaired by enzymatic activity following dispersal of the dispersible acid barrier. In further embodiments, the component of duodenal fluid is bicarbonate or bile salts.

The invention also encompasses a method of delivering a therapeutic agent into an intestine of a mammal, comprising: providing the orally ingestible delivery system described above; administering the orally ingestible delivery system to the mammal by mouth; exposing the orally ingestible delivery system to an acid before, during, or after the step of administering the orally ingestible delivery system by mouth, wherein the acid interacts with acid-reactive substances deployed within the acid-resistant protease-digestible membrane, thereby producing space-occupying fluids that form the dispersible acid barrier; permitting the orally ingestible delivery system to pass through a stomach of the mammal into the duodenum; and contacting the orally ingestible delivery system with duodenal fluid, wherein the component of the duodenal fluid disperses the dispersible acid barrier, thereby exposing the orally ingestible delivery system to enzymatic activity within the intestine, and wherein the enzymatic activity impairs the integrity of the therapeutic agent compartment, thereby releasing the therapeutic agent from the therapeutic agent compartment and delivering it into the intestine. In certain aspects, the orally ingestible delivery system is exposed to the acid after the step of administering the orally ingestible delivery system by mouth, and the acid is a gastric acid.

Disclosed herein, in embodiments, is an orally ingestible delivery system for releasing a therapeutic agent within an intestine of a mammal, comprising the therapeutic agent and a digestible capsule system containing the therapeutic agent within a therapeutic agent chamber, the digestible capsule system being dimensionally adapted for oral digestion and for passage into a stomach of the mammal and thence into the intestine, and the digestible capsule system comprising an acid-resistant protease-digestible membrane and a dispersible gas barrier, wherein the dispersible gas barrier is disposed in whole or in part on an exterior surface of the acid-resistant protease-digestible membrane, said dispersible gas barrier inhibiting contact with gastric juice in a stomach, wherein the dispersible gas barrier forms in the stomach and is dispersed in the intestine to expose the acid-resistant protease-digestible membrane to enzyme activity in the intestine, and wherein the acid-resistant protease-digestible membrane exposed to enzyme activity in the intestine is digested in whole or in part by the enzyme activity, thereby releasing the therapeutic agent within the intestine. In embodiments, the acid-resistant protease-digestible membrane comprises an inner protease-digestible layer and an outer acid-resistant layer. In embodiments, the acid-resistant protease-digestible membrane is perforated with a system of pores containing deposits of a gas-producing substance, wherein a reaction of stomach acid with the gas-producing substance produces a gas that accumulates to form the dispersible gas barrier. In embodiments, the gas comprises carbon dioxide, and the dispersible gas barrier is dispersed by interaction of the carbon dioxide with bicarbonate in the intestine.

Further disclosed herein, in embodiments, are methods of delivering a therapeutic agent into an intestine of a mammal, comprising providing the orally ingestible delivery system comprising an acid-resistant protease-digestible membrane and a therapeutic agent chamber containing the therapeutic agent, administering the orally ingestible delivery system to the mammal by mouth, permitting passage of the orally ingestible delivery system into the stomach, wherein the orally ingestible delivery system is exposed to stomach acid that interacts with it to form a dispersible gas barrier within and/or upon the orally ingestible delivery system, and permitting further passage of the orally ingestible delivery system into the intestine, wherein the dispersible gas barrier is dispersed by interaction with bicarbonate secretions in the intestine, and wherein enzyme activity in the intestine contacts the acid-resistant protease-digestible membrane to impair its integrity and the integrity of the therapeutic agent chamber, thereby permitting egress of the therapeutic agent contained therein and delivering the therapeutic agent to the intestine. In embodiments, the therapeutic agent is susceptible to degradation in the stomach. In embodiments, the therapeutic agent is a protein or a peptide or a living organism. Also disclosed herein, in embodiments, are methods of delivering an effective amount of a therapeutic agent to a patient in need thereof, comprising providing the orally ingestible delivery system comprising an acid-resistant protease-digestible membrane and a therapeutic agent chamber containing the effective amount of the therapeutic agent, administering the orally ingestible delivery system to the patient by mouth, permitting passage of the orally ingestible delivery system into a stomach of the patient, wherein the orally ingestible delivery system is exposed to stomach acid that interacts with the orally ingestible delivery system to form a dispersible gas barrier; and permitting further passage of the orally ingestible delivery system into an intestine of the patient, wherein the dispersible gas barrier is dispersed by interaction with bicarbonate secretions in the intestine, wherein enzyme activity in the intestine interacts with the acid-resistant protease-digestible membrane to impair its integrity, thereby releasing the therapeutic agent from the therapeutic agent chamber and delivering the effective amount of the therapeutic agent to the patient. In embodiments, the patient is undergoing treatment with the therapeutic agent for a condition selected from the group consisting of cancers, metabolic disorders, allergic disorders, hormonal disorders, dermatological disorders, cardiovascular disorders, respiratory disorders, hematological disorders, musculoskeletal disorders, inflammatory disorders, rheumatological disorders, autoimmune disorders, disorders due to hormone imbalances, gastrointestinal disorders, urological disorders, sexual and reproductive disorders, neurological disorders, and genetic disorders.

Also disclosed herein, in embodiments, is an orally ingestible delivery system, comprising a digestible capsule system surrounding a therapeutic agent chamber, wherein the therapeutic agent chamber is dimensionally adapted for containing a therapeutic agent deliverable, and wherein the digestible capsule system comprises an acid-resistant protease digestible membrane within which are disposed gas-producing substances. In embodiments, the therapeutic agent chamber is a void, and in embodiments, the therapeutic agent chamber contains a therapeutic agent deliverable, which an comprise at least one therapeutic agent. In embodiments, the acid-resistant protease digestible membrane is perforated by a system of pores. In embodiments, the acid-resistant protease digestible membrane comprises two layers, an inner protease-digestible layer and an outer acid-resistant layer, and the system of pores is disposed within the outer acid-resistant layer. In embodiments, at least a portion of the gas-producing substances resides within the system of pores.

Further disclosed herein, in embodiments, is an orally ingestible delivery system, comprising a digestible capsule system surrounding a therapeutic agent chamber, wherein the therapeutic agent chamber contains a therapeutic agent deliverable; an acid-resistant protease digestible membrane; and a dispersible gas barrier, wherein the dispersible gas barrier is formed on or within at least one of an external surface of the acid-resistant protease digestible membrane and an internal system of pores contained within the acid-resistant protease digestible membrane, wherein the dispersible gas barrier prevents at least one of acid and enzymes from reaching the therapeutic agent chamber to impair the integrity thereof. In embodiments, the dispersible gas barrier is formed by contact with an acid, and the dispersible gas barrier, once formed, is dispersible by exposure to a neutral or basic environment. In embodiments, the integrity of the therapeutic acid chamber is impaired by enzymatic activity following dispersal of the dispersible gas barrier.

Also disclosed herein, in embodiments, are methods of delivering a therapeutic agent into an intestine of a mammal, comprising providing the orally ingestible delivery system as described above; administering the orally ingestible delivery system to the mammal by mouth; exposing the orally ingestible delivery system to an acid before, during, or after the step of administering the orally ingestible delivery system by mouth, wherein the acid interacts with gas-producing substances incorporated in the orally ingestible delivery system and thereby produces the dispersible gas barrier; permitting the orally ingestible delivery system to pass through a stomach of the mammal into an intestine; and contacting the orally ingestible delivery system with neutral or basic secretions within the intestine, wherein the neutral or basic secretions within the intestine disperse the dispersible gas barrier, thereby exposing the orally ingestible delivery system to enzymatic activity within the intestine, and wherein the enzymatic activity impairs the integrity of the therapeutic agent chamber, thereby releasing the therapeutic agent from the therapeutic agent and delivering it into the intestine. In embodiments, the orally ingestible delivery system is exposed to the acid after the step of administering the orally ingestible delivery system by mouth, and the acid is a gastric acid.

DETAILED DESCRIPTION

Figure 1:
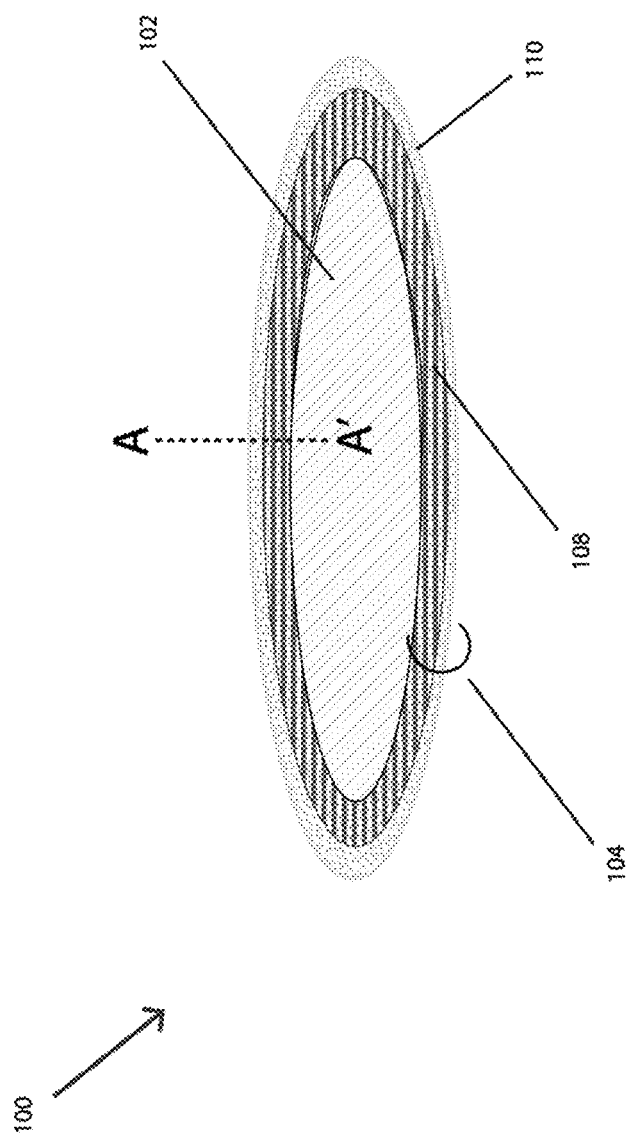
FIG. 1 depicts schematically an embodiment of an orally ingestible delivery system.

As used herein, the indefinite articles "a" or "an" are intended to mean "one or more" unless otherwise specified.

Disclosed herein, in embodiments, are orally ingestible delivery systems for releasing a therapeutic agent within the lumen of the gastrointestinal tract of a patient. As used herein, the term "gastrointestinal tract" includes, but is not limited to, the stomach, the small intestine with its three segments (duodenum, jejunum, ileum) and the large intestine, the small intestine and the large intestine collectively being termed the "intestinal tract." The orally ingestible delivery system disclosed herein is particularly adapted for delivering the therapeutic agent to target areas for absorption within the small or large intestine. In embodiments, the therapeutic agent is delivered within the small intestine; in other embodiments the therapeutic agent is delivered within the large intestine; yet other embodiments can combine points of delivery so that the therapeutic agent is delivered throughout the small intestine, throughout the large intestine or both.

A. Orally Ingestible Delivery Systems and Methods of Manufacture

1. Orally Ingestible Delivery System Generally: Passage into the Stomach

The delivery system disclosed herein is designed to retain designated degrees of integrity as it passes through the stomach. In embodiments, the delivery system disclosed herein remains substantially intact as it passes through the stomach, thereafter decomposing or being digested at some point distal to the stomach, or it remains substantially intact as it passes through the stomach, resisting the ingress of stomach fluids but becoming permeable to fluids in the intestinal tract.

This feature, whereby the delivery system has a preselected degree of resistance to fluid ingress in the stomach, and a different, preselected degree of resistance to fluid ingress in the intestine, is referred to herein as being "differentially permeable." In an embodiment, the orally ingestible delivery system (OIDS) comprises a differentially permeable capsule system that resists fluid ingress in the stomach, but is susceptible to fluid ingress in the intestine, so that the stomach fluid is inhibited from passing through the capsule system to access the therapeutic agent compartment, but the intestinal fluid is permitted to pass through the capsule system to access the therapeutic agent compartment. In such an embodiment, the contents of the therapeutic agent compartment are protected from exposure to stomach acid so that they pass relatively intact into the intestine, where the therapeutic agent compartment is reached by and penetrated by the intestinal fluid, so that the therapeutic agent is released within the intestinal tract.

As used herein, the term "digest" and related lexical units comprising this term refer to a destruction, decomposition, breakdown, processing, or loss of structural integrity brought about by exposure to enzymes, acid, or other physiological agents as they act upon an orally ingested material within the gastrointestinal tract. The term "digestion" as used herein refers solely to the mechanical and/or chemical breakdown of the orally ingested material, and does not refer to its subsequent absorption or excretion. In embodiments, the orally ingestible delivery system passes through the stomach without much or any digestion, and then releases the therapeutic agent in the duodenum or jejunum or ileum. In other embodiments, the orally ingestible delivery system passes through the stomach and portions of the small intestine without much or any digestion, and then releases the therapeutic agent in the colon.

In more detail, the orally ingestible delivery system is ingested by mouth, and then passes into the esophagus and thence into the stomach. In embodiments, the delivery system is designed to retain at least a portion of its integrity within the stomach, with any loss of integrity in the stomach or distal to the stomach being incorporated into the design. For example, an outer shell or coat surrounding the orally ingestible delivery system described below can be formulated to dissolve partially in the stomach. In other embodiments, the entire orally ingestible delivery system is designed to commence its decomposition or digestion within the stomach, optionally with the release of some or all of a therapeutic agent encased within the system or embedded within the walls of the system itself. As used herein, the term "differentially permeable capsule system" refers to the structures of the orally ingestible delivery system that have differential permeabilities in the stomach and in the intestinal tract. In an embodiment, the capsule is designed to undergo digestion in one or more locations of the gastrointestinal tract (for example, stomach and/or duodenum). In an embodiment, the differentially permeable capsule system passes through the stomach with minimal if any digestion, but is susceptible to digestion within the duodenum. Features and exemplary embodiments of a differentially permeable capsule system are described below in more detail and are illustrated by certain of the following Figures. For purposes of clarity, the term "differentially permeable capsule system" encompasses those "digestible capsule systems" or "selectively digestible capsule systems" described herein. One way in which a differentially permeable capsule system can impart different degrees of resistance to fluid ingress in the stomach vs in the intestine is by permitting different degrees of digestion of the capsular layer(s) in the stomach as compared to the intestine. Other ways for imparting differentially permeable properties to the capsule system can involve mechanisms for inhibiting fluid passage into and through the capsule while it is in the stomach, and permitting fluid passage into and through the capsule when it is in the intestine, where such mechanisms may substitute for or supplement the digestion of the capsule itself.

FIG. 1 shows in cross section an embodiment of an orally ingestible delivery system 100 following its ingestion and after a period of residence in the stomach. The orally ingestible delivery system 100 as shown comprises a differentially permeable (for example, digestible) capsule system 104 that encloses a therapeutic agent in a therapeutic agent compartment 102. The therapeutic agent compartment 102 can be formed as a discrete enclosure with its own walls, or it can be formed as one or more orally ingestible delivery systems within the differentially permeable capsule system 104 for containing the therapeutic agent, or in any other configuration suitable for the retention of the solid, liquid, or semisolid therapeutic agent within the orally ingestible delivery system 100.

While this Figure and subsequent Figures depict the therapeutic agent compartment 102 as a single compartment, it is understood that there can be one, two, or more therapeutic agent compartments 102 disposed within the orally ingestible delivery system, with each compartment containing a therapeutic agent that can be the same as the others or that can be different from the others.

As used herein, the term "therapeutic agent compartment" refers to the locus of the therapeutic agent, whether the therapeutic agent is inserted into a preformed space within the orally ingestible delivery system that acts as the therapeutic agent compartment, or whether the therapeutic agent is incased or enrobed with the external layers of the orally ingestible delivery system without the formation of a discrete space within which the therapeutic agent is directed to reside. For example, the orally ingestible delivery system can be pre-formed with an interior cavity into which a fluid therapeutic agent can be injected. Such a preformed cavity can have other layers of protection or controlled release besides those integral to the differentially permeable (for example, digestible) capsule system 104. Or, as another example, a third party can produce the therapeutic agent with its own enclosure and/or coating(s), for example within a capsule having optional layers of coatings, whereupon that therapeutic agent form factor can be presented for inclusion within the orally ingestible delivery system, for example by forming the differentially permeable capsule system 104 around it, or by encasing it within a preformed differentially permeable capsule system, or by enrobing or dipping the third party therapeutic agent with its own enclosure and/or coating(s) in the materials that will form the differentially permeable capsule system. In all these situations, whether the space is preformed within the orally ingestible delivery system or whether the differentially permeable capsule system is formed to cover, envelop, or enclose a therapeutic agent having its own enclosure and/or coating(s), the locus of residence for the therapeutic agent is to be termed the "therapeutic agent compartment."

While the Figures provided herein indicate a single therapeutic agent compartment, it is understood that there can be multiple therapeutic agent compartments positioned within the orally ingestible delivery system, where the contents of each compartment can be the same or different. For example, one therapeutic agent compartment can contain a first therapeutic agent and another therapeutic agent compartment can contain a second therapeutic agent, both of which act synergistically but have different therapeutic effects: such combinations can thus provide two or more therapeutic agents to a patient in the same delivery system. As another example, one therapeutic agent can contain a first therapeutic agent, and another therapeutic agent compartment can contain a second therapeutic agent, where the second therapeutic agent enhances the effect of the first therapeutic agent without itself having an independent therapeutic effect. As an example, a probiotic therapeutic agent can be delivered in one therapeutic agent compartment and a prebiotic substance can be delivered in another therapeutic agent compartment, with the prebiotic agent intended to enhance the effectiveness of the probiotic substance. Single-pill combinations are recognized as valuable tools for managing chronic conditions like asthma, diabetes, hypertension, and dyslipidemia. Because of its ability to survive passage through the stomach, the orally ingestible delivery system disclosed herein can offer the advantages of combination therapies for therapeutic agents that previously had required parenteral administration.

As shown in FIG. 1, the differentially permeable (for example, digestible) capsule system 104 comprises an acid-resistant shell 108 (for example, an acid resistant protease digestible membrane), on the surface of which or within which is disposed a dispersible acid barrier 110. As used herein, the term "acid-resistant shell" refers to a structural layer of the orally ingestible delivery system 100 that is resistant to the hydrolytic effects of stomach acid. The construction of the acid-resistant shell is described in more detail below in conjunction with the Figures that follow. If the acid-resistant shell 108 completely prevented the incursion and through-passage of stomach fluid, it would prevent digestion of the orally ingestible delivery system 100 within the stomach and it could further impair, delay, or prevent digestion in the intestinal tract. However, the orally ingestible delivery system 100 is intended to be differentially permeable, remaining substantially intact in the stomach but then permitting sufficient digestion in the intestine or sufficient intestinal fluid ingress that the contents of the therapeutic agent chamber 102 can be released from the orally ingestible delivery system 100 at a selected location distal to the stomach.

Hence, the acid-resistant shell can be constructed to permit the ingress of all fluids, whether stomach fluids (i.e., liquid secretions produced in the stomach) or intestinal fluids (i.e., liquid secretions produced by the pancreas, liver, or intestine that reside in the intestinal tract), which structurally allows such fluids to pass through the acid-resistant shell and access the contents of the therapeutic agent chamber 102. However, this unselective passage of fluids through the acid-resistant shell in both the stomach and the intestine is prevented by the dispersible acid barrier 110. The dispersible acid barrier 110 forms within the stomach and prevents stomach fluids from passing into and/or through the acid-resistant shell 108, as is described in more detail below. Then, as the orally ingestible delivery system 100 passes into the intestine, the dispersible acid barrier 110 disperses, allowing intestinal fluids to pass into and through the acid-resistant shell 108, ultimately accessing the contents of the therapeutic agent chamber 102, and optionally resulting in partial or complete destruction of the remainder of the orally ingestible delivery system 100.

The dispersible acid barrier 110 as shown in this Figure is disposed upon the surface of the acid-resistant shell 108 (for example, an acid resistant protease digestible membrane), but it is understood that the dispersible acid barrier 110 can also or instead be deployed within the acid-resistant shell 108, for example within pores or channels in the acid-resistant shell 108, or beneath the acid-resistant shell 108. Certain of these loci for the dispersible acid barrier are illustrated in the Figures. As used herein, the term "dispersible acid barrier" refers to a physical obstruction formed from a fluid or from solid particles (whether coalesced or isolated) that prevents the incursion of stomach acid into and/or through the acid-resistant shell 108. As used herein, a substance termed a "fluid" is in a state of matter that includes materials in the gas phase or the liquid phase, i.e., any substance that flows or deforms under applied shear stress. As used more generally, the term "barrier" refers to any physical obstruction that blocks passage or that prevents or hinders movement or action, for example, a physical obstruction that prevents/hinders stomach acid from entering into the therapeutic agent chamber 102 or that prevents/hinders acid from contacting an external or internal aspect of the acid-resistant shell 108.

In more detail, the dispersible acid barrier 110 can be deployed on the outside of the acid-resistant shell 108 (for example, an acid resistant protease digestible membrane), as shown, or it can be deployed within the acid-resistant shell 108 (not shown), or both, to protect the acid-resistant shell 108 from contact (in whole or in part) with stomach acid. It is understood that a dispersible acid barrier 110 on the surface of the acid-resistant shell 108 can comprise different substances than a dispersible acid barrier deployed within the acid-resistant shell 108, and that these different compositions for dispersible acid barriers can coexist within a single orally ingestible delivery system 100. As used herein, the terms "dispersible," "disperse," and the like refer without limitation to those processes by which the barrier (whether gas, liquid, or solid) is dispelled, decomposed, dissolved, scattered, dissipated, destroyed, chemically altered to affect its physical properties and/or integrity, or are otherwise removed from or diminished in its original location. The term shall include the process of dissolving that takes place when the barrier components (for example $CO_2$ gas bubbles produced in the stomach to form the acid barrier) equilibrate in a more pH-neutral solution such as is found in the duodenum to form the conjugate acid (for example, carbonic acid). The term shall also include the process of emulsification, solubilizing, hydrolysis, and the like, that takes place when barrier components (for example, oils, waxes, or other hydrophilic fluids or solids) encounter bile salts, lipases, and the like, in the duodenum. In embodiments, the dispersible acid barrier 110, once formed, can provide a hydrophobic outer layer as shown that protects the underlying acid-resistant shell 108 from further contact with the stomach acid. In other embodiments, the dispersible acid barrier 110 can provide mechanical obstruction within the acid-resistant shell 108 to block the penetration of the stomach acid into the acid-resistant shell itself 108.

The dispersible acid barrier 110 can, in an embodiment, be formed by a reaction between gas-producing substances (not shown) embedded in or otherwise disposed within or in contiguity with the acid-resistant shell 108 (for example, an acid resistant protease digestible membrane), as are described in more detail below. As used herein, the term "gas-producing substance" refers to a material that produces a gas when it reacts with the acid in the gastric juice. An example of a gas-producing substance is a solid bicarbonate particle, which, upon contact with stomach acid forms carbon dioxide gas, although other examples will be apparent to skilled artisans. Carbon dioxide gas can form a dispersible acid barrier 110 within and/or on top of the acid resistant shell, acting to prevent further incursion of stomach acid but being dispersible within the duodenum because of the pH difference between the stomach and the duodenum, as described below in more detail.

As shown in this and other Figures, the dispersible acid barrier 110 can exist on the surface of the acid-resistant shell 108 (for example, an acid resistant protease digestible membrane), and any extensions or originations of the dispersible acid barrier 110 within the acid-resistant shell 108 are not shown; however, in other embodiments (for example, those shown in FIGS. 8-11), the dispersible acid barrier 110 forms within the acid-resistant shell 108 either extending outward to form a contiguous or non-contiguous barrier layer on the surface, or remaining contained within the acid-resistant shell 108, or both. In yet other embodiments, the dispersible acid barrier 110 forms within or adjacent to the acid-resistant shell 108 from substances deployed within a separate layer that respond to contact with stomach acid to form fluid obstructions within the acid-resistant shell 108 itself.

The acid-resistant shell 108 (for example, an acid resistant protease digestible membrane) can be formed as a two-layer membrane, a one-layer membrane, or a multilayer membrane, as described below in more detail. In an embodiment, the acid-resistant shell 108 is formed with a hydrophobic layer that imparts acid resistance. It can be combined with other components (whether separate layers, integrated layers, or enclosed/coated/encapsulated therapeutic agents within the therapeutic agent compartment 102) to form the differentially permeable (for example, digestible) capsule system 104. For example, the acid-resistant shell 108, can be formed to surround an inner proteinaceous layer that is protease-digestible (for example, an acid resistant protease digestible membrane); in this embodiment, the acid-resistant shell 108 can be penetrated by a series of pores or channels that are blocked or protected by the dispersible acid barrier 110, so that stomach or duodenal fluids can pass through these pores or channels if the dispersible acid barrier 110 is dispersed, thereby gaining access to the inner proteinaceous layer to effect its digestion. In another embodiment, the acid-resistant shell 108 is formed as a single asymmetric layer with variable properties so that the outer aspect of the single layer has more hydrophobic properties while the inner aspect has a predominance of proteinaceous components that are susceptible to protease digestion.

Those embodiments of the acid-resistant shell 108 that surround or include an inner protease-digestible layer can be termed an "acid-resistant protease-digestible membrane." As used herein, the term "acid-resistant protease-digestible membrane" refers to an acid-resistant shell 108 that structurally comprises a protease-digestible component, either as a separate layer or as an integrated layer. It is understood that the presence of the acid-resistant shell 108 and the protease-digestible component together forming a single acid-resistant protease-digestible membrane is consistent with the function of the acid-resistant protease-digestible membrane within the differentially permeable (for example, digestible) capsule system 104, with each of these two features adding a different element of differential permeability. In more detail, the acid-resistant shell provides acid resistance, preventing or delaying the digestion of the differentially permeable capsule system 104 in the stomach, while the protease-digestible component is digestible in the duodenum. The protease-digestible component would be digestible in the stomach as well, but the dispersible acid barrier 110 (shown in this and subsequent Figures) prevents the stomach enzymes from reaching the protease-digestible component. Thus, a system with an acid-resistant shell 108 and a protease-digestible component forms a differentially permeable capsule system 104, permitting differential passage of stomach fluids and duodenal fluids into the orally ingestible delivery system 100. As used herein, the term "acid-resistant shell" can comprise the acid-resistant feature of an integrated acid-resistant protease-digestible membrane, or it can refer to the acid-resistant layer alone.

In certain embodiments, the acid-resistant shell 108 or acid-resistant protease-digestible membrane includes other layers to impart other advantageous properties, for example a layer adding mechanical strength or stability, containing for example embedded biodegradable structural supports, or an external layer to be digested in the stomach that affords mechanical protection during passage through the mouth and esophagus, or a mesh layer disposed in whole or in part over the outer aspect of the acid-resistant shell, to provide structural support or elastic resiliency.

Figure 2:
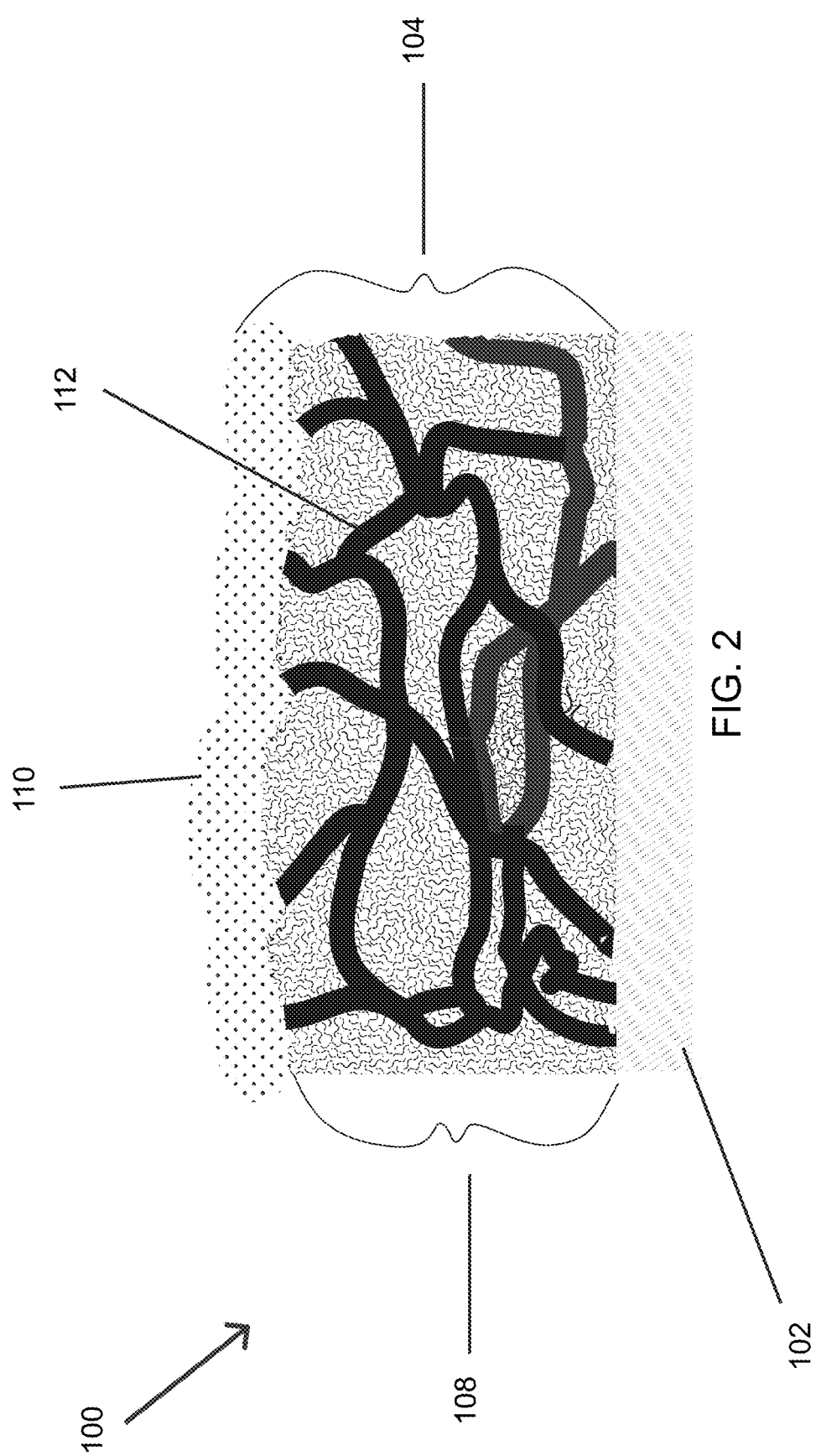
FIG. 2 depicts schematically a segment of an embodiment of an orally ingestible delivery system in cross-section.

FIG. 2 shows a section of the orally ingestible delivery system 100 as had been depicted in FIG. 1, with the section of FIG. 2 being taken at the line A-A' that is shown in FIG. 1. As seen in FIG. 2, the differentially permeable (for example, digestible) capsule system 104 encloses the therapeutic agent in the therapeutic agent compartment 102. As is described in more detail below, the therapeutic agent compartment 102 can contain one or more therapeutic agent deliverables (pills, granules, powder, liquid, etc.), with or without other covering layers. For example, the therapeutic agent(s) in the therapeutic agent compartment can be enclosed by protease-digestible layers such as gelatin, or by other protective or delayed-release coatings familiar in the pharmaceutical art.

The differentially permeable (for example, digestible) capsule system 104 comprises an acid-resistant shell 108 (for example, an acid resistant protease digestible membrane) and a dispersible acid barrier 110, here depicted on the surface of the acid-resistant shell 108. As shown in FIG. 2, the acid-resistant shell 108 can be formed as a single layer, although, as described above, other arrangements of the acid-resistant shell can be envisioned, which can include a protease-digestible component to form an acid-resistant protease-digestible membrane. As shown, the acid-resistant shell 108 is penetrated by a system of pores 112 that are disposed throughout the layer, with certain of the pores opening internally, in fluid communication with the therapeutic agent compartment 102, and with other pores opening externally, in fluid communication with the dispersible acid barrier 110. The system of pores 112 is interconnected, so that the system of pores 112 provides fluid communication between the external aspect of acid-resistant shell 108 and the therapeutic agent compartment 102. In embodiments, the pores are disposed within acid-resistant shell 108 in a latticework or network system, with the pore channels intersecting within the membrane itself. In more detail, the system of pores 112 penetrating the acid-resistant shell 108 can be straight, curved, serpiginous, separated, intersecting, or any configuration that would provide access through the acid-resistant shell 108 to provide ultimate access to the therapeutic agent compartment 102. In embodiments, the pores can be less serpiginous and more linear, allowing a more direct passage from the external aspect of the acid-resistant shell 108 to the therapeutic acid compartment 102. In other embodiments (not depicted in this Figure) pores can be non-intersecting, disposed for example as a plurality of single channels without networking. In embodiments, the pores in the system of pores 112 are dimensioned to have a micron-scale entry diameter, for example an entry diameter of about 10 microns, or between about 1 to about 10 microns, or between about 100 nm and about 10 microns, although other pore sizes, shapes and configurations can be readily engineered. While FIG. 2 depicts a system of pores 112 without contents, entrance into which is deflected by the externally-disposed dispersible acid barrier 110, it is understood that the pores themselves may contain some form of dispersible acid-barrier substances (not shown), whether fluid or solid, the presence of which can supplement or replace the dispersible acid barrier 110 deployed on the surface of the acid-resistant shell 108. The dispersible acid-barrier substances within the pores can be the same as or different than the dispersible acid barrier 110 that forms on the surface of the acid-resistant shell 108.

In certain embodiments, the acid-resistant shell 108 (for example, an acid resistant protease digestible membrane) can be formed uniformly and homogenously, with pores 112 dispersed therein. In other embodiments, the acid-resistant shell 108 can be formed by an amalgamation of discontinuous acid-resistant particles, droplets, fibers, or the like, which are positioned in sufficient proximity or juxtaposition to each other that they form a barrier layer that prevents or impedes the inflow of fluids from the surrounding environment.

Figure 3:
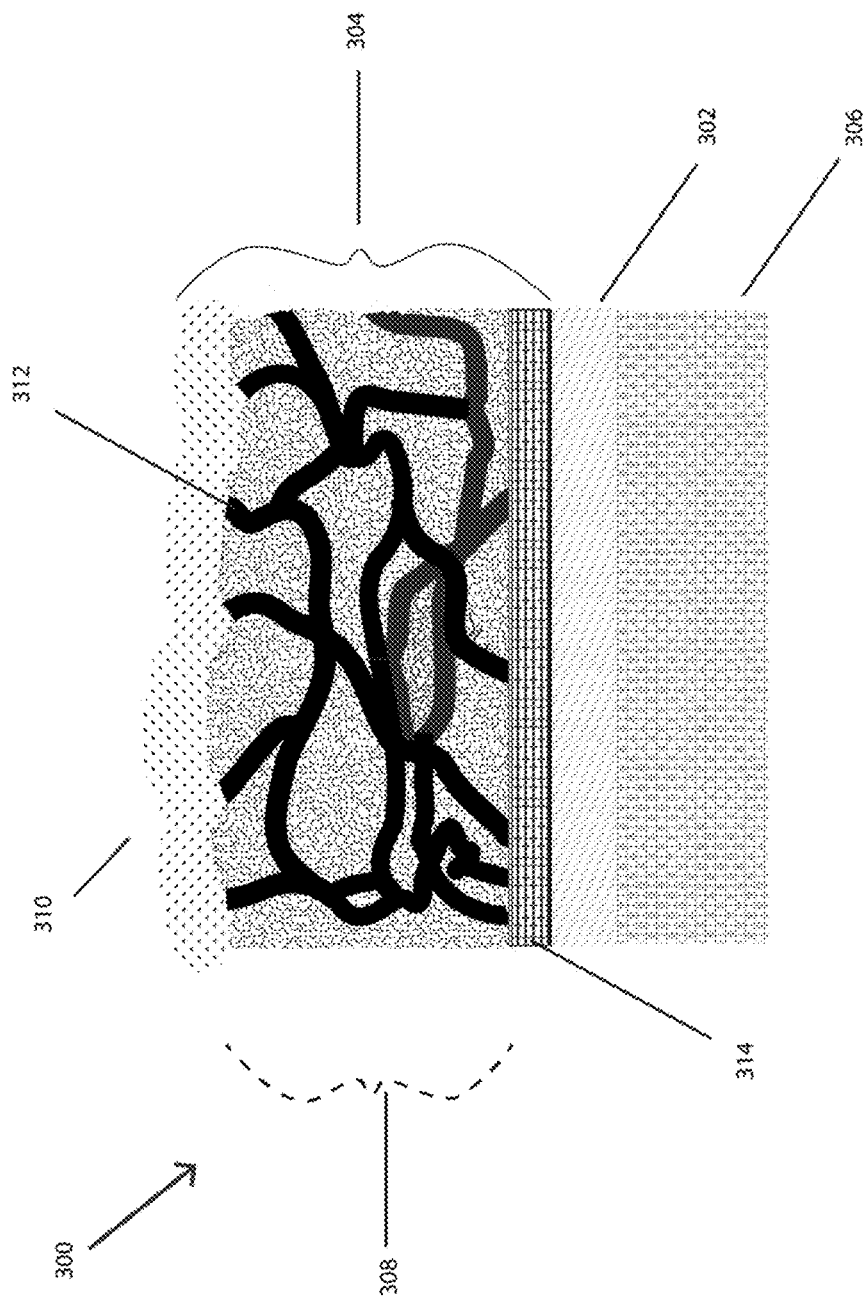
FIG. 3 depicts schematically a segment of an embodiment of an orally ingestible delivery system in cross-section.

FIG. 3 shows an embodiment of an orally ingestible delivery system 300 following its ingestion and after a period of residence in the stomach. The differentially permeable (for example, digestible) capsule system 304, comprising an acid-resistant shell 308 and a dispersible acid barrier 310 (here shown on the surface of the acid-resistant shell 308), encloses the therapeutic agent compartment 302, within which is disposed the one or more therapeutic agents 306.

In more detail, the acid-resistant shell 308 (for example, an acid resistant protease digestible membrane) provides an outer acid-resistant layer that can be formed from any material resistant to the hydrolytic activity of stomach acid. In an embodiment, a waxy substance such as beeswax, soybean wax, carnauba wax, and the like, can be used as the base substrate for the outer acid-resistant layer. As used herein, the term "wax" refers to any hydrocarbon that is lipophilic and a malleable solid near ambient temperatures, typically having a melting point above about 40° C. As examples, waxes can include long-chain aliphatic hydrocarbons typically having 20-40 carbon atoms per molecule, or fatty acid/alcohol esters typically containing from 12-32 carbon atoms per molecule, such as myricyl cerotate, found in beeswax and carnauba wax.

The therapeutic agent(s) 306 can be formulated as solids, semi-solids, liquids, gels, or some combination thereof. As depicted in this Figure, a therapeutic agent 306 is enclosed within the therapeutic agent compartment 302, where the therapeutic agent compartment 302 can be formed from a wall or an additional layer enveloping the therapeutic agent 306. In embodiments, the therapeutic agent 306 can reside within a walled therapeutic agent compartment 302 where the wall is intended to modify in some way the delivery of the therapeutic agent 306 from the orally ingestible delivery system 300. The wall of the therapeutic agent compartment 302 can be engineered to provide a modification of the therapeutic agent's 306 release, or provide mechanical protection, or provide further resistance against proteases that may penetrate the acid-resistant shell 308. In other embodiments, the therapeutic agent compartment 302 is a void within which the therapeutic agent 306 resides, without additional enclosing layers. In embodiments, the therapeutic agent 306 can reside within the therapeutic agent compartment 302 without a separate enveloping layer.

In embodiments, one or more therapeutic agents 306 can exist within the therapeutic agent compartment 302, each with its own enveloping layer; when the therapeutic agent deliverable comprises a plurality of therapeutic agents, a separate enveloping layer may be provided to enclose two or more of the therapeutic agents. Single or multiple therapeutic agents can reside within the therapeutic agent compartment 302, altogether comprising the therapeutic agent deliverable. As used herein, the term "therapeutic agent deliverable" refers to the entire contents of the therapeutic agent compartment 302, which can include multiple therapeutic agents packaged separately, or a therapeutic agent and a supporting milieu, or other variations of dosage forms for one or more therapeutic agents 306 as discrete units. In embodiments, each therapeutic agent 306 within the therapeutic agent compartment 302 can have its own system of enveloping layers, for example to provide mechanical stability after its release from the orally-ingestible delivery system 300, or to modify its release profile, or to enhance its uptake or its therapeutic effects. In such embodiments, the therapeutic agent 306 thus formulated, for example with a system of enveloping layers, can be inserted intact into the therapeutic agent compartment 302 with its release properties provided by its own formulation, so that no special modification of the orally-ingestible delivery system is necessary to optimize the therapeutic agent's 306 release. In such a situation, the therapeutic agent 306 with its appropriate release-modifying formulation can be inserted into an empty therapeutic agent compartment 302, i.e., a therapeutic agent compartment 302 formed as a void without special walls or other envelopments apart from the acid-resistant shell 308 and its components, optionally with the inclusion of an inner protease-digestible layer 314. A membrane formed by combining the acid-resistant shell and the inner protease-digestible component can be termed an acid-resistant protease-digestible membrane, which would include the acid-resistant shell 308 and the inner protease-digestible layer 314 that are shown in the depicted embodiment. Alternatively or in addition, the therapeutic agent 306 with its appropriate release-modifying formulations can be enrobed, enveloped, or otherwise encased by or within the acid-resistant shell 308, with the enrobing, envelopment, or encasing forming de facto the therapeutic agent compartment 302 as these processes deploy the acid-resistant shell 308 to surround the therapeutic agent 306 or therapeutic agent deliverable. In embodiments, the therapeutic agent 306 can be a solid, liquid, or gel, and can optionally be encased within a protease-digestible layer 314 such as a gelatin capsule. In the depicted embodiment, the protease-digestible layer 314 acts as an outer wall of the therapeutic agent compartment 302. In other embodiments, the protease-digestible layer 314 is absent. In the embodiment shown in FIG. 3, the acid-resistant shell 308 of the differentially permeable (for example, digestible) capsule system 304 can enclose the optional inner protease-digestible layer 314, with the two layers together forming an acid-resistant protease-digestible membrane. In embodiments, the outer acid-resistant shell 308 is impervious to or only minimally susceptible to the effects of stomach acid, while in other embodiments, the outer acid-resistant shell 308 is relatively less susceptible to the effects of stomach acid as compared to the optional protease-digestible layer 314. In the depicted embodiment, the outer acid-resistant shell 308 is penetrated by a system of pores 312 that are disposed throughout the layer 308, with certain of the pores opening on the external aspect of the acid-resistant shell 308 in contact with the dispersible acid barrier 310, and certain of the pores opening onto the internal aspect of the acid-resistant shell 308 and contacting the protease-digestible layer 314. As shown in FIG. 3, the system of pores 312 only penetrates the acid-resistant shell 308, with some or all of the pores communicating with the external aspect of the acid-resistant shell 308 and also with the protease-digestible layer 314. In embodiments, the pores are disposed within the acid-resistant shell 308 in a latticework or network system, with the pore channels intersecting with each other within the acid-resistant shell 308. In more detail, the system of pores 312 penetrating acid-resistant shell 308 can be straight, curved, serpiginous, separated, intersecting, or any configuration that would provide access through the acid-resistant shell 308, with some or all of the pores abutting upon the inner protease-digestible layer 314. In other embodiments (not depicted in this Figure) pores can be non-intersecting, disposed for example as a plurality of single channels without networking. In embodiments, the pores in the system of pores 312 are dimensioned to have a micron-scale entry diameter, for example an entry diameter of about 10 microns, or between about 1 to about 10 microns.

As previously described, in embodiments, the dispersible acid barrier 310 on the surface of the acid-resistant shell 308 can prevent the entrance of stomach acid into the system of pores; in other embodiments, the pores can contain dispersible acid-barrier substances (not shown) whether fluid or solid, which prevent the ingress of stomach acid, and which can replace or supplement the dispersible acid barrier 310 deployed on the surface of the acid-resistant shell 308 (for example, an acid resistant protease digestible membrane). It is understood that the dispersible acid-barrier substances within the pores can be the same as or different than the dispersible acid barrier 310 that forms on the surface of the acid-resistant shell 308.

As shown in FIG. 3, the acid-resistant shell 308 (for example, an acid resistant protease digestible membrane) has an irregular surface. Without being bound by theory, it is understood that the irregularities in the membrane surface can exploit the phenomenon of surface tension to improve the attachment of fluids (i.e., gas or liquids) or solid particles to the surface, thereby making the dispersible acid barrier more robust. While the dispersible acid barrier 310 is shown in this Figure as having continuity over the surface of the acid-resistant shell 308, the dispersible acid barrier 310 can also be discontinuous in any arrangement, for example residing only within grooves or depressions in the acid-resistant shell 308, or residing in areas surrounding the openings of the pores into the outer aspect of the acid-resistant shell 308, or in any other configuration that facilitates its function of repelling stomach liquids from contacting the acid-resistant shell 308. As mentioned previously, while the dispersible acid barrier 310 is shown only on the surface of the acid-resistant shell 308, a dispersible acid barrier can also be formed and retained within the system of pores 312, as will be shown in subsequent Figures.

As described previously, the orally ingestible delivery system 300 comes to reside in the stomach following ingestion, where it encounters the acid and enzymes in the gastric juice. When the orally ingestible delivery system 300 enters the stomach, it is enveloped by stomach acid, which interacts with the features of the delivery system as described herein and below. As a result of its encounter with the stomach acid, the system depicted in FIG. 3 forms a dispersible acid barrier 310 on its surface. In embodiments, the orally ingestible delivery system 300 can encounter an acid milieu prior to its ingestion, and it would respond similarly to how it responds to stomach acid. In an embodiment wherein the dispersible acid barrier 310 forms after encountering acid, the orally ingestible delivery system 300 can be pretreated with acid before it reaches the stomach to accelerate the formation of the dispersible acid barrier 310. For example, the orally ingestible delivery system 300 can be provided in an acid milieu for ingestion, or it can be swallowed along with an acid liquid, gel or solid. Under these conditions, such a pretreatment with acid initiates the mechanisms for producing the dispersible acid barrier, both before the orally ingestible delivery system reaches the stomach and afterwards. If the orally ingestible delivery system 300 has been exposed to acid prior to reaching the stomach, it is understood that further contact with stomach acid can continue the process of producing the dispersible acid barrier 310.

Figure 4:
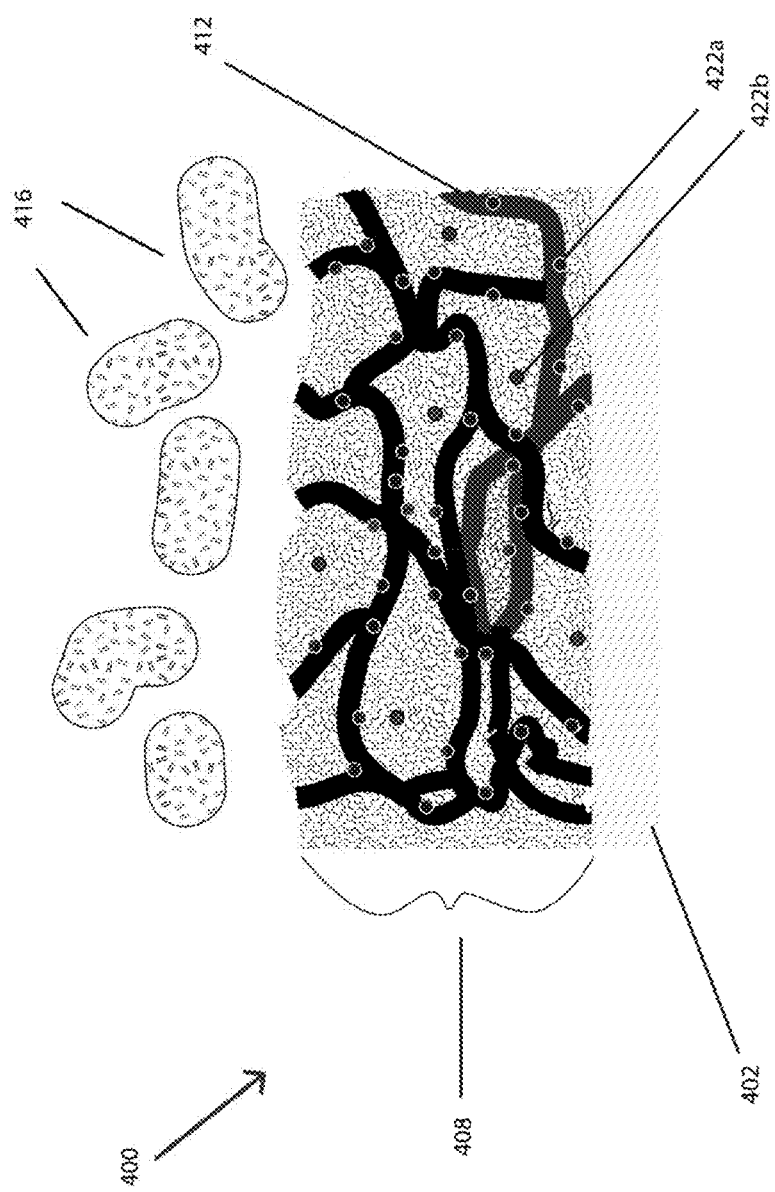
FIG. 4 depicts schematically a segment of an embodiment of an orally ingestible delivery system in cross-section.
Figure 5:
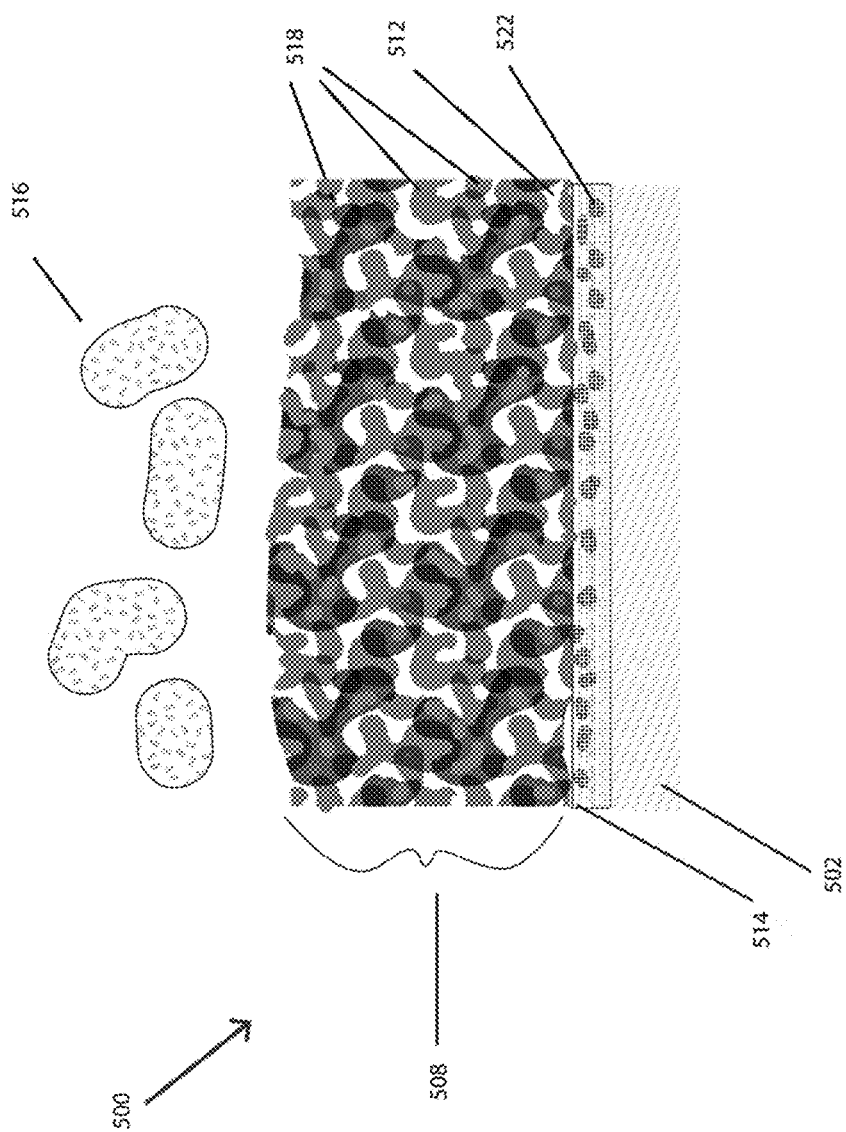
FIG. 5 depicts schematically a segment of an embodiment of an orally ingestible delivery system in cross-section.
Figure 6:
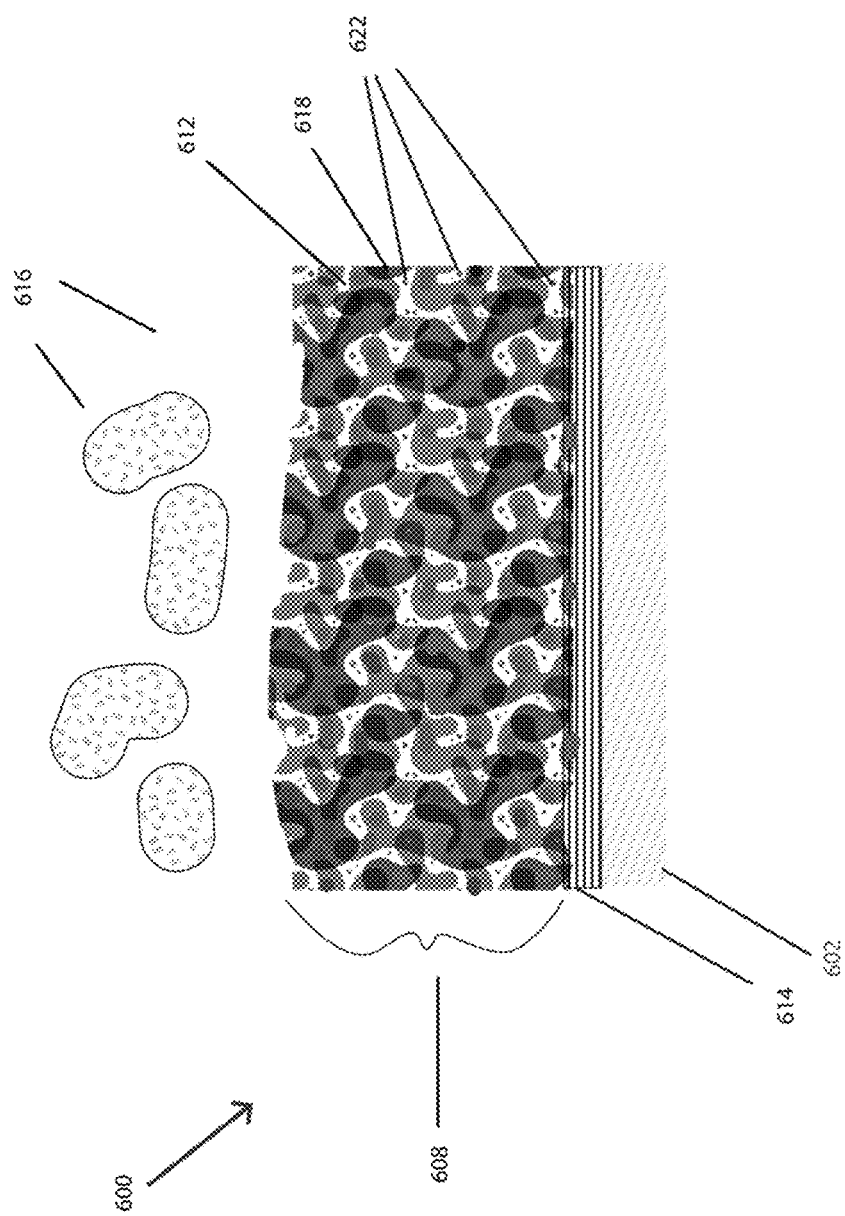
FIG. 6 depicts schematically a segment of an embodiment of an orally ingestible delivery system in cross-section.

Certain mechanisms by which the orally ingestible deliver system interacts with stomach acid or other acid are illustrated schematically in FIGS. 4, 5, and 6 in more detail.

As shown in FIG. 4, the orally ingestible delivery system 400 is exposed to stomach fluid 416 containing acid and stomach enzymes, whether prior to ingestion, during ingestion, or as it enters the stomach. As previously described and illustrated in FIGS. 1 and 2, the orally ingestible delivery system 400 comprises an acid-resistant shell 408 (for example, an acid resistant protease digestible membrane) surrounding a therapeutic agent compartment 402. In embodiments, the surface of the acid-resistant shell 408 can be covered with a soluble or digestible coating (not shown) that is rapidly eroded in the stomach, for example, a coating made of gelatin, polysaccharide, or some other digestible biopolymer. Such a coating can provide mechanical protection to the orally ingestible delivery system 400 during its storage, handling, and oral ingestion. In other embodiments, the coating can be formed as a mesh or network of elongate elements or fibers, which can provide structural stability, durability, or elasticity. In embodiments, the coating can protect underlying components until the coating is eroded, damaged, or destroyed in the stomach. For example, gas-producing substances can be arranged beneath the coating and on top of the acid-resistant shell, so that they can react with stomach acid as the coating deteriorates, thereby forming a layer of gas (not shown) that protects the external aspect of the acid-resistant shell 408.

In embodiments, agents can be added to acid-resistant shell 408 (for example, an acid resistant protease digestible membrane) or any complete or partial overlay applied thereto to enhance its strength or resiliency in the face of the mechanical stresses in the stomach. For example, the strength or resiliency of the acid-resistant shell 408 can be improved by adding substances such as polyisobutylene or other comparable agents to the matrix used to form this layer, as described below in more detail. In other embodiments, the acid-resistant shell 408, here shown as a single layer, can be constructed with multiple layers, or combined with other layers, for example as described in FIG. 3, where an outer acid-resistant layer covers an inner protease-digestible layer to form a single acid-resistant protease-digestible membrane.

As shown in the depicted embodiment, the acid-resistant shell 408 (for example, an acid resistant protease digestible membrane) has within its matrix a networked and intersecting system of pores 412 that enter the external aspect of the acid-resistant shell 408 and spread throughout its matrix. In embodiments, the acid-resistant shell 408 can be perfused with deposits of gas-producing substances whereby contact between the gas-producing substances and the stomach acid releases gas from the gas-producing substances within the outer acid-resistant layer.

In the depicted embodiment, the pores 412 themselves are not completely obstructed by barrier-forming substances 422 throughout the entire network of pores. Therefore, when the acid 416 (for example in the gastric juice) initially encounters the pores 412 that penetrate the outer surface of the acid-resistant shell 408 (i.e., before the formation of any dispersible acid barrier), the acid 416 is able to enter the pores and diffuse through them, encountering deposits 422a of barrier-forming substances dispersed within the pores and optionally deposits 422b of barrier-forming substances dispersed within the matrix of the acid-resistant shell 408. These deposits 422a and/or 422b, upon encountering the stomach acid in the stomach fluid 416, react with the acid and/or enzymes in the stomach fluid to produce the acid-barrier layer shown in previous Figures. In embodiments, the barrier-forming substances 422a and/or 422b can be preferentially deployed in the more superficial aspects of the pores 412 and the matrix, so that any stomach acid that enters the pores 412 will encounter the barrier-forming substances 422a and/or 422b fairly quickly, forming gas that prevents further incursion of stomach acid and thereby protecting the underlying therapeutic agent from the effects of the stomach fluid 416.

In embodiments, the barrier-forming substances 422a and 422b can be gas-forming substances that produce or release gas upon contact with the hydrochloric acid in the stomach. As an example, the barrier-forming substances 422a and/or 422b can comprise bicarbonate crystals that form carbon dioxide after contact with stomach acid in the stomach fluid 416, with the carbon dioxide entering the pores 412 and optionally coming to reside on the surface of the acid-resistant shell 408 (for example, an acid resistant protease digestible membrane), wherein the presence of the carbon dioxide acts as an dispersible acid barrier, mechanically preventing the further exposure of the acid-resistant shell 408 to stomach fluid, either by coating its surface, blocking the pores or other channels in the acid-resistant shell 408, or both. Such barrier-forming substances, where their encounter with the hydrochloric acid forms a gas, are termed "gas-forming substances" herein. As examples, carbonate-containing substances including metal carbonates such as, but not limited to, calcium carbonate (including precipitated calcium carbonate (PCC)), sodium bicarbonate, potassium bicarbonate, magnesium carbonate, and the like) are gas-forming substances because they form carbon dioxide upon encounter with hydrochloric acid, as are hydrogen formers such as magnesium particles and the like.

Barrier-forming substances can be concentrated in the pores 422a or dispersed with in the matrix 422b or both, as depicted in the Figure. For example, barrier-forming substances can also be scattered in deposits 422b randomly through the acid-resistant shell 408, instead of, or in addition to, the barrier-forming substances contained 422a. Thus, the barrier-forming substances are contacted by the stomach acid in the stomach fluid 416 as it enters the pores or invades the acid-resistant shell 408 (for example, an acid resistant protease digestible membrane) or both. The dispersible acid barrier 408 formed by the contact of the stomach acid contained in the stomach fluid 416 with the barrier-forming substances can enter the pores from the matrix if the barrier-forming substances are deployed within the matrix 422b, or the dispersible acid barrier can form within the pores if the barrier-forming substances are contained 422a in the pores.

In embodiments, additional barrier-forming substances can be dispersed within other components of the orally-ingestible delivery system 400, for example in a gas-producing layer (not shown) to be added between two or more layers of the acid-resistant shell (not shown) or below the acid-resistant shell 408, or as discrete deposits contained within the therapeutic agent compartment 402, or within the therapeutic agent or therapeutic agent deliverable itself. It is understood that the barrier-forming substances in various locations, for example in deposits 422a within the pores 412 and in deposits 422b within the matrix or dispersed within other components of the orally ingestible delivery system 400, can comprise different substances or formulations.

In this Figure, the acid-resistant shell 408 (for example, an acid resistant protease digestible membrane) contains a plurality of deposits 422a and 422b of barrier-forming substances dispersed throughout the acid-resistant shell 408. Some of the deposits 422a reside within pores or are in partial contact to the pores in the system of pores, while other deposits 422b are encased within the substance of the acid-resistant shell 408 without contact with the pores. In certain embodiments the pores in the system of pores 412 are constructed to be hollow, with the deposits 422a of barrier-forming substances residing therein or otherwise being accessible to gastric juice 416 that enters the hollow pores. In yet other embodiments (not shown in the Figure), some or all of the system of pores 412 can contain a paste or an oil, for example an edible oil, within which the deposits 422a can be dispersed. Such an oil can have a viscosity that is engineered to retain it within the pores, and it can be selected to resist oxidation, hydrolysis, and other deleterious processes that could affect its durability and shelf-life. For example, an unsaturated oil or oil blend can be selected. Filling the pore system 412 with a paste or an oil can afford additional protection for the acid-resistant shell 408, preventing ingress of liquids from the stomach and thus preventing stomach acid and enzymes from encountering the membrane 408 from within. In other embodiments, the architecture for the pores can be patterned with digestible materials scattered throughout the acid-resistant shell 408 as it is formed and deposited on the therapeutic agent compartment or on the therapeutic agent itself. As part of the same process for forming the acid-resistant shell 408, barrier-forming substances can be scattered throughout the matrix in a random pattern, or they can be attached to fibers (not shown) dispersed within the matrix and/or within the pores. In embodiments, the fibers are digestible or hydrolysable, so that when they are digested or hydrolyzed, the acid 416 in the acid milieu is brought into contact with barrier-forming substances that are thereby activated to produce a fluid that fills the orally ingestible delivery system or pores left behind after the digestion of the fibers. Some of the fluid produced by the barrier-forming substances can pass through the pores and comes to reside on the surface of acid-resistant shell 408 as a dispersible acid barrier (not shown). The dispersible acid barrier thus formed (including the external fluid layer and the fluid that fills the pores) prevents further acid 416 from re-entering the acid-resistant shell 408 to effect its digestion.

As shown in FIG. 4, the barrier-forming substances 422a and 422b have not yet come into contact with any acid in the stomach fluid 416, and thus any fluid that will become the dispersible acid barrier penetrating and covering the acid-resistant shell 408 has not yet been formed. Describing the system and its mechanisms of activation in more detail with reference to FIG. 4: first, the acid in the stomach fluid 416 enters the system of pores 412, (for example, in the stomach, the hydrochloric acid comes into contact with the barrier-forming substance within the pores and/or within the matrix of the acid-resistant shell 408); then, after contact with the acid, the deposits 422a form the fluid that forms the dispersible acid barrier within the pores and on the surface; the surface component of the dispersible acid barrier has already been shown in FIGS. 1, 2, 3, and 5 but is not shown in FIG. 4.

While FIG. 4 shows the plurality of deposits 422a and 422b as being substantially similar in size, it is understood that the size of the deposits 422a and 422b can be similar or varied, and that the deposits can be regularly or randomly dispersed throughout the matrix of the acid-resistant shell 408 (for example, an acid resistant protease digestible membrane) and within the pores of the system of pores 412. In cases where certain of the deposits 422b are entirely encased within the matrix of the acid-resistant shell 408, porous fibers or other media permitting liquid transport can be embedded in the matrix while contacting the pores, thereby permitting the acid entering the pores to be conducted into and within the matrix of the acid-resistant shell 408 so that such acid contacts the deposits 422b embedded in the matrix; fluid produced through the contact of the acid with the deposits 422b can exit the matrix and enter the pores through the channels or orally ingestible delivery system previously occupied by the porous fibers or other media. This reaction between the barrier-forming substances and the stomach acid results in the production of fluid (not shown) that traverses the system of pores 412, in some cases blocking the pores entirely and remaining within the pores by forces of surface tension, and in other cases exiting the system of pores to become deposited on the surface of the acid-resistant shell 408. These bubbles or droplets of fluid can coalesce on the surface of the acid-resistant shell 408 to form the dispersible acid barrier on the surface as shown in other Figures. While the dispersible acid barrier layer has been depicted in previous Figures as continuous or nearly continuous, it is understood that the bubbles or droplets (whether separate or confluent) forming the dispersible acid barrier (i.e., the fluid-filled pores) can be segregated regionally to produce their barrier effects. For example, the bubbles or droplets (whether separate or confluent) can be localized at the pore orifices, acting as a "cap" on the pores without spreading out over the remaining surface of the acid-resistant shell 408. Or, for example, fluid bubbles or droplets (whether separate or confluent) can also or alternatively reside within grooves or irregularities on the surface of the acid-resistant shell 408, retaining their attachment via surface tension. Other arrangements of the fluid bubbles or droplets (whether separate or confluent) on the membrane surface and/or within the pores can be envisioned that are consistent with the role of the dispersible acid barrier, i.e., providing a mechanical blockade that protects the acid-resistant shell 408 in the stomach while dispersing within the duodenum to allow duodenal enzymes to access and dissolve the membrane.

Modifications of the acid-resistant shell 408 (for example, an acid resistant protease digestible membrane) may be made to enhance the attachment or the localization of the droplets or bubbles (whether separate or confluent) on its surface. For example, fibers contained within the matrix of the acid-resistant shell 408 may be arranged to protrude from its surface to trap droplets or bubbles (whether separate or confluent) on the surface in certain regions and to improve their attachment. Such fibers (not shown) can be scattered through the matrix in a regular pattern or can be differentially arranged so that they are predominately disposed on the external aspect of the acid-resistant shell 408. In other embodiments, fibers that function to trap or retain droplets or bubbles (whether separate or confluent) can be attached to or disposed upon the outer surface of the acid-resistant shell 408 separately, without embedding them in the matrix, or they can be concentrated around the orifices of the system of pores 412. In embodiments, barrier-forming substances can be disposed on the surface or in the superficial portion of the acid-resistant shell 408 to enhance the production of a dispersible acid barrier on the membrane's surface.

FIG. 5 shows another embodiment of a cross-section of an orally ingestible delivery system 500 as it is exposed to acid-containing fluid 516 (for example, stomach fluid containing acid and stomach enzymes). In the depicted embodiment, an acid-resistant shell (for example, an acid resistant protease digestible membrane) 508 surrounds a therapeutic agent compartment 502. The acid-resistant shell 508 can be formed non-continuously, with islands or droplets or masses of acid-resistant material 518 deposited on top of each other to form a consolidated layer. For example, if the consolidated layer is formed by spraying, the islands or droplets or masses of acid-resistant material 518, for example, sprayed particulate matter in suspension can be deposited as discontinuous masses of liquid, solid, or gel on top of and adjacent to each other to form the substantially solid layer of the acid-resistant shell 508. Channels, voids, or pores 512 are formed during the deposition process as the sprayed materials 518 are layered or otherwise deployed to contact each other without completely coalescing. These channels, voids, or pores 512 can penetrate the acid-resistant shell 508 completely, potentially allowing the external acid-containing fluid 516 to reach the therapeutic agent compartment 502.

In the depicted embodiment, an inner erodible layer 514, for example a layer of acid-digestible or protease-digestible material, is interposed between the acid-resistant shell 508 and the therapeutic agent compartment 502. In embodiments, the combination of the acid-resistant shell 508 and the inner erodible layer 514 forms an acid-resistant protease-digestible membrane, if the inner erodible layer is protease-digestible. As used herein, an "erodible layer" refers to any layer included as a structural component of the orally ingestible delivery system that deteriorates upon exposure to a physical or chemical condition in the stomach or intestinal tract, for example, a protease-digestible layer, an acid-hydrolysable layer, or any other material that can be digested or otherwise destroyed or damaged by physical or chemical conditions in the stomach or intestinal tract.

As shown in this Figure, a plurality of barrier-forming substances 522, for example gas-forming substances, are embedded in this layer 514. These barrier-forming substances 522 can be released or activated when they encounter acid or gas from acid-containing fluid 516 that seeps through the acid-resistant shell 508 (for example, an acid resistant protease digestible membrane). For example, if bicarbonate crystals are deposited within the erodible layer 514 as barrier-forming substances, they can be converted to carbon dioxide gas upon encounter with stomach acid, and the carbon dioxide thus formed can create a dispersible acid barrier as follows. As mentioned above, the acid-containing fluid 516 can access the inner erodible layer 514 by penetrating the channels, voids, or pores 512 that exist in the acid-resistant shell 508 as interstices between the droplets 518 that have been sprayed or otherwise deposited on top of each other without completely becoming confluent. The carbon dioxide gas (not shown) that is released from the deposits of barrier-forming substances 522 (for example, bicarbonate crystals) in the erodible layer 514 then can expand and fill (partially or completely) the channels, voids, or pores 512, filling them sufficiently to prevent further incursion of acid-containing fluid 516.

While FIG. 5 shows an inner erodible layer 514 with the barrier-forming substances 522 substantially enveloped by it, other arrangements of the barrier-forming substances 522 can be envisioned that would minimize or eliminate a discrete inner erodible layer 514. For example, the inner erodible layer 514 can be a thin film with the barrier-forming substances 522 attached thereto (above it or below it) rather than embedded therein. In other embodiments (not shown), the erodible layer 514 can be positioned within the acid-resistant shell 508 at any level and can contain barrier-forming substances that can be released within the acid-resistant shell 508 upon their encounter with the acid containing fluid 516. The inner erodible layer 514 can be a network or mesh with the barrier-forming substances 522 attached thereto or deployed within the interstices of such network or mesh. In the absence of the inner erodible layer 514 the barrier-forming substances 522 can be integrated into the therapeutic agent compartment 502, forming for example a coating around the therapeutic agent deliverable, or enclosed within the therapeutic agent compartment 502 as a liquid or solid surrounding the therapeutic agent deliverable itself. In these situations, the same mechanism would be involved, with the external acid-containing fluid 516 seeping through the interstices 512 in the acid-resistant shell 508 and accessing the barrier-forming substances 522. However, in such an embodiment, the acid-containing fluid would penetrate into the therapeutic agent compartment itself, wherein the acid would activate the barrier-forming substances that are contained therein.

In other embodiments, as depicted in FIG. 6, the barrier-forming substances 622 (shown schematically and not to scale) can be deployed within the matrix of the acid-resistant shell 608 (for example, an acid resistant protease digestible membrane), either in the interstices 612 as shown, or within (not shown) the network or mesh of islands or droplets or masses of acid-resistant material 618. In FIG. 6, the erodible layer 614 does not contain any barrier-forming substances, but instead is simply deployed beneath the acid-resistant shell 608 and on top of the therapeutic agent compartment 602. In embodiments, the combination of the acid-resistant shell 608 and the inner erodible layer 614 forms an acid-resistant protease-digestible membrane, if the inner erodible layer is protease-digestible. The erodible layer 614 can also be omitted, with the barrier-forming substances 622 within the acid-resistant shell 608 providing sufficient barrier protection against the incursion of the acid-containing fluid 616 to protect the therapeutic agent deliverable in the therapeutic agent compartment 602.

In embodiments, the orally ingestible delivery system, for example as shown in FIGS. 5 and 6 and subsequent Figures, can be covered with a soluble or digestible coating (not shown) that is rapidly eroded in the stomach, for example, a coating made of gelatin, polysaccharide, or some other digestible biopolymer. Such a coating can provide mechanical protection to the orally ingestible delivery systems during its storage, handling, and oral ingestion. In embodiments, the coating can protect underlying components until the coating is eroded, damaged, or destroyed in the stomach. For example, gas-producing substances can be arranged beneath the coating and on top of the acid-resistant shell (for example, an acid resistant protease digestible membrane), so that they can react with stomach acid as the coating deteriorates, thereby forming a layer of gas (not shown) that protects the external aspect of the acid-resistant shell 608.

In other embodiments, the coating can be formed as a mesh or network of elongate elements or fibers, which can provide structural stability, durability, or elasticity. In embodiments, agents can be added to acid-resistant shell (for example, an acid resistant protease digestible membrane) or to any complete or partial overlay applied thereto, to enhance its strength or resiliency in the face of the mechanical stresses in the stomach. For example, the strength or resiliency of the acid-resistant shell can be improved by adding substances such as polyisobutylene or other comparable agents to the matrix used to form this layer, as described below in more detail. In other embodiments, the acid-resistant shell, shown in FIGS. 4, 5, and 6 as a single layer, can be constructed with multiple layers or combined with other layers to provide advantageous properties. Other options for the fabrication of the acid-resistant shell will be described below in more detail.

2. Orally Ingestible Delivery System Generally: Passage into the Duodenum

As previously described, the dispersible acid barrier formed when the orally ingestible delivery system encounters an acid environment, for example when it enters the stomach, protects the underlying acid-resistant shell (for example, an acid resistant protease digestible membrane) from the action of stomach acid and enzymes. The dispersible acid barrier, whether internal, external, or both, acts mechanically to insulate the acid-resistant shell from both acid and proteases. Thus, the orally ingestible delivery system can pass through the stomach with the therapeutic agent substantially intact within the therapeutic agent compartment, despite the stomach environment with its low pH and abundance of digestive enzymes.

However, the orally ingestible delivery system is engineered to release the therapeutic agent where it can have therapeutic effect, following its passage through the stomach. This differential susceptibility to the conditions in the stomach and the duodenum characterize the OIDS as comprising a differentially permeable (for example, digestible) capsule system. This selectivity allows the OIDS to survive the stomach with the therapeutic agent relatively intact, and then to release it within the duodenum or other location within the gastrointestinal system.

A first step in the release of the therapeutic agent is the dispersal of the dispersible acid barrier in the duodenum. The dispersible acid barrier can be a gas, such as carbon dioxide, generated in the stomach as described above. When the carbon dioxide encounters the bicarbonate released in the pancreas by the duodenum, it is dispersed, and the mechanical protection it provides is lost. With the dispersion of the outer dispersible acid barrier (if any), the external and/or internal aspects of the acid-resistant shell (for example, an acid resistant protease digestible membrane) is exposed directly to the duodenal enzymes. With the dispersion of the inner dispersible acid barrier, these enzymes are able to enter the pores that penetrate the acid-resistant shell of the differentially permeable (for example, digestible) capsule system. For a single-layer differentially permeable capsule system, the ingress of the duodenal enzymes permits the digestion of the membrane from within the pores. For a double-layer or multiple-layer differentially permeable capsule system, comprising for example an acid-resistant shell and a protease-digestible component (thereby forming an acid-resistant protease-digestible membrane) or another form of erodible inner layer, the ingress of the duodenal enzymes allows these agents to reach the erodible inner layer and digest it, in addition to their digestive activity carried out from within the pores. For multiple-layer differentially permeable capsule systems, having, for example, an outer acid-resistant layer and an inner erodible layer, the digestion and subsequent collapse of the inner erodible layer can deprive the outer acid-resistant layer of structural support, causing it to deteriorate. With the deterioration of the outer acid-resistant layer, there can be increased contact between the duodenal enzymes and the erodible layer, so that the digestion of this layer can be accelerated.

Dispersible acid barriers formed by space-occupying fluids or solids behave analogously as the orally ingestible delivery system passes through the stomach into the duodenum. As described above, a space-occupying fluid or solid that provides or contributes to the dispersible acid barrier is selected so that it is resistant to stomach acid, but so that it is dispersible (for example, soluble) in the duodenum. As an example, a nonpolar oil that is selected as the space-occupying fluid can be unaffected by stomach acid, remaining within the pores of the orally ingestible delivery system as it was originally deployed. When the device enters the duodenum however, the bile salts and lipases allow the non-polar oil to be dispersed (here, emulsified and digested), so that it is removed from the pores of the device, thereby opening them to the incursion of the duodenal proteases that can destroy the device sufficiently that the therapeutic agent within it is released. As another example, space-occupying solids can be positioned within the pores so that these solids are unaffected by the stomach acid, or so that they can respond to the stomach acid by forming other space-occupying bodies, whether solid, liquid, or gas. The space-occupying solids themselves can react to the duodenal fluid to disperse (as is seen with carbon dioxide gas is dispersed either as a gas or as a fluid after its reaction with bicarbonate in the duodenum), or the reaction products of the solids that are formed in the stomach can be susceptible to the action of the duodenal fluid, leading to their dispersal. With space-occupying fluids or solids, as with space-occupying gases, the dispersal in the intestine allows the entry of digestive fluids from the duodenum into the pores of the orally ingestible delivery system; this access enables digestive fluids such as proteases to act further upon the acid-resistant shell (for example, an acid resistant protease digestible membrane) of the orally ingestible delivery system to break it down enough that the therapeutic agent is released.

In more detail, digestive enzymes are produced not only in the stomach but also in the pancreas, which delivers its enzymes into the duodenum via the pancreatic duct. The main enzyme produced in the stomach is pepsin, which is responsible for initiating the breakdown of proteins in food. Pepsin is formed by the cleavage of its precursor pepsinogen by stomach acid. The stomach also produces lipase, which begins the hydrolysis of lipids in the stomach contents before this material passes into the duodenum. As described above, the dispersible acid barrier formed on the surface and/or in the pores of the orally ingestible delivery system protects the underlying acid-resistant shell from the action of all of these enzymes.

Once the orally ingestible delivery system enters the duodenum, it encounters a different environment. The pancreas delivers bicarbonate into the duodenum that neutralizes the acid pH of the stomach chyme. The pancreas also delivers protease precursors into the duodenum, where they are activated to form the proteases trypsin and chymotrypsin. Other pancreatic enzymes include carboxypeptidase, pancreatic lipase, phospholipase, sterol esterase, and several elastases and nucleases. The acid-resistant shell (for example, an acid resistant protease digestible membrane) itself is designed to withstand the action of acid such as stomach acid, but it is also designed to be erodible. The orally ingestible delivery system loses its dispersible acid barrier when it encounters the duodenal environment. For example, if the dispersible acid barrier has been formed by a gas-producing substance, such as bicarbonate solids that generate carbon dioxide in the stomach, this gas (for example, carbon dioxide) provides mechanical protection while in the stomach. In the duodenum, however, the carbon dioxide is removed by the bicarbonate in the duodenum, thereby dispersing the mechanical protection that the carbon dioxide had provided while in the low-pH stomach environment. At this point, the acid-resistant shell is exposed to the action of the various enzymes in the duodenum, especially the proteases. The proteases may be capable of damaging the acid-resistant shell, and/or they may penetrate the acid resistant shell and attack the inner layers of the orally ingestible delivery system that surround the therapeutic agent(s).

Analogously, if the dispersible acid barrier has been formed by a space-occupying fluid or solid that is resistant to the activity of stomach fluids, the orally ingestible delivery system passes through the stomach relatively intact. The space-occupying fluid or solid has been selected to be dispersible within the duodenum: in other words, the activity of duodenal enzymes, bile salts, bicarbonate, etc., is intended to affect the space-occupying fluid or solid and lead to its dispersal. For example, a space-occupying non-polar fluid like an edible oil can be minimally affected by the stomach conditions, but can be emulsified by the bile salts in the duodenum, digested by the duodenal lipases, and/or destabilized by the pH change, so that it becomes dispersed. With the loss of the dispersible acid barrier, whether it had been provided by a fluid (liquid or gas) or a solid, the acid-resistant shell (for example, an acid resistant protease digestible membrane) is exposed on its outer surface to the digestive enzymes in the duodenum, which can begin to attack the protein components of this membrane. As described above, in addition to this external attack, the acid-resistant shell and underlying layers of the orally ingestible delivery system can be attacked from the inside.

The release of the therapeutic agent or therapeutic agent deliverable from the therapeutic agent compartment can commence when the pores of the acid-resistant shell (for example, an acid resistant protease digestible membrane) have been penetrated by the acid and have opened adequately. The process can accelerate as the acid-resistant shell decomposes and loses its integrity. The rate of disintegration of the acid-resistant shell can be controlled by engineering the structure of this membrane, as described in more detail below. Moreover, the therapeutic agent or agents within the therapeutic agent deliverable can be formulated so as to expedite or delay its/their release in active form, or to protect it/them from the action of digestive enzymes it/they encounter(s) in the duodenum after the enveloping acid-resistant shell has been breached. For example, a therapeutic agent can be formulated with protease inhibitors that would protect it from the action of proteases or slow their effect. As used herein, the term "inhibit" and related lexical units comprising this term refer to an action or process that hinders, restrains, slows, interferes with, or prevents another action or process. Other formulations are familiar in the art for delaying release within the intestinal tract. In other embodiments, the therapeutic agent within the therapeutic agent compartment can be surrounded by protective liquids or solid capsules that offer additional, engineered protection and/or that delay release within the intestinal tract. The therapeutic agent can be formulated as a solid, as a liquid, as a gel, or as a lyophilized preparation. In embodiments, the therapeutic agent can be a single agent (e.g., an active pharmaceutical ingredient ("API")) or a combination of agents (e.g., two or more APIs, or one or more APIs in combination with non-pharmaceutical substances intended to interact with the API(s) to enhance their efficacy, or a deposit of living organisms and their support milieu); such combinations can comprise the therapeutic agent deliverable.

3. Orally Ingestible Delivery Systems: General Structures for Acid-Resistant Shells In more detail, the acid-resistant shells (for example, an acid resistant protease digestible membrane) disclosed herein can be formed from confluent, continuous, or discontinuous component materials and any combination thereof. As one example, an acid-resistant shell can be formed homogeneously from a single acid-resistant substance. As has been shown in previous Figures, such a homogeneous acid-resistant shell can be penetrated by a series of pores blocked by a dispersible acid barrier, which pores would otherwise permit the access of stomach fluid through the acid-resistant shell to reach the therapeutic agent compartment. As another example, an acid-resistant shell can be formed from discontinuous acid-resistant elements that are placed in proximity to each other or in contiguity with each other, for example, a series of wax droplets that are added to each other to form a layer of adjacent, abutting or stacked particles having channels or interstices between the individual solid droplets. Solid elements can be stacked, woven, or placed next to each other, for example by a spraying process that disperses wax droplets to form a cobblestone-like layer or multilayer membrane. Channels between the discrete opposed elements form as the individual particles are deposited, which channels can allow gas or liquid to pass through the membrane in either direction (from inside to outside or from outside to inside). In embodiments, the acid-resistant shell formed from discontinuous elements can be formed of fibers that are stacked, air-laid, dry-laid, wet-laid, spun-melt, woven, or otherwise placed in proximity to each other, where the fibers are deposited in such a way as to leave channels or passages between, them that can allow gas or liquid to pass through. In embodiments, a net of fibers can be air-laid, and wax would be sprayed at the same time to bind or glue the network of fibers together. In an embodiment, a non-acid soluble fiber can be used, such as psyllium husk, cellulose fibers, lignin, and the like. In other embodiments, fibers are deposited in such a way that they are susceptible to dissolution, leaving channels or passages in the acid-resistant shell when the fibers are dissolved.

As previously described, barrier-forming substances can be deployed in the interstices in between elements of the acid-resistant shell, or within the elements of the acid-resistant shell, or both. In an embodiment, insoluble fibers can be used to form the acid-resistant shell, to be integrated with a substance like wax to provide more uniform resistance to acid. For example, in embodiments, acid-resistant or acid-dissolvable fibers can be stirred into melted wax to form a suspension, and the fiber-bearing wax suspension can then be formed into the acid-resistant shell layer. Alternatively, such fibers can be coated with wax or a similar substance before being used to for the network, or the fibers can be arranged in the network and subsequently sprayed or otherwise coated with wax or a similar substance.

In embodiments, barrier-forming substances can deployed within the wax layer or they can be attached to fibers bearing a wax coating. To form a suitable acid-resistant shell layer using this technique, the wax-coated fibers bearing the barrier-forming substances can be expected to adhere to each other without requiring separate gluing or other affixation technology. The wax coated fibers can also contain the barrier-forming substances embedded in the fibers themselves. For example, the fibers can simply be stirred into a solution of water and sodium bicarbonate, allowing the fibers to be soaked with water and dissolved sodium bicarbonate. The fibers can later be removed and dried, and the sodium bicarbonate crystals will reform within the fiber to act as barrier-forming substances. In other embodiments, wax can be used to coat acid-insoluble or acid-soluble fibers, which fibers can contain the barrier-forming substances. When the fibers dissolve, the barrier-forming substances produce barrier materials (for example, carbon dioxide gas) that then fills the spaces occupied by the fibers prior to their dissolution.

In an embodiment, fibers can be prepared for use in forming an acid-resistant shell layer by coating a selected type of fiber, for example an acid-insoluble fiber, with a layer of dissolvable gas-forming solids that are then covered by an outer layer of wax. If the outer layer of wax is penetrated, acid can access the layer of gas-forming solids (e.g., sodium bicarbonate), dissolving them, releasing gas (e.g., carbon dioxide), and leaving a void behind where the gas-forming solids previously resided. In another embodiment, a fiber can be combined with gas-forming solids or other solids, with the solids attached to the outside of the fiber or embedded or entrained within the fiber, or inserted into the acid-resistant shell in proximity to the fiber without being attached to or incorporated within it. If the fiber is acid-soluble, the fiber can be eroded upon contact with acid, during which process the fiber acts as a conduit to direct the acid to come into contact with the solids. Upon contact with the acid, gas-forming solids can release gas, which gas then occupies the space within which the fiber and the solids previously resided. In other words, the space initially occupied by the acid-soluble fiber and the solids becomes filled with gas, which then prevents further acid ingress. If the fiber is acid-resistant, with gas-forming or other solids attached to its outside or embedded or entrained within it, such a fiber can still act as a conduit to allow acid to come into contact with the solids: the acid can flow along the outer surface of the acid-resistant fiber (for example, by capillary action), so that it comes into contact with the solids in the vicinity. Upon contact with the acid, gas-forming solids can release gas, which gas then occupies the space within which the solids previously resided. While the acid-resistant fiber remains intact, the gas released from gas-forming solids occupies the space within which these solids previously resided. In embodiments, the gas-forming solids disposed in proximity to or within the fibers can be accompanied by starches or other materials capable of swelling upon contact with stomach acid. After contact with stomach acid, such swellable materials increase in volume and expand the space around them, potentially creating a larger volume within which the released gases can reside, and/or forming a more defined or more accessible channel for solids or gases or both.

Fibers, whether acid-resistant or acid-soluble, can act as conduits to stomach acid only when they come into contact with the acid. Therefore, the fibers in some way must come into contact with the acid. A number of ways can be envisioned by skilled artisans for providing this contact. For example, portions of fibers can be exposed on the outer aspect of the acid-resistant membrane, so that acid can contact those exposed portions. As another example, if the acid-resistant membrane is covered by a protease-digestible layer, the fibers are covered temporarily by that layer until it is digested; following the digestion of the protease-digestible layer, the fibers become exposed to stomach acid, allowing them to act as conduits. The presence of an outer layer covering the exposed portions of the fibers can be used to fine-tune the process of gas generation within the acid-resistant membrane. Similarly, layers internal to the acid-resistant membrane can be positioned so as to prevent further excursion of acid through this layer into the therapeutic agent compartment.

As another approach, channels of solids can be created within the acid-resistant shell by adding solid particles into a wax layer alone, or with water to be mixed in with a surfactant, or with a surfactant alone. As an example, starch and calcium carbonate powder can be mixed together, and a liquid surfactant can be added to create a paste. This paste can be added directly to the wax phase. Neither the starch nor the calcium carbonate powder dissolves, since it is only mixed in with surfactant and wax; these solids thus remain within the wax intact, subsequently allowing for the formation of channels as follows. After contact with stomach acid, the starch within the paste can dissolve and swell, thereby potentially expanding the space that it occupies and/or forming a more defined or more accessible channel for calcium carbonate; calcium carbonate from the original paste deposits can then react with the stomach acid to create a gas. This gas can now act as a barrier that is locked inside of the channels. Thereafter, upon contact with duodenal juice, the gas can be removed, exposing the channels to the internal area of the device. The starch as described above can be replaced by gelatin powder, pectin, xanthan gum, carrageenan, or any other hydrocolloid or material that may dissolve and swell when in contact with water or stomach acid. In addition, any liquid surfactant can be used to create a paste, or powdered surfactants can be used and simply mixed in with the other powdered materials and combined with the wax as well.

In embodiments, two or more different solids can be embedded in the matrix of the acid-resistant shell, with the different solids performing different functions. For example, one material can act as a gas-producing substance, as described below. A second material can interact with the gas bubbles that are formed to hold them in a particular location within the matrix, for example by surface tension attraction or other physical or chemical forces. A first gas-producing substance can be used that forms gas upon contact with the stomach fluid, and a second gas-producing substance can be used that forms gas only upon contact with the duodenal fluid. Other embodiments with varying arrangements of solids within the acid-resistant shell can be envisioned by practitioners of ordinary skill in the art.

In embodiments, the barrier-forming substances as described herein can be gas-producing substances. Of particular advantage is a gas-producing substance that generates carbon dioxide upon exposure to the hydrochloric acid in the stomach. Gas-producing substances (for example, carbon-dioxide formers such as calcium carbonate (including precipitated calcium carbonate (PCC)), sodium bicarbonate, potassium bicarbonate, magnesium carbonate, and other metal carbonates, and the like, or hydrogen formers such as magnesium particles and the like) exist as solid materials or in other physical states that can, in embodiments, be implanted in the acid-resistant shell or implanted in its pores, so that they release carbon dioxide or other gases when exposed to stomach acid. In an embodiment, the gas-producing substances can be embedded in a digestible polymer or small molecule matrix and intertwined with the wall-forming material of the acid-resistant shell, so that upon contact with stomach acid this matrix decomposes and exposes the embedded gas-producing substance to react with the stomach acid.

Carbon dioxide, as is produced by certain gas-producing substances, is particularly advantageous as the main component of the dispersible acid barrier because it dissolves in the neutral secretion of the intestine and reacts with the bicarbonates that are released into the duodenum via pancreatic secretions. This feature allows a carbon dioxide gas barrier that has been formed in the stomach by the action of the stomach acid on the gas-producing substance to be rapidly dispersed in the duodenum, allowing the ingress of the various pancreatic enzymes into the acid-resistant shell (for example, an acid resistant protease digestible membrane), as will be described below in more detail.

When the barrier-forming substances are gas-producing substances, they protect the orally ingestible capsule system from the effects of stomach acid: while the orally ingestible capsule system is in the stomach, fluids are prevented from accessing the acid-resistant shell (for example, an acid resistant protease digestible membrane) and from entering the pores by a dispersible acid barrier formed from a gas that covers the capsule system as a continuous layer or as a discontinuous layer, and/or that resides within the pores themselves. In either case, the dispersible acid barrier formed from the gas-producing substances creates a gas-fluid interface with the liquids in the stomach that prevents their entry into some or all of the pores. Some or all of the pore orifices on the surface of the membrane can be mechanically protected from fluid entry within the stomach by the dispersible acid barrier formed from the gas-producing substances, so that the stomach acid is unable to access the interior of the acid-resistant shell. When the dispersible acid barrier is formed from gas-producing substances, gas bubbles can also come to reside within the pore system as well or alternatively, forming discrete gas barriers within the pores themselves. While the gas bubbles are depicted in the Figures as discrete bubbles, it is understood that these gas bubbles can coalesce and occupy some of or substantially all of the space within the pores; this coalescence is to be anticipated, as the gas is formed from the gas-producing substances and expands within the pores. Gas within the pores therefore acts as a mechanical barrier to the incursion of stomach acid after the initial ingress of stomach acid causes the formation of gas from the gas-forming substances. Moreover, to the extent that the dispersible acid barrier formed from the gas-producing substances comes to reside on the surface of the acid-resistant shell, this barrier prevents stomach acid from contacting the external aspect of the membrane.

In other embodiments, the barrier-forming substances as described herein can be space-occupying solids or fluids (i.e., any fluid, whether gas or liquid) instead of, or in addition to, gas-producing substances. In embodiments, pores in the matrix can be partially or completely filled with solids and/or fluids that provide a mechanical barrier to the ingress of stomach acid. For example, the pores can contain a non-polar fluid in liquid form, such as an edible oil, that does not react to or dissolve in stomach acid, thereby blocking the stomach acid from entering the pores. Such a material would remain intact and in place as the orally ingestible delivery system traverses the stomach, but would be dispersible in the duodenum when the fluid is emulsified by the bile salts and subsequently dispersed. In embodiments, solids can be disposed within the pores instead of, or in addition to, the non-polar fluid. In embodiments, solids or liquids can add to the mechanical obstruction of acid inflow, and/or can be reactive with stomach acid to contribute to barrier formation. In embodiments, acid-reactive liquids or solids can interact with the stomach acid to form space-occupying materials that provide a mechanical barrier to the further incursion of stomach acid. For example, solid bicarbonate particles can be acid-reactive solids, interacting with the stomach acid to form carbon dioxide bubbles which in turn provide their own mechanical protection to the system, as described previously. As another example, a non-polar material such as a wax or a gel can act as a space-occupying solid, but it can be transformed into a space-occupying liquid at body temperature or upon exposure to the action of stomach acid or enzymes. A substance that forms another substance upon contact with acid is termed "an acid-reactive substance."

Certain of these embodiments (barrier-forming substances that are gas-producing substances, and barrier-forming substances that are space-occupying solids or fluids) are discussed below with reference to FIGS. 7-13. When the gas-producing substances (for example, bicarbonate crystals) encounter the stomach acid, they produce a gas (for example, carbon dioxide) that fills the pores and displaces the hydrochloric acid from the channels or pores. In embodiments, the gas can traverse the outer acid-resistant layer to reach the surface of the acid-resistant shell (for example, an acid resistant protease digestible membrane) to form a dispersible acid barrier thereupon. In other embodiments, the released gas can travel throughout the system of pores, completely or partially filling them, forming a dispersible acid barrier therein. In yet other embodiments, the released gas fills the pores more or less completely, as well as forming a gas layer on the surface. The gas in the pores and/or the gas layer on the surface (in certain cases, concentrated around the external orifices of the pores or channels) prevents further incursion of stomach acid into the outer acid-resistant layer, thereby protecting the inner erodible layer from contact with gastric juice.

In embodiments, the acid-resistant shell (for example, an acid resistant protease digestible membrane) contains channels or pores that allow stomach acid to reach the gas-producing substances entrained therein, and further allows the gas or gases released from the gas-producing substances to reach the surface. In embodiments, the acid-resistant shell (for example, an acid resistant protease digestible membrane) can be formed with gas-producing substances embedded therein that creates pores upon the activation of the gas-producing substances; alternatively, or in addition, its pores can be created mechanically. Forming the channels or pores mechanically can involve puncturing the layer, for example with microneedles after it has been deposited, so that there is a direct pathway created that allows stomach acid to enter the layer and reach at least some of the gas-producing substances disposed therein. In embodiments, the porous structure of the acid-resistant shell can be produced via 3-D printing or other technologies that simultaneously form the voids and the solid areas of the matrix so that a porous network is formed within the matrix. In other embodiments, the acid-resistant shell can be formed with gas-producing substances embedded therein, and then its pores can be created chemically. For example, forming the channels or pores chemically can occur if there are acid-digestible elongate structures like filaments or fibers dispersed within the layer, which elongate structures are eroded or digested by stomach acid, leaving behind voids through which the stomach acid can infiltrate the layer. For example, the acid-resistant shell can be formed with gas-producing substances embedded therein and hydrophilic substances (fibers or other inclusions, polymers, etc.) dispersed throughout the matrix, so that the hydrophilic substances can offer conduits for stomach acid to enter the matrix and react with the gas producing substances; in embodiments, the hydrophilic substances are selected so that they are hydrolysable by the stomach acid, producing voids in the matrix that allows the gases produced by the gas-producing substances to exit the matrix and form the dispersible acid barrier on the surface of the acid-resistant shell, as described above.

In embodiments, the differentially permeable (for example, digestible) capsule system can be formed as a single layer enclosing the therapeutic agent compartment but having asymmetrical properties. If the properties of such a single-layer structure include both acid resistance and protease digestibility, the structure may be deemed an acid-resistant protease-digestible membrane. For example, such a layer can include a naturally derived polymer such as gelatin or an engineered polymeric matrix having embedded space-occupying solids or fluids, or gas-producing substances such as bicarbonate crystals within it, using techniques as described above. The layer can then be formed as a gradient with a more hydrophobic, acid-resistant outer region and an inner, more hydrophilic inner region. For example, the layer can include more of the waxy or hydrophobic polymer in the mixture on the outer region, and a more protein-based or hydrophilic polymer in the mixture on the inner region. In embodiments, an asymmetrical layer can be formed using temperature gradients that produce a gradient of two dissimilar components in the layer. In embodiments, an asymmetric layer can be formed by temperature gradients. The layer is placed between two layers of dissimilar temperature. Between the two temperature boundaries there will be a temperature as a function of position within the bulk layer, and any slice within the bulk layer has a tiny layer of a temperature $T(z)$. The preferred mixing distribution of two dissimilar components is a function of the temperature. This means that as $T(z)$ is different for each layer at z the mixing of components C1 and C2 is different than at other z positions, so that throughout the finite thickness bulk layer at positions z along the thickness there will be different mixing ratios of C1 and C2. When the layer then is "frozen" in place by gradual cooling, the z-dependent mixing ratios will remain, so the mixing C1 and C2 is not uniform throughout.

In embodiments, one-layer differentially permeable (for example, digestible) capsule systems can be fabricated having a combination of properties, for example behaving like systems having an outer acid-resistant shell and an inner erodible layer. A single blended layer comprising an erodible material and an acid-resistant material (for example, gelatin and a waxy matrix) can be formed with the two components blended together, and with space-occupying fluids or solids, or gas-producing substances disposed therein. Digestion of the erodible material by stomach acid forms channels that allow the acid to access the barrier-forming substances and activate or release them. As the gas is produced from a gas-producing substance, or the space-occupying fluid is released from its deposit, it fills the channels and optionally reaches the surface of the layer to produce an inner and outer dispersible acid barrier, as described previously. Alternatively, or in addition, a gas-producing layer and/or a layer of space-occupying fluid can be disposed on the interior of the single blended layer, so that gas is produced or fluid is released, respectively, by the barrier-forming layer when it is reached by the stomach acid that erodes through the erodible portions of the single blended layer. Reinforcing materials, described in more detail herein, can be added to the single blended layer to add strength and/or resilience.

In embodiments, for example, a one-layer differentially permeable (for example, digestible) capsule system can be formed from a mixture of a water-swellable, acid-hydrolysable and/or protease-digestible phase, and a water-resistant and hydrolysis-resistant phase; this one-layer system encloses a therapeutic agent or a therapeutic agent deliverable. In embodiments, the water-swellable acid-hydrolysable and/or protease-digestible phase can comprise polysaccharides, proteins, or some combination thereof. Polysaccharides familiar in the art, such as starch (tapioca, rice, and corn, etc.), glycogen, inulin, pectin, xanthan gum, carrageenan, gum Arabic, agar, alginate, and the like can be used for this phase. In embodiments, polysaccharides having hydrocolloidal properties may be selected in order to exploit their ability to swell upon exposure to water. Proteins such as gelatin, wheat gluten, corn zein, soy protein, whey protein, and mung bean protein, can be used for this phase, and can form water-swellable protein solutions. Gas-producing substances or space-occupying fluids can be dispersed within this phase, analogously to the distribution of such substances as otherwise described herein. The water-insoluble, acid-resistant phase can be formed from a variety of substances, for example cellulose, fatty acids, waxes, polyolefins, edible/natural elastomers (such as natural latexes, couma macrocarpa, tunu, jelutong, or chicle). This water-insoluble, acid-resistant phase can also comprise non-digestible food-grade materials such as fibers intended to improve the strength and durability of this layer.

Figure 7:
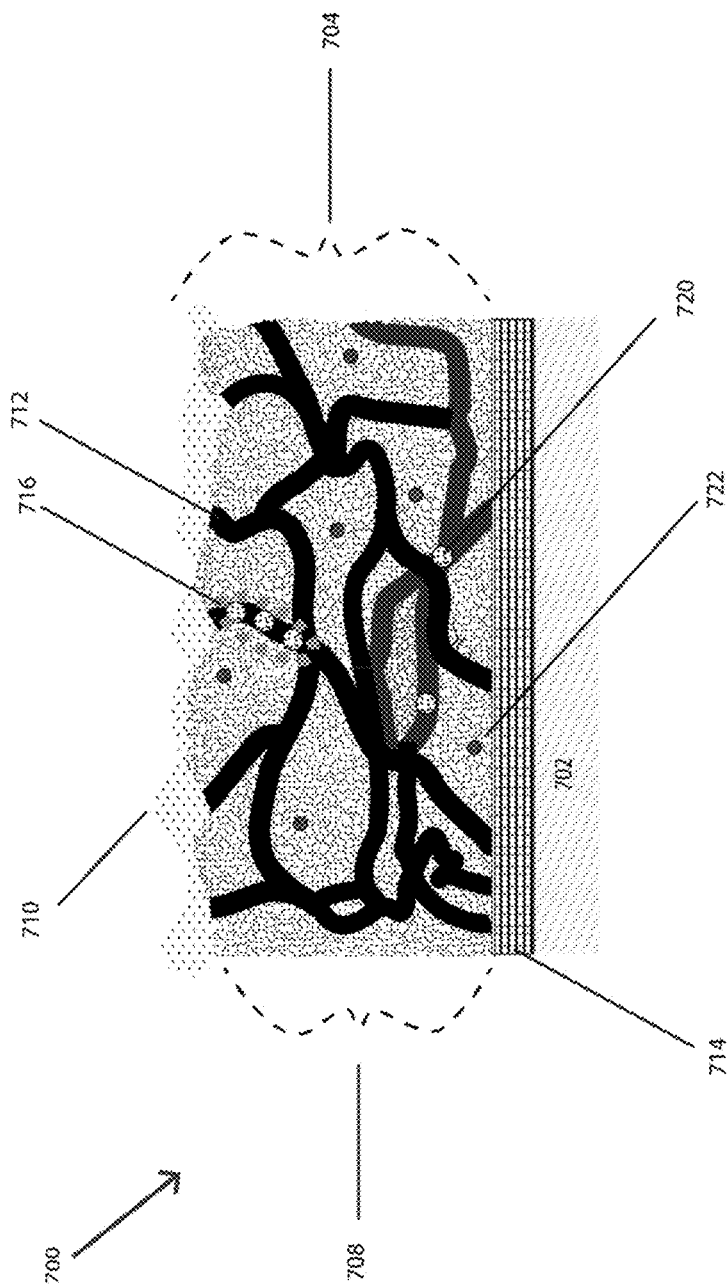
FIG. 7 depicts schematically a segment of an embodiment of an orally ingestible delivery system in cross-section.

FIG. 7 depicts an embodiment of the orally ingestible delivery system 700 illustrating schematically an external dispersible acid barrier 710 comprising gas bubbles that is on the surface of the acid-resistant shell 708 (for example, an acid resistant protease digestible membrane) formed by the mechanism using gas-producing barrier-forming substances as described above, and an inner dispersible acid barrier 716 formed within the system of pores 712 by the same mechanism. The orally ingestible delivery system 700 shown in this Figure has been exposed to stomach acid during a period of residence in the stomach. As a result, the gas-producing substances (not shown) originally dispersed within the system of pores 712 have reacted in whole or in part with the stomach acid to produce gas bubbles 720 within the system of pores 712 that occupy and block up the system of pores 712 to form the inner dispersible acid barrier 716 (shown schematically in this Figure as a linear arrangement of three gas bubbles within the system of pores, although it is understood that this inner dispersible acid barrier 716 can be designed to fill all or substantially all of the pores to provide more adequate barrier effect). As is described below in more detail, the gas bubbles 720 within the system of pores 712 can coalesce to form a robust inner dispersible acid barrier 716; moreover, gas bubbles 720 can traverse the system of pores 712 to reach the surface of the acid-resistant shell 708, where the gas bubbles form the external dispersible acid barrier 710. While only a few gas bubbles 720 are shown in this Figure, it is understood that a plurality of gas bubbles can be produced, occupying partially or fully the system of pores 712 and thereby obstructing the system of pores 712 sufficiently to provide an inner dispersible acid barrier 716. In embodiments, unreacted deposits of gas-producing substances 722 can remain within the matrix of the acid-resistant shell 708, or within the system of pores 712 (not shown); in other embodiments, there are no unreacted deposits of gas-producing substances within the system of pores 712, because these gas-producing substances have all reacted to produce gas bubbles 720.

As depicted in FIG. 7, the acid-resistant shell 708 can be used in conjunction with an inner erodible layer 714, disposed interiorly, with a therapeutic agent compartment 702 positioned internal to the inner erodible layer 714, effectively producing a two-layer differentially permeable (for example, digestible) capsule system; when the inner erodible layer 714 is protease-digestible, the combination of the acid-resistant shell 708 and the inner erodible layer 714 forms an acid-resistant protease-digestible membrane. In a two-layer differentially permeable capsule system, as in the depicted embodiment, the inner erodible layer 714 is protected from the action of the gastric juice by the gas bubbles 720 that form within the pores and/or the protective effect of the external dispersible acid barrier 710. In embodiments, not shown in this Figure, the erodible layer 714 can contain barrier-forming substances, such as the gas-producing substances depicted within the acid-resistant shell 708. In other embodiments, not as depicted in this Figure, the acid-resistant shell can be formed as a single layer that bears within its matrix a similar system of pores, but unassociated with an inner erodible layer 714. In yet other embodiments, the acid-resistant shell 708 includes within itself or is combined with other layers to impart other advantageous properties. For example a layer can be added to increase mechanical strength or stability, containing for example embedded biodegradable structural supports such as fibers or an internal meshwork to add to its strength, or an embedded biodegradable layer containing additional barrier-forming substances that can react when exposed to conditions in the stomach or the intestine, or an external layer to be digested or dispersed in the stomach that affords mechanical protection during passage through the mouth and esophagus. In other embodiments, an external layer can be provided on top of the acid-resistant shell 708 in the form of a network or mesh of elastomeric fibers that cushion and protect the capsule as it is buffeted by stomach peristalsis. Other such layers at any level of the acid-resistant shell (above, below, or within) can be envisioned by skilled artisans.

As depicted in FIG. 7, some of the gas bubbles 720 produced by the contact of the stomach acid with the deposits of gas-producing substance remain within the system of pores 712 (thereby forming the inner dispersible acid barrier 716), while other gas bubbles 720 exit the system of pores to form the external dispersible acid barrier 710 that resides on the surface of the acid-resistant shell 708 (for example, an acid resistant protease digestible membrane). As used herein, the term "dispersible acid barrier" includes the external dispersible acid barrier 710 that is disposed on the external aspect of the acid-resistant shell 708, and further includes any single or confluent gas bubbles 720 or other dispersible barrier substances that reside within the system of pores 712 (i.e., the inner dispersible acid barrier 716). In the depicted embodiment, both the outer dispersible acid barrier 710 and the gas bubbles 720 within the pores 712 (i.e., the inner dispersible acid barrier 716) act to protect the acid-resistant shell 708 and the therapeutic agent payload (not shown) encased by the differentially permeable (for example, digestible) capsule system 704 from contact with and action of stomach acid and stomach enzymes; furthermore, both the outer dispersible acid barrier 710 and the gas bubbles 720 residing within the pores are dispersible by action of bicarbonate in the duodenum and by dissolving into the non-acidic intestinal fluids, as described below in more detail. While the gas bubbles 720 in this Figure and other Figures are shown as discrete bubbles, it is understood that the gas bubbles 720 can coalesce and occupy some of or substantially all of the space within the pores; this coalescence is to be anticipated, as the gas is released from the gas-producing substances and expands within the pores 712.

As illustrated schematically in this Figure, the acid-resistant shell 708 (for example, an acid resistant protease digestible membrane) can provide or be formed with an irregular surface (irregularly or regularly irregular, with grooves, pits, corrugations, and the like), and the outer dispersible acid barrier 710 arranges itself along the outer aspect of the acid-resistant shell 708 in an irregular manner, for example with more gas bubbles contained in the pits or depressions of the acid-resistant shell 708 surface, thereby leading to an irregular or even discontinuous outer aspect to the dispersible acid barrier 710 itself. The irregular surface can be formed during the period of residence in the stomach, as the stomach acid produces gas bubbles that can distort the shape of the matrix that contains or supports them. In embodiments, digestion or deterioration of the acid-resistant shell 708 can lead to the alteration of its surface, so that it becomes irregular. Regardless of how formed, irregularities of the outer dispersible acid barrier interface can increase the hydrophobicity of the outer dispersible acid barrier 710 and enhance its ability to repel liquids such as gastric juice. In certain embodiments, the acid-resistant shell 708 can be formed with a regular surface. In such embodiments, while the surface configuration may not assist with the formation and retention of the outer dispersible acid barrier 710, the protective effect of the inner dispersible acid barrier 716 can suffice to insulate the underlying inner erodible layer 714 and underlying therapeutic agent compartment 702 from attack by stomach acid. In other embodiments, the features of the surface configuration can be selected so that they assist with the formation and the retention of the outer dispersible acid barrier. In certain embodiments, the regular properties of the surface can assist with the formation and retention of the outer dispersible acid barrier.

Figure 8:
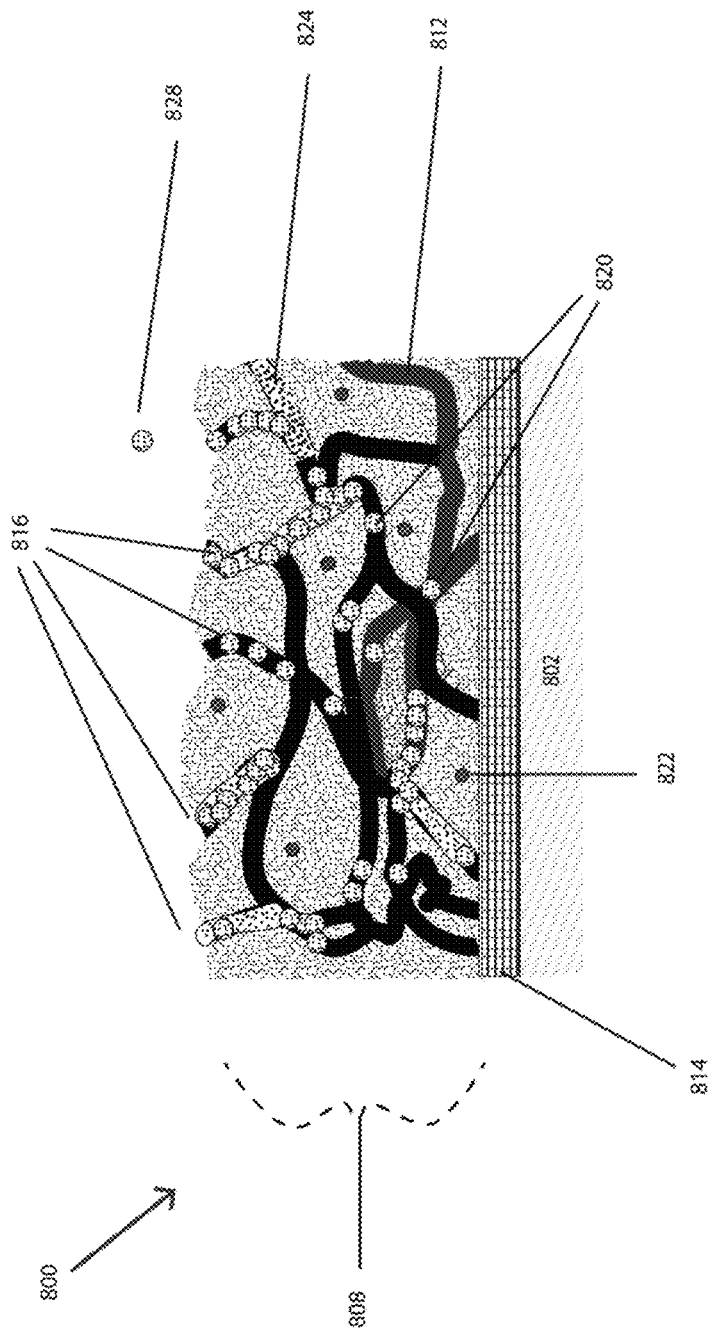
FIG. 8 depicts schematically a segment of an embodiment of an orally ingestible delivery system in cross-section.

FIG. 8 shows schematically an embodiment illustrating in more detail the formation of the inner dispersible acid barrier 816. As shown in this Figure, an orally ingestible delivery system 800 comprises an acid-resistant shell 808 (for example, an acid resistant protease digestible membrane) and a therapeutic agent compartment 802. There is an inner protease digestible layer 814 deployed inside the acid-resistant shell 808. As has been previously described, structures for the differentially permeable (for example, digestible) capsule system comprising the acid-resistant shell 808 can include a single-layer construction, two-layer construction, or a multiple-layer construction. In the depicted embodiment, the acid-resistant outer layer 818 of the acid-resistant shell 808 is penetrated by a system of pores 812. The system of pores 812 is filled with gas, shown here as individual gas bubbles 820 and also as coalesced gas bubbles 824. The effect of the gas within the system of pores 812 is to produce an inner dispersible acid barrier 816 preventing the ingress of fluid from the external environment. As has been previously described, the acid-resistant shell 808 can be originally formed having a system of pores 812 within which gas-producing substances have been disposed (not shown); in embodiments, gas-producing substances 822 can also be disposed within the matrix of the outer acid-resistant layer 818 of the acid-resistant shell 808, and/or at other designated locations. In the depicted embodiment, the portions of system of pores 812 have become filled with gas that has been formed by the interaction of the gas-forming substances within the pores with stomach acid. The gas bubbles 820 thus produced occupy the pores in whole or in part and can coalesce 824, producing the inner dispersible acid barrier 816 that prevents the further ingress of stomach juices. While the gas bubbles 820 and coalesced gas 824 are shown in this Figure as occupying only a portion of the system of pores 812, the orally ingestible delivery system 800 can be engineered to produce greater or lesser degrees of pore filling. The Figure represents a combination of empty pores, pores filled with gas bubbles 820, and coalesced gas 824, but these depictions are merely illustrative. The inner dispersible acid barrier 816 can include any combination of fully gas-filled pores, partially gas-filled pores, pores filled with coalesced gas bubbles, and pores containing discrete gas bubbles; moreover, the behavior of the gas within the pores can be dynamic, depending on the mechanics of bubble formation and the transit of the bubbles through the system of pores 812.

Without being bound by theory, it is understood that the surface tension of the gas itself allows the gas to remain within the pores 812 as a durable barrier to the entry of stomach juices. In embodiments, the gas contents of the system of pores can escape the pores 812 and be released into the surrounding stomach as released gas bubbles 828. In other embodiments, as depicted in previous Figures for example, gas bubbles can be retained on the surface of the acid-resistant shell 808 (for example, an acid resistant protease digestible membrane) to form an outer dispersible acid barrier (not shown) that operates synergistically with the inner dispersible acid barrier 816 depicted in this Figure. In embodiments, the inner dispersible acid barrier 816 provides the sole or the main protection preventing incursion of stomach juices into the system 800, which would result in subsequent digestion of the inner erodible membrane 812. In the depicted embodiment, an outer dispersible acid barrier is absent; in other embodiments it is optional, as an adjunct or alternative to the functioning of the inner dispersible acid barrier 816. The presence of the outer dispersible acid barrier and its relationship to the inner dispersible acid barrier is illustrated in other Figures.

Alternative mechanisms are available for producing dispersible acid barriers comprising a gaseous mechanical barrier for use with the orally ingestible delivery system as described herein; non-limiting examples are provided herein to illustrate useful mechanisms. As an example, an emulsion containing a bicarbonate solution can be sprayed or otherwise disposed on the surface of the acid-resistant shell (for example, an acid resistant protease digestible membrane) during its manufacture under conditions that would then allow the water in the bicarbonate solution to evaporate, thereby leaving bicarbonate crystals embedded in the emulsion layer on the surface of the acid-resistant shell. On contact with stomach acid, the bicarbonate crystals can then react to form carbon dioxide, which can come to reside in the indentations or irregularities on the acid-resistant shell surface, thereby producing the external dispersible acid barrier. As another example, pores may be punctured in a hydrophobic layer by mechanical means (such as needles, pins, and the like), resulting in a non-intersecting system of pores, channels, indentations, or the like. In embodiments, pores can have bicarbonate deposited in them, for example by dipping the layer in a bicarbonate solution and allowing the solvent to dry. Further mechanisms for forming the gas-based dispersible acid barrier can be envisioned by practitioners of ordinary skill in the relevant arts.

As has been previously described, barrier-forming substances such as gas-forming substances 822 can be deployed within, beneath, or on top of a separate erodible layer 814. Barrier-forming substances in such a layer can react upon encounter with stomach or intestinal fluids to form or to add to the inner dispersible acid barrier 816.

Figure 9:
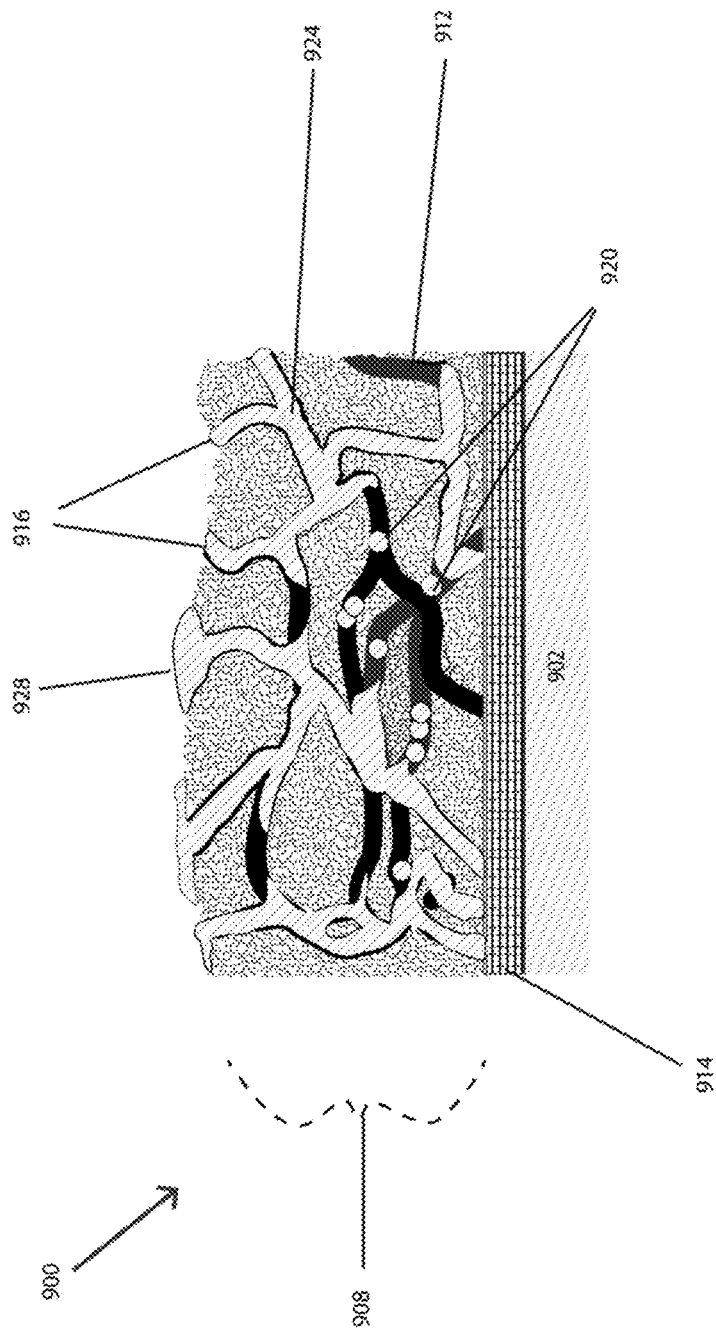
FIG. 9 depicts schematically a segment of an embodiment of an orally ingestible delivery system in cross-section.

As mentioned above, in embodiments, the barrier-forming substances described herein can comprise space-occupying solids or fluids instead of, or in addition to, gas-producing substances. FIG. 9 depicts an illustrative embodiment. In FIG. 9, an orally ingestible delivery system 900 comprises an acid-resistant shell 908 (for example, an acid resistant protease digestible membrane) and a therapeutic agent compartment 902. As has been previously described, structures for the acid-resistant shell 908 can include a single-layer construction, two-layer construction, or a multiple-layer construction. In the depicted embodiment, there is an inner erodible layer 914 deployed inside the acid-resistant shell 908, enclosing the therapeutic agent compartment 902, similar to those arrangements disclosed previously; if the inner erodible layer 914 is protease-digestible, its combination with the acid-resistant shell 908 forms an acid-resistant protease-digestible membrane. The acid-resistant shell 908 is penetrated by a system of pores 912 within which is a space-occupying fluid, here shown schematically as individual fluid droplets 920 and as a confluent layer of space-occupying fluid 924 (which can be formed from coalesced fluid droplets) that can block the pores 912. The space-occupying fluid droplets 920 and/or layers 924 in the pores 912 provide a mechanical barrier to the ingress of stomach fluid, thus constituting an internal or inner dispersible acid barrier, shown schematically as 916. While the depicted embodiment lacks a completely-formed outer dispersible acid barrier, such a barrier can be formed in other embodiments, for example if there is confluence of the space-occupying fluid on the surface of the outer acid-resistant layer 918; such a partial confluence is illustrated schematically as 928. In the depicted embodiment, the presence of the partially confluent outer acid-resistant layer 928 can suffice to provide an adequate barrier to the ingress of stomach fluid. In the depicted embodiment, the space-occupying fluid only partially fills the pores 912, but sufficiently so to block the entry of stomach fluid. In other embodiments, the space-occupying fluid can fill the pores completely, or to any level sufficient to provide a partial or complete mechanical blockage to the inflow of the external stomach fluid. While the pores 912 in the depicted embodiment are shown to be convoluted and intersecting, it is understood that pores 912 can be configured in any arrangement that permits the ultimate access of external digestive fluids (whether from the stomach or the intestine) into the therapeutic agent compartment 902, as has been previously described. For example, the pores can be straight, curved, branching, intersecting, networked, lattice-like, or of any other shape or configuration, and the network of pores can contain blind pockets or closed-off channels that do not connect in whole or in part to the rest of the network.

In an embodiment, the pores 912 can be filled in whole or in part with a liquid that is resistant to the action of stomach acid, for example, a non-polar edible oil. In embodiments, an optional protective layer (not shown) can be deployed on the outer aspect of the orally ingestible delivery system 900 that would encase the entire system and retain the space-occupying fluid within the system of pores 912 prior to ingestion; the protective layer is intended to be sacrificial, i.e., dissolving in whole or in part upon encounter with the stomach fluids. Thus, when the orally ingestible delivery system 900 enters the stomach, the outer coating can dissolve quickly, exposing the surface of the acid-resistant shell 908 (for example, an acid resistant protease digestible membrane) and the openings of the pores 912 within which the space-occupying fluid 920 and 924 resides. Within the stomach, however, the space-occupying fluid 920 and 924 would remain substantially within the pores 912, due to surface tension factors and/or polarity differences between the stomach contents and the liquids within the channels. The fluid within the pores provides the barrier preventing the ingress of stomach fluids and preventing their access to the optional inner erodible layer 914, thus constituting an inner dispersible acid barrier, shown schematically as 916. In certain embodiments, the space-occupying fluid within the channels can extravasate, to form a fluid layer 928 on the surface of the acid-resistant shell 908. This external fluid extravasation 928 can remain localized around the outer openings of the pores as depicted, or can become partially or completely confluent, forming an outer dispersible acid barrier (not shown) that can supplement the protection offered by the inner dispersible acid barrier 916.

Dispersion of the outer dispersible acid barrier (which is represented in this Figure only by the partially confluence 928 overlying the pores) and the inner dispersible acid barrier 916 takes place when the orally ingestible delivery system 900 enters the duodenum and encounters the bile salts and lipases therein. In embodiments, when the space-occupying fluid in the pores 912 (and optionally on the surface 928) encounters the bile salts and lipases, the fluid itself can be digested and/or emulsified. An advantageous feature of certain space-occupying fluids is their susceptibility to emulsification and/or digestion by the bile salts and lipases found in the duodenum; these agents can act on the fluid and emulsify it or digest it to form smaller droplets, thus permitting the dispersal of the fluid and the consequent dispersal of the dispersible acid barrier that the fluid forms. In more detail, once the orally ingestible delivery system 900 enters the duodenum and is exposed to a more neutral pH environment containing lipase and bile salts, the liquid in the pores 912 will be emulsified into droplets and removed from the pores 912. With the dispersion of the space-occupying fluid, the mechanical barrier dissipates, and the proteases in the duodenal fluids have direct access through the pores to the therapeutic agent compartment 902 either immediately or following digestion of the optional inner erodible layer 914. Furthermore, the duodenal proteases have access to the matrix of the acid-resistant shell 908 from within the system of pores 912 as well as from the outer surface of the acid-resistant shell 908. This internal access provides a much larger exposed surface area for the action of intestinal proteases, thereby facilitating the destruction of a protease-susceptible acid-resistant shell 908 with subsequent release of the therapeutic agent from the therapeutic agent compartment 902.

In embodiments, surfactants can be pre-loaded into the liquid phase when the inner dispersible acid barrier 916 is prepared. In other embodiments, a liquid surfactant can be spread on top of the inner erodible layer 914, or on the undersurface of the acid-resistant shell 908 (for example, an acid resistant protease digestible membrane), or both. Surfactants can be added to either the acid-resistant shell or the inner erodible layer as they are depicted in this FIG. 9 or in other Figures, recognizing that surfactants can improve adhesion between these layers. Surfactants can be used in powder or liquid form. They can be applied in any manner familiar to skilled artisans, for example, by being stirred into a molten phase of a layer as it is being formed, or by being sprayed or spread onto a formed sheet. Advantageously, the surfactants used for these purposes can be pH sensitive, so that they are active at the pH of the duodenum and not active at the pH of the stomach, thereby preventing them from contributing to emulsification of the inner dispersible acid barrier 916 in the stomach.

Examples of useful surfactants include zwitterionic or amphoteric surfactants, such as betaines or those that have a phosphate anion with an amine or ammonium, such as the phospholipids phosphatidylserine, phosphatidylcholine, and sphingomyelins. If the surfactant within the inner dispersible acid barrier 916 can be protected from exposure to the pH of the stomach, any surfactant can be used, independent of its pH sensitivity, for example, high HLB surfactants capable of forming oil-in-water emulsions, such as proteins, phospholipids, potassium and sodium salts, alginates, diacetyl tartaric acid esters of monoglyceride, lecithin, ethoxylated monoglyceride, and the like. Mixtures or combinations of surfactants can be used advantageously, and different surfactants can be used in different layers. For example, if charged surfactants are being used, an anionic surfactant can be used for one layer and a cationic surfactant can be used for the other layer.

In embodiments, the space-occupying fluid can be delivered directly into the pores 912 via mechanisms known in the art, such as forming the pores in the acid-resistant shell 908 (for example, an acid resistant protease digestible membrane) and then immersing this membrane in the space-occupying fluid under sufficient pressure that the fluid enters into the pores and displaces whatever the pores contained previously. For example, a less dense fluid can be initially deployed within the pores, and then this fluid can be displaced by the denser oil-based fluid that will constitute the space-occupying fluid in the final system when the therapeutic agent is enveloped by the acid-resistant shell 908. Alternatively, the acid-resistant shell 908 matrix and/or its pores can be packed with a gas-forming substance such as sodium bicarbonate that can be preliminarily removed by exposure to a weak acid, such as citric acid or acetic acid; in other embodiments, a salt or sugar can be introduced into the pores and dissolved out with water. In these situations, the residual gas or water can be centrifuged out, leaving behind empty channels (i.e., pores 912) into which the oil-based fluid can be delivered. In other embodiments, the space-occupying fluid can be injected into an intact acid-resistant shell 908, thereby forming the pores 912 and simultaneously introducing the space-occupying fluid.

An optional sacrificial top coating (not shown) can be placed external to the acid-resistant shell 908 that initially restrains the fluid within the pores 912 and protects the entire system 900 from mechanical trauma. This outermost layer can be any protease-digestible or acid-digestible material that can be eroded within the stomach, so that the space-occupying fluid is initially restrained within the pores 912 but then is exposed to the environment as the outermost layer itself is sacrificed. In other embodiments, an optional non-sacrificial coating can be placed external to the acid-resistant shell 908 that partially protects the entire system 900 from exposure to stomach fluids but that is susceptible to digestion in the duodenum: such a non-sacrificial coating can be pH sensitive, for example, so that it retains its integrity in an acid environment like the stomach but it is digested or dissolved in the neutral or basic environment of the intestinal tract.

Space-occupying fluids useful for forming the inner dispersible acid barrier 916 are those that are resistant to stomach fluids (acid and/or proteases in the acid environment), but that are susceptible to the activity of digestive substances found more distally in the intestine (including bile salts, lipases, proteases, all as are deployed within a neutral or basic environment), or that are pH sensitive so that their integrity is affected by the pH in the intestinal tract.

Advantageously, the space-occupying fluid is a non-polar material such as an edible oil, that can be easily emulsified and that would separate from stomach acid. As examples, materials such as triglycerides, fatty acids, and esters derived from vegetable oils or plant materials are useful as space-occupying fluids. In embodiments, medium chain fatty acids are desirable. Exemplary edible oils containing medium chain fatty acids include coconut oil, MCT oil, palm kernel oil, laurel oil, and other oils containing caproic acid, caprylic acid, capric acid, or lauric acid. Useful materials also include triglycerides and esters produced from edible oils, for example caprylic and capric acid ester products such as CAPTEX® products, NEOBEE® products, MIGLYOL® products, and the like. Other edible oils, including long or short chain fatty acids, can also be used, such as olive oil, palm oil, soybean oil, canola oil, corn oil, peanut oil, avocado oil, mustard oil, rice bran oil, safflower oil, sesame oil, sunflower oil, almond oil, flaxseed oil, cottonseed oil, grapeseed oil, butter, margarine lard, linseed oil, hemp oil, macadamia oil, pumpkin seed oil, walnut oil, tallow, tea seed oil, hazelnut oil, acai palm oil, jambu oil, graviola oil, tucuma oil, brazil nut oil, carapa oil, buriti oil, passion fruit oil, pracaxi oil, solarium oil, cocoa butter oil, pecan oil, perilla oil, vitamin A oil, vitamin E oil, cod liver oil, shark liver oil, krill oil, or fish oil from fish such as herring, sardines, tuna, anchovies, mackerel, and salmon, and the like. In embodiments, the space-occupying fluid can itself contain therapeutic agents, which would be released with the dispersal of the fluid in the intestine.

In embodiments, the space-occupying fluid can be introduced into the pores as a liquid, as described above. In other embodiments, the space-occupying fluid is a fat or an oil that is thermally sensitive, so that it is a liquid when it is introduced into the pores, but so that it solidifies as the system cools; such a material may solidify at room temperature, for example, and re-liquify at body temperature, or it may solidify as it cools and remain a solid at body temperature. Such a material would be a hybrid space-occupier: a fluid at certain temperatures and a solid at others, offering mechanical protection in either case.

In embodiments, the space-occupying fluid can be introduced into the pores via encapsulation. The fluid can be a non-polar material as described above, but it can be introduced into the pores encased in microcapsules that are dimensionally adapted to fit within the pores. Microcapsules can be sized in any dimension to fit within the pores, for example, at sizes ranging from about 0.3 microns to about 10 microns in diameter.

Figure 10:
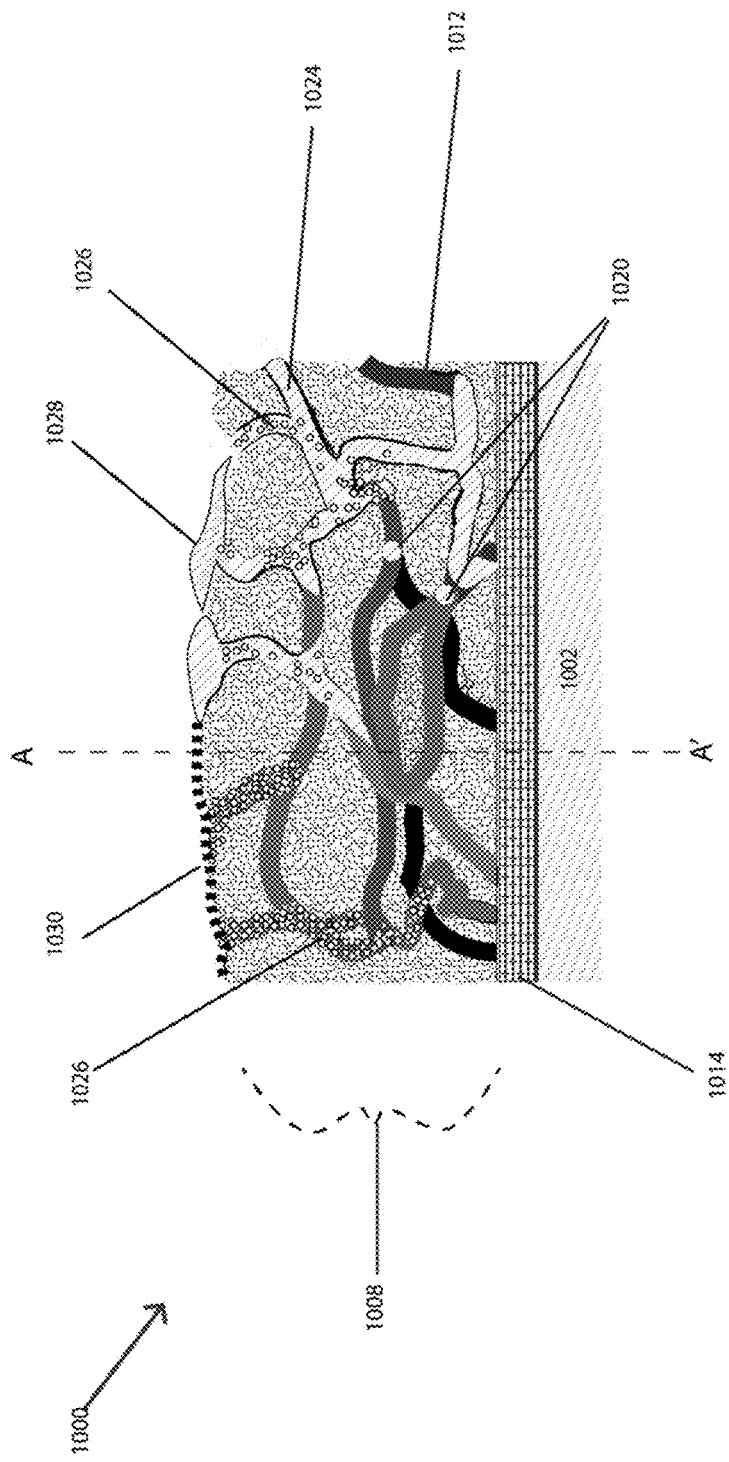
FIG. 10 depicts schematically a segment of an embodiment of an orally ingestible delivery system in cross-section.

A representative embodiment is depicted in FIG. 10. As shown in this Figure, an orally ingestible delivery system 1000 includes an acid-resistant shell 1008 (for example, an acid resistant protease digestible membrane), similar to those described previously, and a therapeutic agent compartment 1002. As has been previously described, structures for the acid-resistant shell 1008 can include a single-layer construction, or a multiple-layer construction. In the depicted embodiment, there is an optional inner erodible layer 1014 deployed inside the acid-resistant shell 1008, enclosing the therapeutic agent compartment 1002, similar to those arrangements disclosed previously. As was described for previous Figures, if the inner erodible layer 1014 is protease-digestible, its combination with the acid-resistant shell 1008 forms an acid-resistant protease-digestible membrane. Dispersed throughout the outer acid-resistant layer is a system of pores 1012. As shown in the Figure, to the left of the dotted line A-A', the system of pores is packed with a plurality of microcapsules 1026. This section of the Figure represents the status of the system's dispersible acid barrier when the orally ingestible delivery system 1000 is initially ingested. As shown in FIG. 10, a sacrificial coating 1030 covers the external aspect of the orally ingestible delivery system 1000 on the left-hand side of the dotted line A-A'; as shown, the sacrificial coating 1030 can protect the microcapsules 1026 before entry into the stomach, for example during storage conditions, and/or can initially protect the microcapsules 1026 from initial exposure to stomach fluids upon entry into the stomach. As previously described, the stomach fluids can erode the sacrificial coating 1030, thus exposing the microcapsules 1026 to the acid and proteases in the stomach. The walls of the microcapsules 1026 can be formed from a material such as gelatin that can be eroded by the acid and/or proteases in the stomach, thereby releasing the contents of the microcapsules to become the space-occupying fluid 1024 or 1020. This situation is represented in the Figure on the right-hand side of the dotted line A-A', where the sacrificial coating has been eroded and some of the microcapsules 1026 have ruptured, releasing their fluid contents as a confluent fluid layer 1024 and/or as fluid bubbles 1020 within the system of pores. As shown on the right-hand side of the dotted line A-A', some of the confluent fluid layer 1024 has extravasated from the pores 1012 to reside on the surface of the orally ingestible delivery system 1000; this extravasated material 1028 can remain localized over the pore orifices, or can itself become confluent, thereby forming an outer dispersible acid barrier that supplements or supplants the inner dispersible acid barrier formed by the space-occupying fluid. In other embodiments, the sacrificial coating 1030 can be non-sacrificial, intended to remain at least partially intact until the orally ingestible delivery system reaches the intestinal tract, as described above. In yet other embodiments, the sacrificial coating 1030 is optional; in these cases, the microcapsules 1026 are positioned within the system of pores 1012 so that they remain substantially within the pores 1012 as the system enters the stomach, becoming dissolved within the stomach to release their contents in gas or liquid form within the pores during the passage of the device through the stomach and/or in the intestine. In embodiments, the microcapsules 1026 are packed tightly enough that they form themselves a mechanical barrier: these structures thus act as space-occupying solids until they dissolve to release their fluid contents.

The microcapsules 1026 illustrated in FIG. 10 are one example of space-occupying solids that can form mechanical barriers within the pores to prevent the ingress of stomach fluids. Other space-occupying solids can perform the same function, as shown below in FIG. 11.

Figure 11:
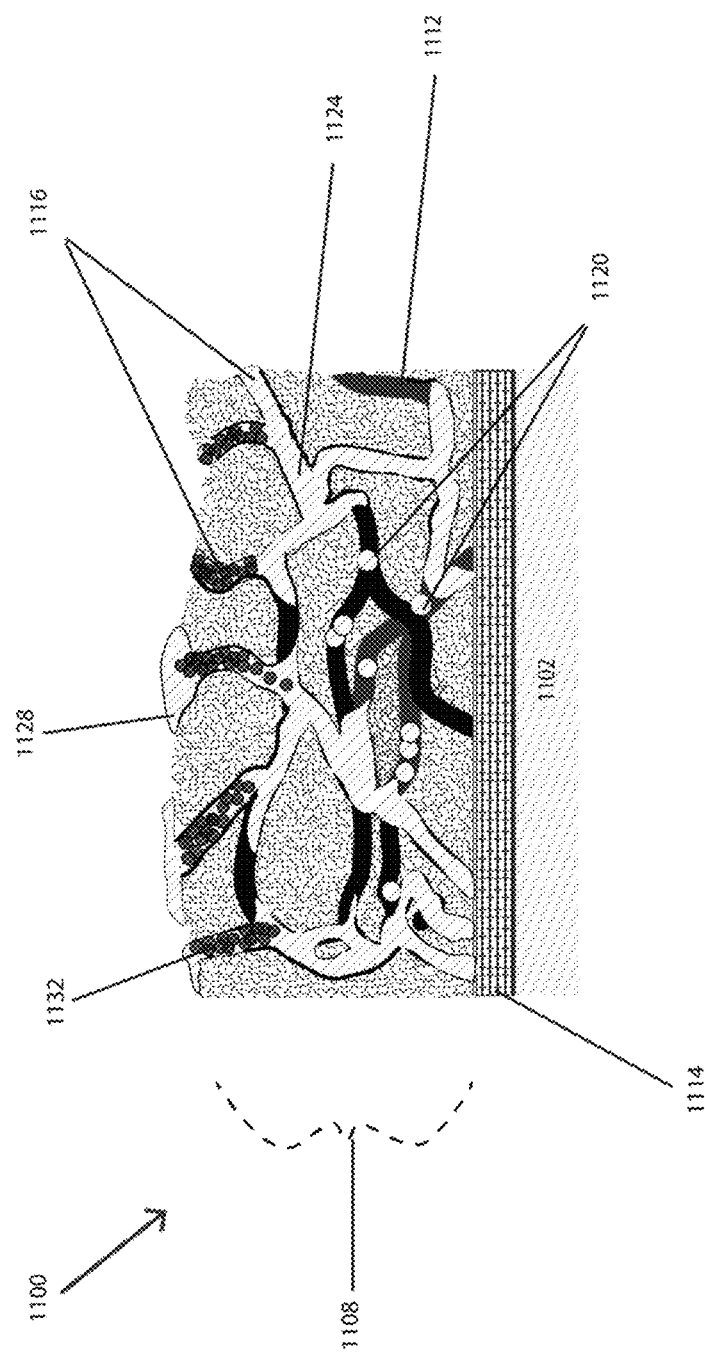
FIG. 11 depicts schematically a segment of an embodiment of an orally ingestible delivery system in cross-section.

FIG. 11 depicts an embodiment of an orally ingestible delivery system 1100 in which space-occupying solids 1132 (whether fluid-forming or non-fluid-forming) are disposed within the pores, here shown as supplementing a confluent fluid layer 1124 that has been formed from space-occupying fluid (whether gas or liquid), as described above. The depicted embodiment shows an acid-resistant shell 1108 (for example, an acid resistant protease digestible membrane) similar to those described previously, covering a therapeutic agent compartment 1102, having an acid-resistant shell 1118, and penetrated by a system of pores 1112 that can permit the passage of fluids from the external environment through the outer acid-resistant layer 1118 to contact an optional inner erodible layer 1114. As was described for previous Figures, if the inner erodible layer 1114 is protease-digestible, its combination with the acid-resistant shell 1108 forms an acid-resistant protease-digestible membrane. The confluent fluid layer 1124 (whether gas or liquid) and any free-floating fluid bubbles 1120 (whether gas or liquid) of sufficient dimensions to obstruct the pores can themselves form an inner dispersible acid barrier 1116, as previously described. Moreover, the confluent fluid layer 1124 can extravasate from the pores 1112 to form an additional partial or complete outer dispersible acid barrier 1128. In the depicted embodiment, however, the mechanical protection offered by the confluent fluid layer 1124 and the free-floating fluid bubbles 1120 can be supplemented or even replaced by the mechanical barrier provided by the space-occupying solids 1132. In addition, an external coating (not shown) surrounding the system 1100 can be either a sacrificial coating or a non-sacrificial coating, providing extra protection to the entire system 1100 including the contents of the pores 1112.

As shown in this Figure, the space-occupying solids 1132 are packed in the external portions of some or all of the pores 1112; also, as shown in this Figure, the space-occupying solids 1132 operate in conjunction with the space-occupying fluids within the pores 1112, as represented by the confluent fluid layer 1124 and any obstructing fluid bubbles 1120. In other embodiments, the space-occupying solids 1132 can occupy a larger portion or substantially all of the volume within the pores 1112 to provide the majority of the mechanical protection against stomach fluids. In embodiments, the space-occupying solids 1132 simply occupy space and thus deflect the ingress of stomach fluids. In other embodiments, the space-occupying solids can form space-occupying fluids (whether liquid or gas) when they react with the acid or proteases in the stomach fluids. For example, the space-occupying solids 1132 can be bicarbonate particles that produce carbon dioxide gas upon exposure to the stomach acid, a phenomenon that has been described in detail previously. Or, as described above with reference to FIG. 10, the space-occupying solids 1132 can be microcapsules containing space-occupying fluid that is released when the microcapsule walls are digested by the stomach fluids. For those space-occupying solids 1132 that react with the acid and/or proteases in the stomach or with intestinal enzymes, they can form a two-phase barrier system, comprising a first space-occupying fluid and a second space-occupying fluid; in embodiments, a first space-occupying fluid can provide protection during passage through the stomach while a second space-occupying fluid can provide protection during passage through a portion of the intestinal tract. The composition of this two-phase barrier system can be engineered to optimize the ultimate uptake of the therapeutic agent in the intestinal tract.

As examples of space-occupying solids 1132, solid particles can be used in powder form to fill the pores in whole or in part, with the selected substances being insoluble or minimally soluble in strongly acidic environments such as the stomach while being more soluble in neutral or higher pH, such as that environment in the duodenum. Examples of such are benzoic acid, bile acid, salicylic acid, citric acid, boric acid, and tartaric acid. Long chain fatty acids in their acid form may also be used, where the selected material is insoluble in a highly acidic environment but becomes soluble in neutral to alkaline pH environments that are also rich in emulsifying bile salts, such as within the duodenum. Such fatty acids may include palmitic acid, stearic acid, oleic acid, linoleic acid, linolenic acid, arachidic acid, behenic acid, lignoceric acid, cerotic acid, myristoleic acid, palmitoleic acid, sapienic acid, elaidic acid, vaccenic acid, linoelaidic acid, arachidonic acid, eicosapentaenoic acid erucic acid, docosahexaenoic acid.

4. Orally Ingestible Delivery Systems: Methods of Manufacturing Acid-Resistant Shell Structures A variety of manufacturing techniques are available to form the acid-resistant shell (for example, an acid resistant protease digestible membrane) as described herein. These manufacturing techniques are exemplified with reference to those embodiments using gas-producing substances as the barrier-forming substances, wherein the gas-producing substances form a gas upon exposure to stomach acid. It is understood, however, that many of these manufacturing techniques can be applied to those systems that use space-occupying fluids or solids to produce the dispersible acid barrier as disclosed herein. The manufacturing techniques described below can be modified by skilled artisans to encompass the use of space-occupying fluids and solids by use of no more than routine experimentation.

In an exemplary embodiment, an aqueous phase comprising water, bicarbonate and xanthan gum can be emulsified within a waxy layer that comprises unrefined beeswax and polyisobutylene, and this emulsion can be used to form the porous acid-resistant shell. The amount of polyisobutylene can be selected to provide desirable flexibility and integrity to the layer, for example an amount ranging from about 0.5% to about 5%. In an embodiment, the emulsion can contain about 1% polyisobutylene. Additives such as fibers can be included in the emulsion to improve its structural strength.

In embodiments, particularly where gas-producing substances are deployed within the matrix of the membrane, fibrous additives such as xanthan can contribute to the formation of elongated channels within the membrane, and these channels can extend and intertwine sufficiently to permit the ingress of stomach acid; as stomach acid encounters the gas-producing substances disposed within the membrane, it will activate these substances and produce gas that will occupy the channels and extend through the channels, as has been previously described. In embodiments, edible proteins or hydrocolloids can contribute to the formation of elongated channels. In embodiments, edible proteins such as whey protein, soy protein, or natural or partially hydrolyzed collagen can contribute to the formation of elongated channels.

As another approach for forming channels or pores chemically in the presence of gas-producing substances, dedicated gas-formers can be added to a semi-solid matrix so that they produce gas that forms channels through the semi-solid matrix, which channels become incorporated in the matrix as it solidifies to form the porous acid-resistant layer; a second set of gas-producing substances can be dispersed through the matrix separately or as part of the same process, wherein this second set of gas-producing substances is destined to be activated upon contact with stomach acid. The dedicated gas-formers that create the channels in the semi-solid matrix can operate by chemical reactions or other mechanisms to allow them to produce gas bubbles within the semi-solid matrix that will ultimately congeal to form channels or pores within the matrix.

In embodiments, channels or pores can be formed in the acid-resistant matrix architecturally, that is, by designing the arrangement of the matrix itself so that it includes channels or pores. For example, the layer can be formed as a porous lattice of waxy material, using techniques for lattice construction that are familiar in the art. As an exemplary approach, channels or pores can be included in the layer if the layer is fabricated as a regular or irregular meshwork. The layer can comprise, for example a pattern of thinner sublayers overlying each other, each sublayer having matrix material and voids arranged in a regular or irregular pattern, or, for example, a tangle of extruded solid or semi-solid matrix laid down so that there are interstitial voids. Other arrangements for producing channels or pores in the layer or designing the layer so that it contains channels or pores can be envisioned by skilled artisans. In embodiments, a one-layer acid-resistant shell can be formed in which a waxy layer is intertwined with a gel layer, with gas-forming substances disposed within the entire layer allowing gas to form that will percolate to the surface and form the dispersible acid barrier.

If one or more sets of gas-forming substances are used, they can all be dispersed within the acid-resistant shell as the layer is being formed. In an embodiment in which a waxy layer forms the matrix for the acid-resistant shell, an emulsion can be formed within the waxy substance by mixing in a concentrated aqueous solution of bicarbonate; the emulsion (including the waxy phase and the aqueous phase) can then be used to form the acid-resistant shell in free form, for example to be wrapped around or applied to an inner protease-digestible layer. In embodiments, the emulsion can be applied to the gelatin capsule using standard techniques (dipping, spraying, and the like), where the capsule wall acts as the inner erodible layer for the device. Using this technique, the water within the aqueous phase of the emulsion can evaporate, leaving behind bicarbonate crystals as deposits of gas-producing substances within the matrix. As described previously, these crystals can form carbon dioxide by reacting with the hydrochloric acid in the stomach, with the stomach acid being allowed to enter the waxy matrix and access the crystals via the system of channels or pores within the layer.

In embodiments, gas-producing substances or space-occupying fluids can be included in a separate layer beneath the acid-resistant shell, with these substances to be accessed by stomach acid that passes through the system of channels or pores within the acid-resistant shell. Such a layer can include gas-producing substances contained within a matrix such as gelatin, sprayed on the surface of a therapeutic agent, or otherwise disposed in between the acid-resistant shell and an inner erodible layer whether formed as part of the device or whether formed as a layer surrounding the therapeutic agent. A layer of space-occupying fluids beneath the waxy layer can be covered with a sacrificial coating that is eroded by stomach acid or enzymes, releasing the space-occupying fluids into the pores to displace the stomach acid. Other arrangements of gas-producing substances, space-occupying fluids, or both, can be envisioned by artisans of ordinary skill in the relevant arts.

If the waxy substance requires fortification, additional polymers can be added to the waxy matrix as the emulsion is being formed. For example, small amounts of a rubbery, hydrophobic polymer such as polyisobutylene can be added to increase structural stability and integrity. Other polymers such as polyethylene, polyisobutylene, polyvinyl acetate, and the like can be similarly added to the waxy matrix alone or in combination to improve its mechanical properties. For example, xanthan gum or other hydrophilic polymers can be added to the waxy substrate to enhance the diffusion of the aqueous phase throughout the wax and thereby facilitate the formation of the system of pores. In embodiments, additives to the waxy substrate can include cellulose derivatives (for example, hydroxypropyl cellulose, hydroxypropyl methyl cellulose, carboxymethylcellulose) and other hydrocolloids (pectin, pullulan, guar gum, xanthan gum, gum arabic, acacia gum, carrageenan, alginate, chitin, chitosan, starches, soy protein, whey protein, collagen, and gelatin), polypeptides, polyvinyl alcohol, polysaccharides and derivatives, hyaluronic acid, poloxamers, PEG, poly(N-vinylpyrrolidone); small molecules such as mono- and oligo-saccharides, water soluble salts, glycerol and edible surfactants (for example, lauric arginate).

In embodiments, fibers can be added to the acid-resistant shell to improve strength, elasticity, or durability. While fibers of any kind may be used, edible fibers, for example certain vegetable-derived fibers, are particularly advantageous, since the acid-resistant shell and any fibers it contains will be ingested and digested. Notwithstanding the foregoing, inorganic fibers can be used if suitable for use in nutritional and/or pharmaceutical products. Suitable vegetable fibers can include, for example, fibers derived from the skin or bast surrounding the stem of a plant or from the fruit of a plant (for example, banana fibers, coconut fibers, soybean fibers, and the like), or fibers derived from leaves or plant stalks (for example, wheat, rice, barley, grass, and the like). Fibers can be admixed with the waxy matrix, with the aqueous phase then emulsified therein, or fibers can be used to construct a reinforcement or support structure to which the waxy matrix (with or without an entrained aqueous phase) can be applied. In yet other embodiments, the architecture for the pores can be patterned with digestible materials scattered throughout the acid-resistant shell as it is formed, with the membrane to be deposited on the therapeutic agent compartment or the therapeutic agent itself.

In embodiments, a waxy matrix material can be applied to a preformed latticework, where the lattice is formed from a stiffer wax, a polymeric network, or fibers. In embodiments, the lattice can be formed with defibrillated fibers coated with wax, fat, or fatty acids, with the lattice then coated with the waxy substrate for the acid-resistant shell. Gas-forming substances and/or space-occupying fluids or solids can be included within the waxy substrate to be applied to the lattice, or such substances can be included in an undercoat that stomach acid can reach by pores or channels that exist in the coated latticework.

In embodiments, the barrier-forming substances (whether gas-producing substances and/or space-occupying substances) can reside within the interstices of the lattice, being positioned there before the lattice is coated with wax, after the lattice is coated with wax, or both. For example, a lattice can be formed first, then coated with the water-in-wax emulsion previously described, wherein the water phase of the emulsion contains a concentrated aqueous solution of bicarbonate; as the water evaporates, the bicarbonate remains where it was carried by the emulsion, for example within the valleys and voids of the lattice structure. In other embodiments, pH sensitive substances such as the gas-producing substances can be attached to fibers within the matrix, so that as the fibers are digested by the stomach acid, the acid also contacts the gas-producing substances and activates them, so that the gas or fluid comes to fill the pores and to reach the surface of the acid-resistant shell as the dispersible acid barrier. In embodiments, the fibers can be coated with or permeated with barrier-forming substances, for example with the barrier-forming substances adherent to the fibers or embedded therein. In embodiments, to include the barrier-forming substances in the fibers, the fibers can be co-extruded with barrier-forming substance materials. In other embodiments, the barrier-forming substances can enter the fibers in solution with subsequent crystallization as the fibers dry, as described above.

In embodiments, the acid-resistant shell can be formed separately, using the emulsion technique described above for example, and allowed to solidify. The solid or semi-solid layer can then be wrapped around the inner erodible layer or it can be wrapped around the therapeutic agent that is already encased in an erodible layer (for example, a gel capsule). In a two-layer system, an acid-resistant shell can be formed from a substance that resists both acid and proteases, for example wax. The inner layer can be formed from a material that is digestible by proteases, for example, a gelatin capsule. The inner layer can be intrinsic to the orally ingestible delivery system itself, as shown for example in FIGS. 5 and 6, or the inner layer can be intrinsic to the dosage form of the therapeutic agent that resides in the therapeutic agent compartment, as is described below in conjunction with FIG. 10. Moreover, in two-layer or multi-layer systems, it is understood that gas-producing substances can be disposed within both the inner erodible layer and the acid-resistant shell.

In embodiments, a layer of fibers bearing barrier-forming substances can be used without a waxy matrix to provide an acid-resistant shell. For example, an insoluble fiber like corn husks or other vegetable matter can be used to form a netlike or weblike layer within which the barrier-forming substances are suspended, attached, or otherwise deployed. In such a layer, the barrier-forming substances can be deposited within certain fibers that are dissolvable, so that the barrier-forming substances are liberated from the fibers as they are dissolved. In embodiments, adhesive materials attach the barrier-forming substances to soluble or insoluble fibers, while in other embodiments; a variety of edible adhesives would be available, or a material such as wax can be used to coat the fibers and trap the barrier-forming substances in proximity thereto. These coated fibers can then be used to form the acid-resistant shell apart from any other waxy matrix. To create the network or web of fibers to provide the acid-resistant shell, the fibers can be entangled using any available commercial technique such as weaving, extrusion, air-laying, spin melting, and the like. Advantageously, an outer coating can be applied over the acid-resistant shell to provide structural stability and to protect it initially from the incursion of stomach fluid. Advantageously, an inner erodible layer can be provided, with or without its own embedded barrier-forming substances, to allow fine-tuning of therapeutic agent release.

For those systems using space-occupying solids or fluids as the barrier-forming substances, similar techniques can be used to deploy the barrier-forming substances within the matrix of the acid-resistant shell instead of or in addition to their deployment within the pores. As an example, the inner erodible layer can be formed on top of the therapeutic agent or can be provided by a third party as an encapsulated therapeutic agent, for example as a gel capsule containing the therapeutic agent. The therapeutic agent form factor can then be coated with a layer of beeswax and polyisobutylene within which is suspended a dissolvable material that can be removed in order to develop the system of empty pores within the layer. For example, sodium bicarbonate crystals can be suspended in the waxy layer, to be removed by exposing the layer to acid, which converts the bicarbonate to carbon dioxide. With agitation, the carbon dioxide bubbles can exit the waxy layer, leaving behind empty channels or pores. These channels can be filled with space-occupying fluids or solids by immersion, spraying, injection, or other techniques known in the art. Once the channels are filled adequately with the space-occupying fluids and/or solids, these substances produce the barriers that can protect the device from stomach fluids when it is ingested, as described previously.

5. Orally Ingestible Delivery Systems: Coatings and Additional Layers

As would be understood by skilled artisans, the rate of acid penetration and/or the decomposition time of the acid-resistant shell (for example, an acid resistant protease digestible membrane) can be engineered to match the desired delivery profile for the therapeutic agent, for example by increasing the thickness of the outer acid-resistant layer, or by including additives in the outer acid-resistant layer to improve acid-resistance, decrease flakiness, or alter the adherence of the outer acid-resistant layer to the underlying erodible layer. Moreover, inner layers such as an inner erodible, for example, protease-digestible, layer can be formulated to include agents that delay its digestibility when exposed to proteases, thereby protecting the therapeutic agent contained within the therapeutic agent compartment and delaying its release. For example, if an inner erodible layer is formed with gelatin, the delaying substances can be formulated within the gelatin itself, and the therapeutic agent can be enclosed within such a specially-formulated gelatin layer.

In other embodiments, a layer containing barrier-forming substances can be provided beneath the acid-resistant shell or within the acid-resistant shell, so that stomach fluid penetrating the acid-resistant shell would have access the barrier-forming substances disposed therein. Such a protective layer can be applied to an inner erodible layer such as a gelatin layer or it can be applied to the underside of the acid-resistant shell as its own layer. In the latter situation, the acid-resistant shell plus the protective layer containing the barrier-forming substances can be applied to a separate gelatin capsule or other form factor provided by a third party, where the form factor can contain the therapeutic agent or the therapeutic agent deliverable.

Figure 12:
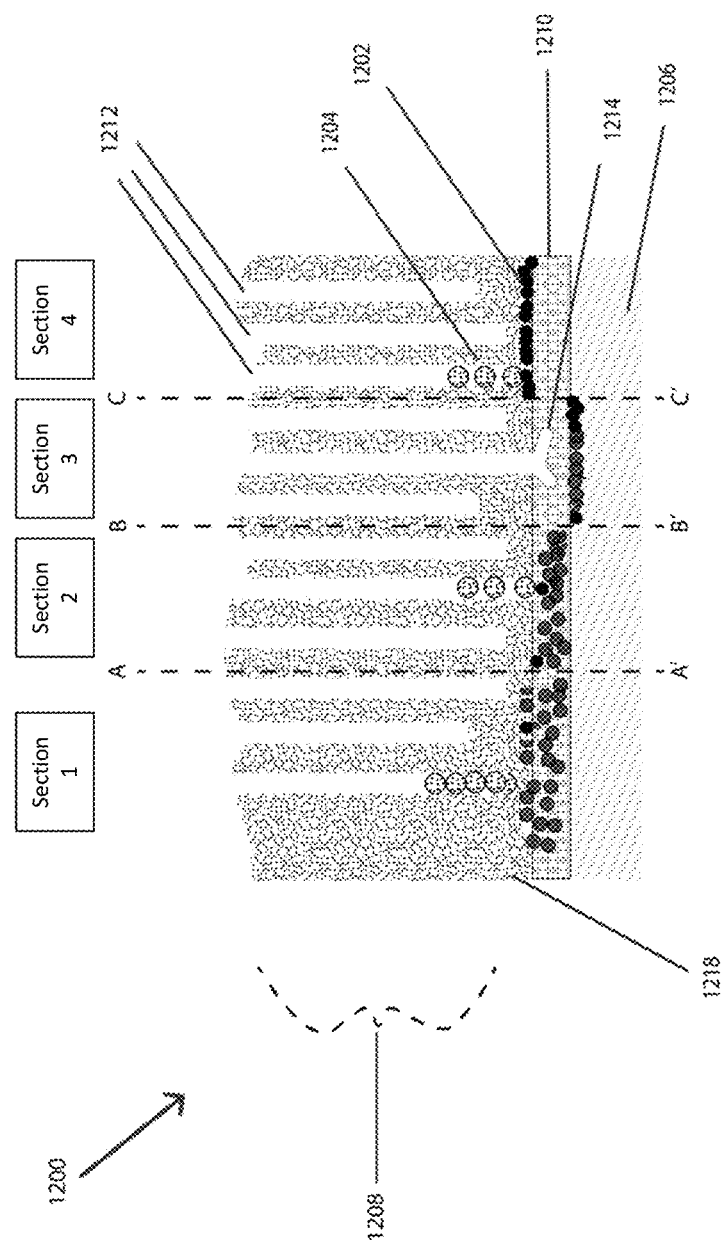
FIG. 12 schematically a segment of an embodiment of an orally ingestible delivery system in cross-section.

In embodiments, the acid-resistant shell (for example, an acid resistant protease digestible membrane) can be constructed to permit passage of stomach fluid, but the fluid would encounter the barrier-forming substances in the protective layer. An illustrative embodiment is depicted in FIG. 12. FIG. 12 depicts in cross-section an embodiment of an orally ingestible delivery system 1200 showing an acid-resistant shell 1208 penetrated by a system of pores 1212, here depicted as parallel and substantially similar in size, such as would be produced by piercing the matrix 1218 of the acid-resistant shell 1208 with a plurality of collinear microneedles. It is understood that the system of pores 1212 can be straight, curved, serpiginous, separated, intersecting or non-intersecting, as has been previously described. In the depicted embodiment, the system of pores 1212 can be empty or filled with a fluid or solid material, either barrier-forming or non-barrier-forming. As depicted, the pores are of different lengths, and they penetrate the matrix 1218 to different depths, although it is understood that the pores can be of similar length with similar degrees of matrix penetration. Some or all of the pores can penetrate the acid-resistant shell completely. Disposed beneath the pores are a plurality of barrier-forming substances 1202 that can be deployed beneath the acid-resistant shell 1208 as depicted, whereby stomach juice (not shown) that enters the system of pores 1212 can access some or all of the barrier-forming substances 1202 to activate them, for example to release gas bubbles 1204 that can enter the system of pores 1212 and block the pores to prevent further ingress of the stomach fluid. In the depicted embodiment, an additional, optional protective layer 1210 is illustrated on the undersurface of the acid-resistant shell 1208, between the acid-resistant shell 1208 and the therapeutic agent chamber 1206. As shown, the barrier-forming substances 1202 can be deployed on top of and within the protective layer 1210, as shown to the left of dotted line A-A' (Section 1); or simply within the protective layer 1210, as shown to the right of dotted line A-A' and to the left of dotted line B-B' (Section 2); or beneath the protective layer 1210, as shown to the right of dotted line B-B' and to the left of dotted line C-C' (Section 3); or on top of the protective layer 1210, as shown to the right of dotted line C-C' (Section 4). If the protective layer 1210 is formed from an inner erodible, for example, an acid-hydrolysable and/or protease-digestible material such as gelatin, it can be eroded by stomach fluid that reaches it through the system of pores 1212, as shown schematically at 1214. A combination of the acid-resistant shell 1208 and a protease-digestible protective layer 1210 forms an acid-resistant protease-digestible membrane. If the acid or protease digests the protective layer 1210 overlying the barrier-forming substances 1202, these substances can be released or activated to enter the system of pores 1212 to provide protection against further effects of stomach fluid that would otherwise enter the system of pores 1212.

In embodiments, the protective layer 1210 is formed from acid-hydrolysable and/or protease-digestible materials such as gelatin. However, the protective layer 1210 can be formed of any biocompatible material. For example, in embodiments, the protective layer 1210 is an erodible layer that is not necessarily acid-hydrolysable and/or protease-digestible, but rather is made from material(s) selected to optimize the release of the therapeutic agent in appropriate sections of the gastrointestinal tract. While the positioning of the barrier-forming substances 1202 has been illustrated in this Figure with reference to the protective layer 1210, it is understood that the protective layer 1210 is optional. In the absence of the protective layer 1210, the barrier-forming substances 1202 can be deployed beneath the acid-resistant shell 1208 (for example, an acid resistant protease digestible membrane) as a separate sheet, or the barrier-forming substances 1202 can be attached to the undersurface of the acid-resistant shell matrix 1218, or the barrier-forming substances 1202 can be attached to the therapeutic agent compartment 1206 or integrated with the therapeutic agent deliverable (not shown). In other embodiments, not depicted in this Figure, a sheet or a protective layer containing the barrier-forming substances as described herein can be positioned within the acid-resistant shell matrix at any level: it need not be positioned below the acid-resistant shell matrix.

In an exemplary multi-layer design that embodies the principles disclosed herein, an acid-hydrolysable and/or protease-digestible capsule, such as gelatin capsule, can encase the drug deliverable, and this capsule can then be coated with a layer of solids. This coating can be a suspension or solution containing the solids that is sprayed onto the surface of the capsule, and/or the capsule can also be dipped or rolled in a coating. As previously described, the solids can be contained in their own preformed layer, to be wrapped around the capsule, or to be affixed to the undersurface of the acid-resistant shell or to be sandwiched within two layers of an acid-resistant shell. The solids in this layer, however deployed, can be gas-producing solids or non-gas-forming solids. They can be suspended in a liquid or gel vehicle that facilitates their application, for example a volatile liquid that is easily removed during a spraying process, or a condensable or curable liquid that can solidify over time. Liquid alone may be used to suspend the solids, or other additives may be used to help solidify the layer, such as gelatin, shellac, corn starch, zein, pectin, etc. In an exemplary embodiment, calcium carbonate can be suspended in gelatin, with the suspension being heated. While heated, the suspension can be sprayed onto an underlying gelatin capsule and can solidify over time, or the gelatin capsule can be dipped into the suspension. These techniques allow the particles of solid materials to be trapped inside and secured in their own layer. Once this layer is applied to the gelatin capsule, a layer of wax can then be applied on top of it to create an acid-resistant shell. This acid-resistant shell can simply be formed from wax and with a polymer such as polyisobutylene acting as a plasticizer. The wax layer is provided with pores that penetrate through it, allowing stomach fluids to permeate through the wax layer to reach the layer containing the solids. A number of mechanisms have been described already for forming such a wax layer. For example, the wax may be sprayed on to form a layer, a technique that would create the layer out of micron-sized coalescing droplets or "pebbles." In this scenario, the space between the pebbles acts as fluid-permeable channels, so that stomach fluids can pass through the channels and access the underlying solids layer. As another mechanism, wax can be applied in a homogenous sheet, and pores can later be formed in the sheet. Mechanical means like microneedles can be used to create pores in the sheet. Digestible fibers can be used to create pores, with the stomach fluids eroding the fibers or interacting with the fibers to create pores or discontinuities in the wax layer. Other mechanisms for creating a system of pores within the acid-resistant shell can be envisioned by skilled artisans.

Aside from spraying or dipping techniques as described above, there are other high-throughput manufacturing techniques that can be used to develop orally ingestible delivery systems in accordance with the principles disclosed herein. For example, an entire orally ingestible delivery system can be formed from a previously-formed multi-layered sheet, or the orally ingestible delivery system can be formed from one or more separately-formed sheets. For example, an acid-hydrolysable and/or protease-digestible layer (for example, gelatin) can first be formed with blade coating, extrusion, curtain coating, or other techniques familiar to skilled artisans. Blade coating is a process to apply a uniformly thin film of liquid continuously onto a surface through the use of a moving smoothing device like a blade that spreads out the liquid evenly on the surface. Extrusion (for example, hot melt extrusion) is a process of applying heat and pressure to melt a material and force it through a slit or an orifice in a continuous process, allowing the formation of products with uniform shape and density in a variety of shapes, including bags, spheres, films, sheets, tubes, fibers, foams and pipes. Curtain coating creates an uninterrupted sheet of fluid that falls on a substrate, created by a slit or die at the base of a holding tank that dispenses the fluid as a sheet. One or more layers of the orally ingestible delivery system can be formed in this way and the layers can then be combined to form the entire orally ingestible delivery system. For example, first an acid-hydrolysable and/or protease-digestible layer like gelatin can be formed as a flat sheet, then the acid-resistant shell can be formed as a separate sheet. These two layers can be joined together to form a two-layer composite, with pores formed in the acid-resistant shell as described above. Such a two-layer composite, if including an acid-resistant shell layer and a protease-digestible layer, forms an acid-resistant protease-digestible membrane. Barrier-forming substances can be deployed within or below the acid-resistant shell as described above. Any of the techniques for forming such layers can be employed for any or all of the layers of the orally ingestible delivery system, as would be understood by skilled artisans in the field.

As would be further understood by skilled artisans, the decomposition time of the acid-resistant shell can be further adjusted by adding coatings on top of or beneath the inner erodible layer, for example a coating possessing delayed release or extended release properties when exposed to stomach acid and/or proteases. In addition, the acid-resistant shell itself can be covered with an additional sacrificial or non-sacrificial coating, for example possessing delayed release or extended-release properties when exposed to stomach acid and/or proteases. Techniques for forming such layers are well-known in the art, including the techniques described above, such as spraying, dipping, blade coating, extrusion, curtain coating, and the like. For example, a conventional enteric coating can be added on top of an inner erodible layer (for example, on top of a gelatin capsule) before depositing the outer acid-resistant layer on top. The conventional enteric coating can be selected and formulated to withstand conditions in the small intestine sufficiently, so that it allows the therapeutic agent encased within the therapeutic agent compartment to be transported therein to reach the desired location in the small intestine or colon. In embodiments, the therapeutic agent itself can be enveloped by a coating intended to regulate the release of the therapeutic agent in the intestine, instead of or in addition to other coating layers that are incorporated in the orally ingestible delivery system, as previously described.

While a wide range of conventional enteric coating formulations can be used, the orally ingestible delivery system will permit the selection of materials and thicknesses for additional coating layers (whether added on top of the inner erodible layer or under the inner erodible coating layer) that are less robust than those materials or thicknesses used for conventional enteric coatings. This is because traditional enteric coatings require greater durability so that they can resist the harsh conditions in the stomach, including acid and protease induced hydrolysis. By contrast, the dispersible acid barrier of the orally ingestible delivery system disclosed herein protects the inner erodible layer from stomach fluid. Therefore, there is a lower performance demand for the enteric coatings that are interposed within, above, or below, the layers of the differentially permeable (for example, digestible) capsule system, as compared to conventional enteric coatings, because of the additional protection afforded by the dispersible acid barrier. Thus, in embodiments, an enteric coating can be used that would be considered rather "weak" in resisting acidic- and protease-degradation. In other embodiments, the interposed enteric coating can be specifically designed for the conditions in the intestine. For example, bile secretion releases copious amounts of lipase and surfactants in addition to protease. Thus, the interposed modified release layer can be a lipid-based formulation, degradable by lipase at neutral pH at a predictable rate. Alternatively, traditional enteric coatings can be employed, but as a thinner than normal layer.

Enteric coatings and other specialized coatings can be applied directly to the dosage form of the therapeutic agent. Enteric coatings and other specialized coatings can alternatively or additionally be applied to the entire orally ingestible delivery system. Coatings to be applied to the entire system can be selected to improve the ingestibility of the system, or to protect it from mechanical trauma as it passes through the stomach. For example, confectioner's glaze or pharmaceutical glaze can provide a glossy finish and protective coating around the entire device. Such coatings are well-known in the formulation field. Such coatings can be formed from natural ingredients, such as shellac (formed from insect excretions) and carnauba wax.

6. Orally Ingestible Delivery Systems: Therapeutic Agent Modifications

As described previously, the therapeutic agent itself can be modified or otherwise formulated to interact in concert with the orally ingestible delivery systems described herein. It is also understood that the therapeutic agent itself can be formulated with gas-producing substances and/or space-occupying fluids or solids as part of the dosage form or enveloped with a layer of such substances. For example, the dosage form in the therapeutic agent compartment can be sprayed with an additional layer of gas-producing substances, which would be available for activation if they encounter stomach acid.

In embodiments, the therapeutic agent can be formulated as a therapeutic agent dosage form or therapeutic agent deliverable so that it includes an overlying erodible layer, allowing it to be inserted into the differentially permeable (for example, digestible) capsule system of an orally ingestible delivery system. This would permit the therapeutic agent dosage form to be fabricated by a different party than the manufacturer of the orally ingestible delivery system, so that the dosage form can be introduced into or covered by the differentially permeable capsule system to produce the complete orally ingestible delivery system. An embodiment of configuration is depicted in FIG. 13.

Figure 13:
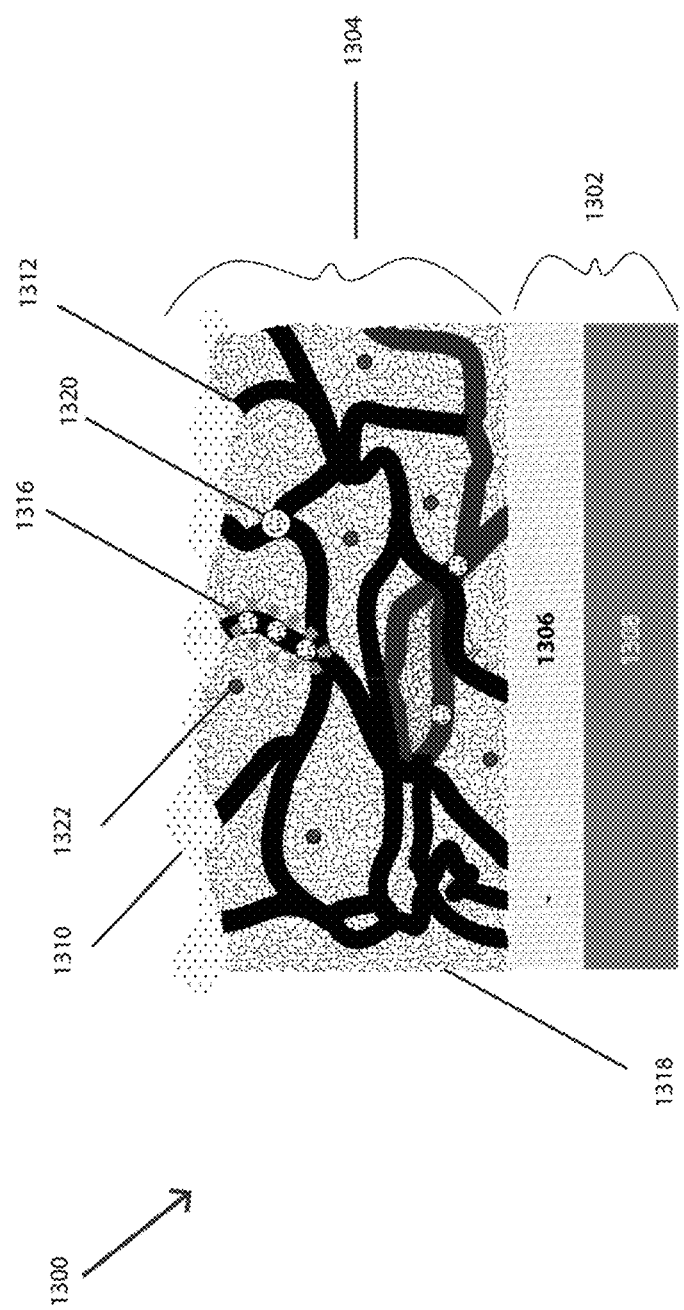
FIG. 13 schematically a segment of an embodiment of an orally ingestible delivery system in cross-section.

As shown in FIG. 13, an orally ingestible delivery system 1300 can be formed as a single layer differentially permeable (for example, digestible) capsule system 1304, here shown schematically as comprising an acid-resistant layer 1318 and having an inner dispersible acid barrier 1316, where the dotted line encloses three representative gas bubbles or fluid droplets, each one similar to the single gas bubble or fluid droplet 1320 shown within the pores 1312, representing the fact that the inner dispersible acid barrier 1316 can be formed from a single fluid bubble or droplet, or a series of fluid bubbles or droplets, or a confluent layer of fluid. Also shown is an optional outer dispersible acid barrier 1310, where the differentially permeable capsule system 1304 envelopes or encases a therapeutic agent deliverable 1302. Similar to other depictions of a differentially permeable capsule system for use with the orally ingestible delivery systems that have been disclosed previously, the acid-resistant shell 1318 illustrated in this Figure contains a system of pores 1312 within its matrix, with the pores 1312 containing a plurality of gas bubbles 1320 that have been produced by the encounter of the stomach acid with gas-producing substances. The orally ingestible delivery system 1300 shown in this Figure has been exposed to stomach acid during a period of residence in the stomach. As a result, the gas producing substances (not shown) originally dispersed within the system of pores 1312 have reacted in whole or in part with the stomach acid to produce gas bubbles 1320 within the system of pores 1312, thereby forming the inner dispersible acid barrier 1316 and optionally the outer dispersible acid barrier 1310.

In more detail, while the inner dispersible acid barrier 1316 only shows three non-confluent gas bubbles as constituting the inner dispersible acid barrier 1316, it is understood that all of the varieties of an inner dispersible acid barrier illustrated, for example, in FIG. 8 and further described in conjunction with FIG. 8 are embraced by the schematic diagram of the inner dispersible acid barrier 1316 depicted in this Figure. Although the gas bubbles 1320 in this Figure are shown as discrete bubbles, it is understood that the gas bubbles 1320 can coalesce and occupy some of or substantially all of the space within the pores; this coalescence is to be anticipated, as the gas is released from the gas-producing substances and expands within the pores 1312. As shown in this Figure, some unreacted gas-producing substances 1322 remain within the matrix 1324, while those gas-producing substances previously contained within the system of pores 1312 have already been activated by contact with stomach acid, with release of gas bubbles 1320 into the pores 1312. While this Figure shows gas bubbles 1320 acting as the inner dispersible acid barrier 1316, it is understood that space-occupying fluids and/or solids can also act as inner dispersible acid barriers, as has been illustrated previously.

As depicted in this Figure, the differentially permeable (for example, digestible) capsule system 1304 envelopes a therapeutic agent deliverable 1302 that can be provided separately. The differentially permeable capsule system 1304 provides the acid-resistant layer 1318, and the dispersible acid barrier 1316 within the pores 1312 and optionally on the surface 1310. The therapeutic agent deliverable 1302 can be provided by a third party, to be subsequently enclosed within the differentially permeable capsule system 1304. This allows the differentially permeable capsule system 1304 to be adapted to the needs of the third-party manufacturer(s) of the therapeutic agent deliverable 1302.

In embodiments, the therapeutic agent deliverable 1302 can comprise an erodible enclosing layer 1306 disposed to surround in whole or in part the therapeutic agent 1308 itself. While the Figure refers to a single therapeutic agent 1308, it is understood that the therapeutic agent deliverable can comprise one or more identical or different therapeutic agents. The differentially permeable (for example, digestible) capsule system 1304 enveloping the therapeutic agent deliverable 1302 is designed to provide a layer of acid resistance through the mechanisms described herein, whether through gas production as contemplated by this Figure, or by the deployment of space-occupying fluids or solids. However, once the protective barrier layer(s), provided by the optional outer dispersible acid barrier 1310 and/or the inner dispersible acid barrier 1316, disperse(s) in the small intestine, the therapeutic agent deliverable 1302 contained within the differentially permeable capsule system 1304 can be exposed to attack from intestinal fluid contents, including proteases.

The therapeutic agent deliverable 1302 can be formulated independently, and in any advantageous way to resist or respond to the effects of intestinal fluid. For example, in embodiments, an initial enclosing layer 1306 can be provided that can modify the delivery of the therapeutic agent 1308 into the intestinal tract. In an embodiment, the enclosing layer 1306 can be erodible, for example protease-digestible, which can lead to a fairly rapid release of the therapeutic agent 1308 in the small intestine as intestinal enzymes penetrate the overlying acid-resistant layer 1318 following the dispersal of the barriers as described above. In embodiments, additional enclosing layers (not shown) for the therapeutic agent 1308 can be provided above or below the initial enclosing layer 1306 to better modify the release of the therapeutic agent 1308 within the small or large intestine. Such additional enclosing layers (not shown) can be added, for example during formulation of the therapeutic agent 1308, to target the delivery of the therapeutic agent 1308 to a particular location, or to fine-tune its release profile. In embodiments, the enclosing layer 1306 can be minimal or absent entirely, with the therapeutic agent 1308 formulated as a tablet or caplet (coated or uncoated) having no separate enclosure added to it. In embodiments the therapeutic agent deliverable 1302 can comprise a plurality of individual therapeutic agent dosage forms that are all encased in a single enclosing layer 1306, for example a erodible enclosing layer like a gelatin capsule, which individual dosage forms can each themselves be encapsulated or enveloped by one or more covering layers that regulate their release, protect them from the environment, and the like. In other embodiments, the therapeutic agent deliverable 1302 comprises a single therapeutic agent dosage form, optionally packaged with other substances that protect it, support it, modify its release, and the like. For example, a therapeutic agent deliverable 1302 comprising probiotic organisms can also include substances that support the living organisms, that provide nutrients for them, or that act synergistically with them when they reach their target destination in the small intestine or colon. In other embodiments, there can be a plurality of deposits of therapeutic agents (not shown) distributed within the acid-resistant layer 1318, with the various therapeutic agent deposits containing the same or different therapeutic agent deliverables.

The orally-ingestible delivery system 1300 depicted in FIG. 13 is suitable for use with a wide variety of therapeutic agent deliverables 1302, which deliverables 1302 may also be provided by third parties for enclosure within the orally ingestible delivery system 1300. In embodiments, the differentially permeable (for example, digestible) capsule system 1304 can be fabricated separately from the therapeutic agent deliverable 1302, with the two components being joined together secondarily to form the entire orally-ingestible delivery system 1300 for the specific deliverable. In embodiments, the same differentially permeable capsule system 1304 can be used for a large variety of therapeutic agent deliverables 1302, with the deliverables to be manufactured by a pharmaceutical company for example, and thence to be enrobed with or encased within the differentially permeable capsule system 1304. In embodiments, the differentially permeable capsule system 1304 is not customized for the therapeutic agent deliverable 1302; customization is instead provided to the deliverable 1302 itself by the pharmaceutical manufacturer who formulates the therapeutic agent 1308 or agents as dosage forms, and then enrobes or encases them in a erodible enclosing layer 1306 such as a gelatin capsule, for insertion into or envelopment by the differentially permeable capsule system 1304. The customization process for the therapeutic agent deliverable 1302 can include specialized formulations, additional layers, separate dosage forms, and the like, to control the timing and the location for delivery of the therapeutic agent(s) within the small or large intestine following the programmed dissolution of the differentially permeable capsule system 1304.

In more detail, the therapeutic agent deliverable 1302 can be formed from a therapeutic agent 1308 in liquid, semi-solid, or solid form having an erodible enclosing layer 1306 as shown in FIG. 13. For example, a protease-digestible glycerin capsule can be used to enrobe or encase the therapeutic agent 1308. Above or below the glycerin capsule, other layers can be used as coatings to impart desirable properties, for example to improve strength, or to modify the timing or duration of release. In embodiments, an additional layer containing barrier-forming substances can be applied above or beneath the glycerin capsule to supplement the formation of barriers (for example, gas formation or release of space-occupying fluids) carried out within the acid-resistant layer 1318, or to provide a different layer of protection that affects the timing or the extent of therapeutic agent release. The acid-resistant shell 1318 of the differentially permeable (for example, digestible) capsule system 1304 can the envelop the therapeutic agent deliverable 1302, protecting the deliverable from the action of stomach acid but allowing it to be released in a designated location within the intestine via the formation of barriers as described above. In embodiments, the differentially permeable capsule system 1304 and the therapeutic agent deliverable 1302 can be fabricated separately and/or by different manufacturers, with the two components being brought together subsequently by the same manufacturer(s) or by yet another manufacturer who combines the two components to make the complete orally-ingestible delivery system.

While the therapeutic agent deliverable has been described above with an emphasis on the incorporation of active pharmaceutical agents in the deliverable, it is understood that all varieties of therapeutic agents are appropriate for use with these systems and methods. The term "therapeutic agent," as defined and described below in more detail, can embrace any substance (whether living or non-living) used for any therapeutic purpose, including but not limited to pharmaceuticals, nutraceuticals, diagnostic agents, and medical devices.

7. Orally Ingestible Delivery Systems: Applications for Food and Drink

An orally ingestible delivery system that includes a water-swellable, acid-hydrolysable and/or protease-digestible phase has particular advantages for oral administration in foods or in drinks, because of its familiarity and palatability. Such a system can be used to deliver therapeutic agents such as APIs, vaccines, probiotics, etc., orally as a component of an edible delivery vehicle. As an example, an orally ingestible delivery system can be formulated with a matrix of tapioca starch (the water-swellable, acid-hydrolysable phase) containing gas-forming substances, said soluble, water-swellable matrix permeated by an interlaced insoluble matrix of food-grade cellulose fibers. The system can be sold in a dehydrated form as pellets or powder or other formed articles, ready for addition into the edible delivery vehicle of choice, such as edible gels or liquids. Upon hydration, the system will swell and become suspended in the oral delivery vehicle. As an example, the system can be formatted as "pearls" (or in any advantageous shape and size) to be dissolved in a flavored drink, wherein they hydrate and become suspended and drinkable with simple stirring. Once ingested, the "pearls" behave in similar manner to other one-layer orally ingestible delivery systems described herein, with the programmed release of its therapeutic agent contents. As would be appreciated by skilled artisans, food colorants and/or fragrances/flavors can be added to the pearls to enhance the consumer appeal of this delivery vehicle. In embodiments, this specialized oral delivery vehicle can be sold in a hydrated form if more convenient or commercially appropriate.

Disclosed herein, in embodiments, is an orally ingestible delivery system for delivering a therapeutic agent into an intestine of a mammal, comprising a hydrophilic matrix and a hydrophobic framework disposed therein, wherein the therapeutic agent is entrained within the hydrophilic matrix, and wherein the hydrophilic matrix further contains a plurality of gas-former packets comprising a gas-forming substance that converts to a gas upon exposure to stomach acid, wherein the hydrophilic matrix is susceptible to digestion by stomach acid or stomach enzymes to form a hydrophilic matrix residue, and wherein the digestion of the hydrophilic matrix exposes the gas-former packets to stomach acid, thereby converting the gas-forming substance to a protective gas, and wherein the protective gas migrates to a surface of the hydrophilic matrix residue to form a dispersible gas barrier thereupon, wherein the dispersible gas barrier protects the hydrophilic matrix residue from further digestion by stomach acid or stomach enzymes, and wherein the dispersible gas barrier is dispersible by bicarbonate in a duodenal portion of the intestine, thereby exposing the surface of the hydrophilic residue to intestinal enzymatic activity, wherein the intestinal enzymatic activity further digests the hydrophilic matrix residue and releases the therapeutic agent entrained therein, thereby delivering the therapeutic agent into the intestine. In embodiments, the therapeutic agent is disposed within discrete packets. In embodiments, the packets are encapsulated or coated. In embodiments, the therapeutic agent is combined with a second therapeutic agent entrained within the hydrophilic matrix. In embodiments, the therapeutic agent and the second therapeutic agent are contained within discrete packets, and in other embodiments, at least one of the therapeutic agents and the second therapeutic agent is entrained within the hydrophilic matrix without being disposed within discrete packets. In embodiments, the hydrophilic matrix comprises a protein or a polysaccharide, and the hydrophilic matrix can possess hydrocolloid properties. In embodiments, the protein is a gelatin. In embodiments, the hydrophobic framework comprises a hydrophobic polymer, which can be selected from the group consisting of cellulose, fatty acids, waxes, polyolefins, and edible or natural elastomers. In embodiments, the hydrophobic polymer is an unrefined beeswax. The hydrophobic framework can further comprise a second polymer having advantageous mechanical properties. In embodiments, the second polymer can be a polyisobutylene polymer or a cellulose polymer. In embodiments, the gas-forming substance is a substance that produces carbon dioxide gas, and the gas-forming substance can comprise a carbonate ion. In embodiments, the digestion by stomach acid or stomach enzymes exposes a portion of the hydrophobic framework as the digestion forms the hydrophilic matrix residue, thereby forming an exposed hydrophobic framework. The protective gas can adhere to or be attracted to the exposed hydrophobic framework as it migrates to the surface of the hydrophilic matrix residue.

Further disclosed herein are methods of delivering a therapeutic agent into an intestine of a mammal, comprising providing an orally ingestible delivery system as described above; administering the orally ingestible delivery system to the mammal by mouth; permitting passage of the orally ingestible delivery system into a stomach of the mammal, wherein the orally ingestible delivery system is exposed to stomach acid that digests the orally ingestible delivery system to form a partially-digested residue, and that interacts with the orally ingestible delivery system to form a dispersible gas barrier on a surface of the partially-digested residue, wherein the dispersible gas barrier protects the partially-digested residue from further digestion in the stomach; and permitting further passage of the partially-digested residue into the intestine, wherein the dispersible gas barrier is dispersed by interaction with bicarbonate secretions in the intestine and wherein enzymatic activity in the intestine erodes the partially-digested residue to release the therapeutic agent entrained therein, thereby delivering the therapeutic agent into the intestine. In embodiments, the mammal is a human patient in need of treatment with the therapeutic agent. In embodiments, the human patient is undergoing treatment with the therapeutic agent for a condition selected from the group consisting of cancers, metabolic disorders, allergic disorders, hormonal disorders, dermatological disorders, cardiovascular disorders, respiratory disorders, hematological disorders, musculoskeletal disorders, inflammatory disorders, rheumatological disorders, autoimmune disorders, gastrointestinal disorders, urological disorders, sexual and reproductive disorders, neurological disorders, and genetic disorders. In embodiments, the therapeutic agent, which can be a protein or a peptide or a living organism, is susceptible to degradation in the stomach.

As shown in the Figures that follow, certain embodiments of an orally ingestible delivery system are especially advantageous for food and drink applications.

Figure 14:
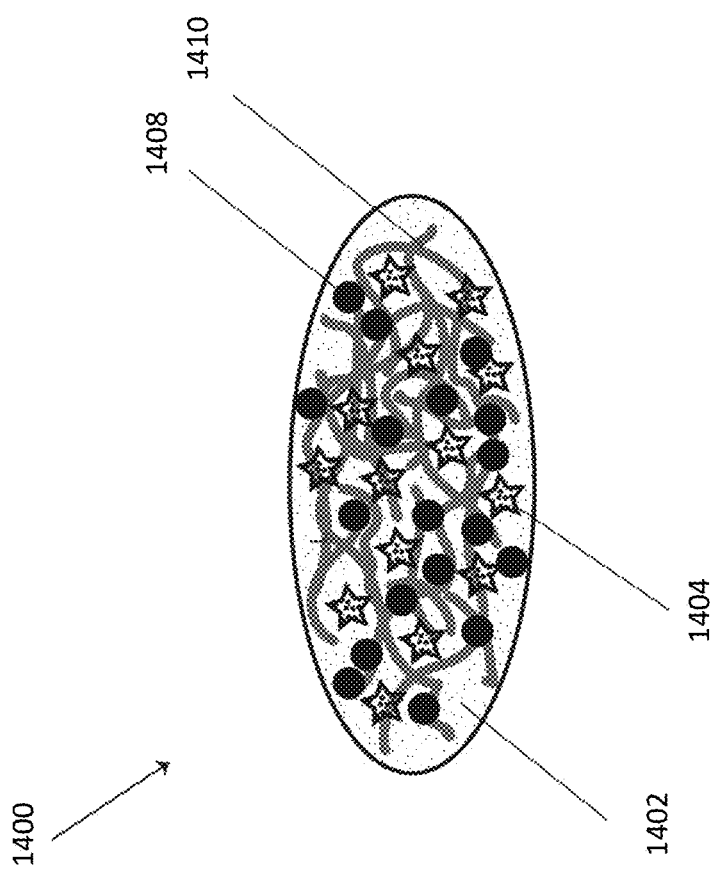
FIG. 14 depicts schematically an embodiment of an orally ingestible delivery system in cross-section.

FIG. 14 shows in cross section an embodiment of an orally ingestible delivery system 1400, comprising a hydrophilic matrix 1402 throughout which is dispersed discrete packets (e.g., particles, capsules, vesicles, or the like) of a therapeutic agent 1404 and throughout which is further dispersed a plurality of discrete packets (e.g., particles, capsules, vesicles, or the like) of a gas-forming substance 1408, and further comprising a hydrophobic framework 1410 that is disposed within the hydrophilic matrix 1402. As used herein, the term "packet" refers to a discrete deposit of the substance in question, which can be in an uncoated and unencapsulated form (a naked packet), or which can be encapsulated and/or coated with another material that wholly or partially envelopes the deposit of the substance in question. It is understood that the substances being delivered in packets can be in any physical state, including solids, liquids, gels, or combinations thereof as dispersions or emulsions.

The system 1400 is dimensionally adapted for ingestion, having a hydrophilic matrix 1402 that can be selected for its texture and taste, in order to optimize its gustatory appeal and its mouthfeel. Food-grade materials suitable for the matrix can include polysaccharides, such as starch (tapioca, rice, and corn, etc.), glycogen, inulin, pectin, xanthan gum, carrageenan, gum Arabic, agar, alginate, and the like, or protein solutions made from gelatin, wheat gluten, corn zein, soy protein, whey protein, and mung bean protein. Other examples of suitable matrix materials can be readily envisioned by skilled artisans in the field. In embodiments, the matrix can be coated with materials familiar to formulation scientists for coating traditional pills, in order to improve flavor or ingestibility, protect the underlying matrix, provide lubrication, etc. Representative coatings include, without limitation, magnesium stearate, calcium stearate, stearic acid, canuba wax, methacrylic acid copolymers, carboxymethyl cellulose polymers, cellulose acetate, polyvinylpyrrolidones, and mixtures of the aforesaid coating agents.

In embodiments, the hydrophilic matrix 1402 can be formed from hydrocolloids, which can be initially dehydrated following formation, and then rehydrated closer to the time of ingestion. As an example, a system 1400 having a matrix of a tapioca starch can be formed as spheres or "pearls" of jelly-like consistency. The pearls may then be sold in a dehydrated form, ready for addition into drinks (e.g., orange juice, sports drinks, or simply water). Upon hydration, the pearls (any size and shape, from sesame seed to pea size, for example, pearls or elongate strings or a designed "gummy" shapes) will hydrate and stay suspended in the drinks with simple stirring.

In other embodiments, the system 1400 is formed in its final shape and is then presented for ingestion without prior dehydration. Any ingestible form factor can be employed, and any consistency suitable for ingestion can be selected. For example, the matrix can be formed into a plurality of gelatinous spheres that can be swallowed in a liquid, such as a syrup or a drink. As another example, the matrix can be formed into an appealing shape for ingestion, like a gum drop or gummy bear, which can be chewed or swallowed whole. The system 1400 can be adapted for addition to virtually all food items (e.g., yogurt, cold soups, salads, jams, jellies, flavoring pastes, condiments, and the like), and virtually all drinks (e.g., ice tea, ice coffee, milk shakes, fruit juices, and the like).

Entrained within the hydrophilic matrix 1402 is a supportive framework 1410 comprising a hydrophobic material. The system 1400 is formed as a single structure, although it comprises two different types of materials, a hydrophilic material and a hydrophobic material, each of which is referred to herein as a "phase." Hence, the system 1400 itself is understood to be a monolithic three-dimensional object within which are distributed the two phases: the hydrophilic matrix 1402 and the hydrophobic framework 1410. This second, water-insoluble, acid-resistant phase can be chosen from a variety of hydrophobic materials, for example, cellulose, fatty acids, waxes, polyolefins, edible/natural elastomers (such as natural latexes, couma macrocarpa, tunu, jelutong, or chicle), and the like. Materials used as pharmaceutical excipients such as derivatized celluloses (e.g., methyl- or hydroxypropyl-substituted) or inert cellulosics (e.g., cellulose acetate, diacetate, and triacetate, etc.) are also suitable for forming the hydrophobic framework 1410. The framework 1410 itself does not require any particular structure: its shape can be organized as a network or intersection of components, or in any other shape that is based on the properties of the material or materials used for the hydrophobic phase. In embodiments, the framework 1410 can be formed as an integral unit having an appropriate regular or irregular shape, to be suspended or otherwise disposed within the matrix 1402. In other embodiments, the framework 1410 can be constructed or compiled from hydrophobic elements, for example any arrangement of hydrophobic fibers, shards, particles, composites, or other dimensionally suitable shapes that are arranged, for example, as networks, meshes, reticulations, cancellated or clathrate structures, and the like. The framework 1410 can be formed from a single hydrophobic component, or it can include multiple hydrophobic components; the framework 1410 can be continuous or discontinuous throughout the matrix. In embodiments, the hydrophobic framework 1410 can be formed from an active pharmaceutical ingredient that is itself hydrophobic. Optionally, the gas-forming substances 1408 can be attached, embedded in, or otherwise integrated with the hydrophilic framework.

A variety of manufacturing techniques are available to form the matrix 1402 and framework 1410 as described herein. For example, an aqueous phase comprising water, bicarbonate and bovine gelatin can be emulsified within a hydrophobic layer that comprises unrefined beeswax and polyisobutylene, and this emulsion can be used to form the system 1400. In such an emulsion, calcium carbonate gas-forming crystals can be suspended in the aqueous phase, as described below in more detail. The amount of polyisobutylene can be selected to provide desirable flexibility and integrity to the device, for example an amount ranging from about 0.5% to about 5%. In an embodiment, the emulsion can contain about 1% polyisobutylene. Additives such as fibers can be included in the emulsion to improve its structural strength. In embodiments, general hydrocolloids can be used to form the matrix 1402, with the hydrophobic phase embedded or formed therein. In embodiments, edible proteins such as whey protein, soy protein, or natural or partially hydrolyzed collagen can be used to form the matrix 1402. In embodiments, the matrix 1402 and framework 1410 two-phase system can be formed in which a hydrophobic layer is intertwined with a gel layer, with gas-forming substances 1408 and therapeutic agent packets 1404 disposed within the entire layer. In an embodiment, an emulsion can be formed within the matrix 1402 by mixing in a concentrated aqueous solution of bicarbonate; in embodiments, this emulsion technique can be combined with the process for combining the hydrophilic medium and the hydrophobic medium as they cooperate to form the hydrophobic framework 1410 within the hydrophilic matrix 1402, so that the gas-forming elements become dispersed throughout the system as it forms. Using this technique, the water within the aqueous phase of the emulsion can evaporate, leaving behind bicarbonate crystals as deposits of gas-producing substances 1408 within the matrix 1402.

In embodiments, the system can be formed having asymmetrical properties. For example, the matrix 1402 can be formed from a naturally derived polymer such as gelatin or an engineered polymeric matrix having embedded bicarbonate crystals within it, using techniques as described above. This hydrophilic matrix 1402 can then incorporate a hydrophobic framework material in a graded manner, so that more of the hydrophobic material is disposed peripherally and more of the hydrophilic material is disposed centrally. In embodiments, an asymmetrical arrangement of phases can be formed using temperature gradients that produce a gradient of the two dissimilar components, the hydrophilic phase and the hydrophobic phase. To create this asymmetrical arrangement, a mixture containing these two components can be placed between two different temperature boundaries, such that the mixing distribution of the component materials is a function of the temperature. This will allow the two components to become distributed differentially across the volume of the system, based on the response of each to the temperature gradient.

If the hydrophobic framework 1410 requires fortification, additional polymers can be added to the hydrophobic framework as the emulsion is being formed, where such additional polymers are selected that have advantageous mechanical properties, for example that improve the structural stability, integrity, rigidity or flexibility of the framework. For example, small amounts of a rubbery, hydrophobic polymer such as polyisobutylene can be added to increase structural stability and integrity. Other polymers such as polyethylene, polyisobutylene, polyvinyl acetate, and the like can be similarly added to the hydrophobic framework 1410 alone or in combination to improve its mechanical properties. For example, xanthan gum or other hydrophilic polymers can be combined with the hydrophobic framework materials. In embodiments, additives to the hydrophobic framework can include cellulose derivatives (e.g., hydroxypropyl cellulose, hydroxypropyl methyl cellulose, carboxymethylcellulose) and other hydrocolloids (pectin, pullulan, guar gum, xanthan gum, gum arabic, acacia gum, carrageenan, alginate, chitin, chitosan, starches, soy protein, whey protein, collagen, and gelatin), polypeptides, polyvinyl alcohol, polysaccharides and derivatives, hyaluronic acid, poloxamers, PEG, poly(N-vinylpyrrolidone); small molecules such as mono- and oligo-saccharides, water soluble salts, glycerol and edible surfactants (e.g., lauric arginate).

In embodiments, an orally ingestible delivery system 1400 can be formed having a water-swellable, acid-hydrolysable and/or protease-digestible hydrophilic phase, and a water-resistant and hydrolysis-resistant phase. Disposed within this system are the therapeutic agent packets 1404 and the gas-former packets 1408 described herein. In embodiments, the water-swellable acid-hydrolysable and/or protease-digestible phase can comprise polysaccharides, proteins, or some combination thereof. Polysaccharides familiar in the art, such as starch (tapioca, rice, and corn, etc.), glycogen, inulin, pectin, xanthan gum, carrageenan, gum Arabic, agar, alginate, and the like can be used for this phase. In embodiments, polysaccharides having hydrocolloidal properties may be selected in order to exploit their ability to swell upon exposure to water. Proteins such as gelatin, wheat gluten, corn zein, soy protein, whey protein, and mung bean protein, can be used for this phase, and can form water-swellable protein solutions. Gas-producing substances 1408 and the therapeutic agent packets are dispersed within this phase. The water-insoluble, acid-resistant phase can be formed from a variety of substances, for example cellulose, fatty acids, waxes, polyolefins, edible/natural elastomers (such as natural latexes, couma macrocarpa, tunu, jelutong, or chicle). This water-insoluble, acid-resistant phase can also comprise non-digestible food-grade materials such as fibers intended to improve the strength and durability of this layer.

In embodiments, fibers (not shown) can be added to the matrix 1402 or to the hydrophilic framework 1410 to improve strength, elasticity, or durability. Edible fibers, for example certain vegetable-derived fibers, are particularly advantageous, for example fibers derived from the skin or bast surrounding the stem of a plant or from the fruit of a plant (e.g., banana fibers, coconut fibers, soybean fibers, and the like), or fibers derived from leaves or plant stalks (e.g., wheat, rice, barley, grass, and the like). Fibers can be admixed with the hydrophobic phase or with the aqueous phase, or fibers can be used to construct a reinforcement or support structure to which a hydrophobic material can be applied in order to create the hydrophobic framework 1410. In embodiments, the hydrophobic material can be applied to a preformed latticework, where the lattice is formed from a stiffer wax, a polymeric network, or fibers. In embodiments, the lattice can be formed with defibrillated fibers coated with wax, fat, or fatty acids, with the lattice then coated with the hydrophobic substrate for the outer acid-resistant layer. Gas-forming substances 1408 can be included within the hydrophobic material that is applied to the lattice, or the gas-forming substances 108 can reside within the interstices of the lattice, being positioned there before the lattice is coated with the hydrophobic material, after the lattice is coated with the hydrophobic material, or both. For example, a lattice can be formed first, then coated with the water-in-wax emulsion previously described, wherein the water phase of the emulsion contains a concentrated aqueous solution of bicarbonate; as the water evaporates, the bicarbonate remains where it was carried by the emulsion, for example within the valleys and voids of the lattice structure, and it crystallizes as water is lost from the concentrated aqueous solution. In other embodiments, the gas-producing substances 1408 can be attached to fibers within the matrix 1402, so that as the fibers are digested by the stomach acid, the acid also contacts the gas-producing substances and activates them, resulting in the formation of a dispersible gas barrier as shown below in FIG. 15.

Embedded within the matrix are two sets of packets: packets of therapeutic agents 1404 and packets of gas-forming substances 1408. As used herein, the term "packet" refers to any sort of visible or subvisible structure dimensionally adapted to contain the substance in question, whether therapeutic agent or gas-forming. A "packet" can be formed integrally from the substance itself, or it can be formed as a capsule, envelope, or other container within which the substance is contained. In embodiments, the packets range from about 0.01 microns up to about 1 micron in size, and they can be regularly or irregularly formed, and can be formed in any convenient shape, including but not limited to spherical, cuboidal, trapezoidal, linear, fibrillar, flake-like, entangled, elongate, cylindrical, tapered, or uniform shapes, and combinations thereof. In all embodiments, the packets are substantially smaller in size than the size of the delivery system itself. In embodiments, there can be hundreds or thousands of packets within the matrix for a particular substance.

The size and shape of the packets is such that a multitude of packets can be suspended in the matrix, permitting dispersion of the substance throughout the matrix in a random or regular pattern. For example, the packets can be dispersed fairly uniformly throughout the matrix, or the packets can be arranged preferentially in particular areas. For example, the gas-former packets 1408 can be deployed closer to the surface of the system 1400, while the therapeutic agent packets 1404 can be concentrated more centrally. Other arrangements of the packets can be envisioned by skilled artisans in order to achieve the therapeutic objectives of the system, as is described below in more detail. Gas-former packets 1408 contain gas-producing substances in solid or liquid form that produce gas when exposed to stomach acid. As used herein, the term "gas former" or "gas-forming substance" refers to a material selected so that it produces a gas when it reacts with acid, such as is found in the gastric juice. Of particular advantage is a gas-forming substance that generates carbon dioxide upon exposure to the hydrochloric acid in the stomach. Gas-forming substances (e.g., carbon-dioxide formers such as calcium carbonate (including precipitated calcium carbonate (PCC)), sodium bicarbonate, potassium bicarbonate, magnesium carbonate, and the like, or hydrogen formers such as magnesium particles and the like) exist as solid materials or in other physical states that can, in embodiments, be implanted in packets in the matrix to release carbon dioxide when exposed to stomach acid. In an embodiment, the gas-forming substance can be embedded in a digestible polymer or small molecule carrier that is disposed within the matrix, so that upon contact with stomach acid the carrier decomposes and exposes the embedded gas-forming substance to react with the stomach acid.

As an example, precipitated calcium carbonate (PCC) generates carbon dioxide when exposed to the hydrochloric acid in the stomach. PCC particles disposed within the matrix 1402 come into contact with stomach acid as the outer layers of the matrix 1402 are hydrolyzed by the stomach acid and eroded. Carbon dioxide is formed when the stomach acid contacts the PCC crystals. While some of the carbon dioxide disperses freely into the stomach juice, other $CO_2$ bubbles arrange themselves on the surface of the eroded matrix and form a protective barrier. This process is shown in more detail in FIG. 16 below.

The matrix 1402 also contains a plurality of packets 1404 containing the therapeutic agent. In embodiments, the distribution of the therapeutic agent packets 1404 is preselected so that a desired amount of the therapeutic agent is distributed within the matrix 1402 based on the density of therapeutic agent packets within the matrix 1402. These therapeutic agent packets 104 are vulnerable to stomach acid hydrolysis, as is the matrix 1402 surrounding them. Hence, if the matrix 1402 is eroded by contact with stomach acid, some of the therapeutic agent packets 1404 can be hydrolyzed as well. However, those therapeutic agent packets 1404 disposed more internally within the matrix 1402 can be preserved beneath the layer of carbon dioxide that accumulates on the surface of the system 1400, as shown in more detail in FIG. 15.

It is understood that, in embodiments, a regular distribution of therapeutic agent packets 1404 throughout the matrix 1402 can permit the therapeutic agent to be released uniformly even if the integrity of the system 1400 is breached, for example by chewing. If the matrix 1402 is intended for chewing, it is broken up into smaller pieces, each of which contains an amount of therapeutic agent packets 1404 and gas former packets 1408 based on the density of those packets within the matrix and also based on the volume of each chewed piece. With a homogenous distribution of therapeutic agents 1404 and gas former packets 1408 within the matrix, chewing simply divides the total volume of the system 1400 into subunits and does not impair the function of the packets suspended therein: chewing simply breaks the larger system 1400 into smaller particles, each of performs similarly to the larger system 1400 upon encountering stomach acid (as is described below in more detail).

Figure 15:
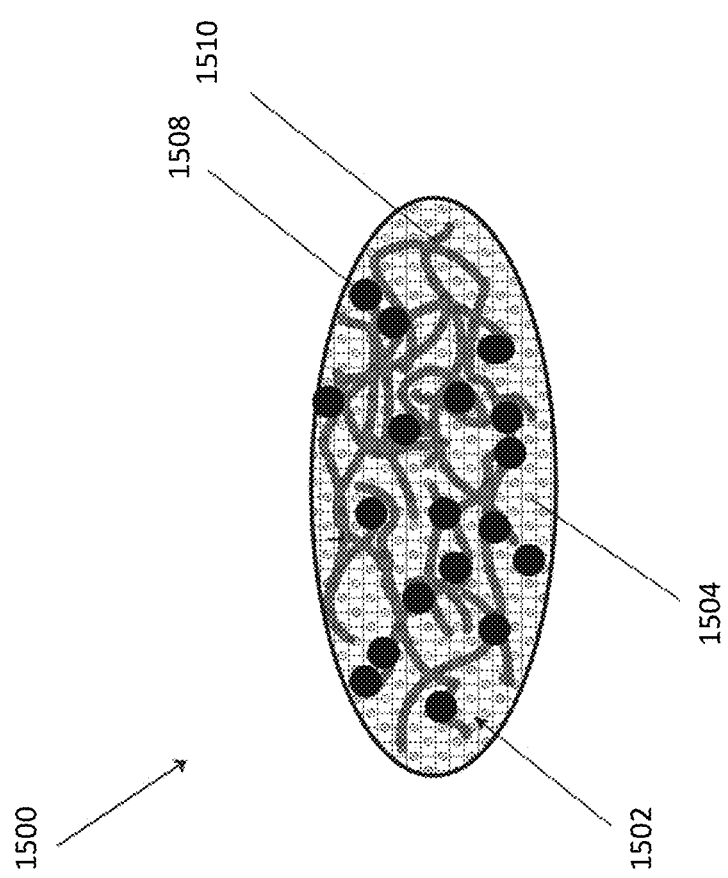
FIG. 15 depicts schematically an embodiment of an orally ingestible delivery system in cross-section.

FIG. 15 shows a cross-section of an embodiment of an orally ingestible delivery system 1500 comprising a hydrophilic matrix 1502 within which a therapeutic agent is dissolved or dispersed, with the therapeutic agent 1504 being integrated within the matrix 1502 itself. In this embodiment, the therapeutic agent 1504 is not contained in discrete packets, but rather is entrained within the matrix 1502. Also dispersed within the matrix 1502 are also a plurality of discrete packets (e.g., particles, capsules, vesicles, or the like) of a gas-forming substance 1508. Embedded within the matrix is a hydrophobic framework 1510. Optionally, the gas-forming substances 1508 can be attached, embedded in, or otherwise integrated with the hydrophilic framework. The hydrophilic framework 1510 in the depicted embodiment is substantially similar in its composition and configuration to that described with reference to FIG. 14.

Figure 16:
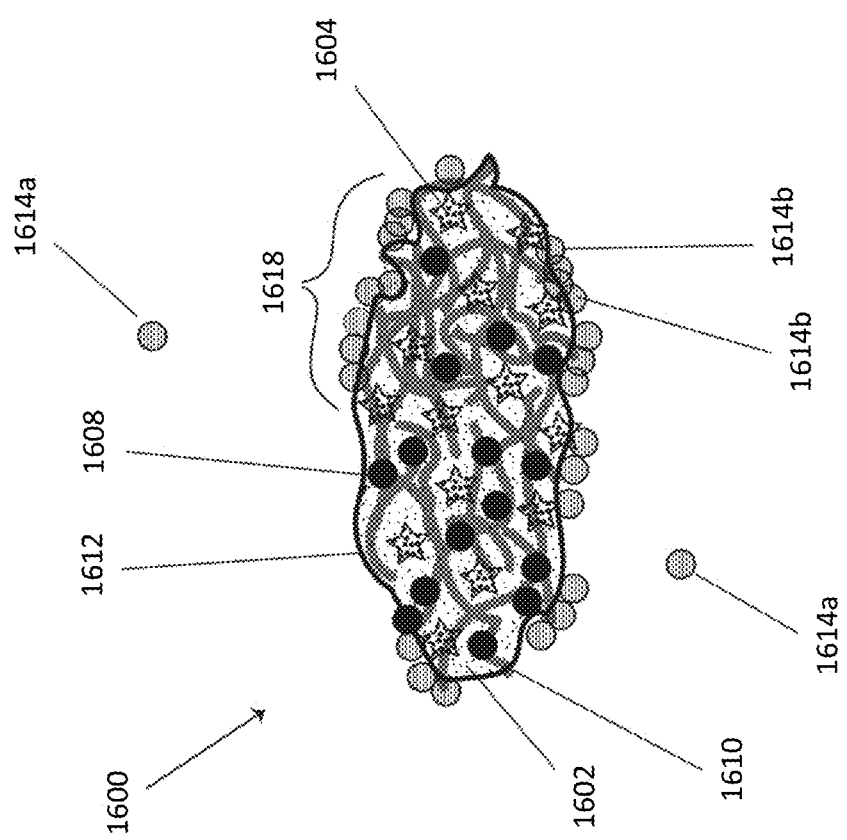
FIG. 16 depicts schematically an embodiment of an orally ingestible delivery system in cross-section, following a period of residence in the stomach.

FIG. 16 shows a cross-section of an embodiment of an orally ingestible delivery system 1600 as depicted in FIG. 14, following its ingestion and after a period of residence in the stomach. As shown in this Figure, the orally ingestible delivery system 1600 comprises a hydrophilic matrix 1602 throughout which is dispersed discrete packets of a therapeutic agent 1604, and throughout which is further dispersed a plurality of discrete packets (e.g., particles, capsules, vesicles, or the like) of a gas-forming substance 1608. The system 1600 comprises a hydrophobic framework 1610 that is disposed within the hydrophilic matrix 1602. The shape of the system 1600, as shown schematically in FIG. 16, reflects the effects of exposure to the hydrochloric acid in the stomach: as compared to the orally ingestible delivery system shown in FIG. 14, the surface 1612 of the system 1600 is irregular, and the volume of the matrix is decreased, reflecting the erosion of the matrix 1602 by contact with the stomach acid. The integrity of the system 1600 is maintained by the hydrophobic framework 1610 embedded within the matrix 1602. This framework 1610 is not affected by the stomach acid, and thus provides structural support.

As further depicted in FIG. 16, certain of the gas-former packets 1608 still reside within the matrix 1602, as they have not yet been reached by the stomach acid. Certain other gas-former packets have been contacted by the stomach acid and have released gas bubbles 1614a and 1614b; for example, with a PCC gas former, the gas bubbles 1614a and 1614b are carbon dioxide gas. Certain of the gas bubbles 1614a are released within the stomach juice, while others retain contact with the surface 1612 of the system 1600. As the erosion continues, more of the gas-former packets 1608 contact the stomach acid and release gas bubbles 1614b that reside on the system's surface 1612. These bubbles 1614b coalesce to form a dispersible gas barrier 1618 that then protects the underlying matrix 1602 and the therapeutic agent packets 1604 contained therein. After the acid erosion depicted in FIG. 16, some of the more superficial therapeutic agent packets have been hydrolyzed or digested, as they encountered the stomach acid before the dispersible gas barrier 1618 formed. However, with the consolidation of the dispersible gas barrier 1618, the remaining therapeutic agent packets 1604 can be protected.

As shown in FIG. 16, certain gas-former packets 1608 remain within the matrix 1602 and are not in contact with stomach acid. Hence, in the depicted embodiment, their protective effect is lost because their gas forming potential is not activated. In embodiments, the gas-former packets 1608 and the therapeutic agent packets 1604 are distributed substantially uniformly throughout the matrix 1602. This arrangement is advantageous for use with chewable systems, because the gas-former packets 1608 and the therapeutic agent packets become proportionally distributed in the smaller volumes of the chewed pieces, so that the delivery of therapeutic agent from each chewed piece is proportionally uniform. However, this uniform distribution, with packets distributed relatively evenly throughout the matrix 1602 can place a certain proportion of the therapeutic agent packets 1604 more superficially, so that they are vulnerable to attack by stomach acid. In such an arrangement, those more superficial therapeutic agent packets 1604 are sacrificed as the stomach acid erodes the matrix; thus their contents are destroyed and not delivered to the patient in need thereof. As an alternative, in certain embodiments, there can be a differential arrangement of gas-former packets 1608 and therapeutic agent packets 1604, so that the gas-former packets 1608 are more superficial while the therapeutic agent packets 1604 are buried more deeply. This arrangement allows the more superficially positioned gas-former packets to encounter the stomach acid first, and to form the dispersible gas barrier 1618, before the matrix 1602 is sufficiently eroded to expose the therapeutic agent packets 1604 to the deleterious effect of the stomach acid. In other embodiments, the matrix 1602 can be penetrated by a plurality of pores or channels (not shown) that can allow the stomach acid to penetrate the matrix via the pores or channels, and to react with the gas-formers 1608 located in the matrix interior. In yet other embodiments, the system 1600 can include fibers or other conduits that wick the stomach acid into the matrix 1602 so that the interior gas-formers 1608 can be activated.

The dispersible gas barrier 1618 that forms on the surface 1612 of the system 1600 protects the remnants of the matrix 1602 and the therapeutic agent packets 1604 dispersed therein from the stomach acid and the stomach's digestive enzymes. For the therapeutic agent to be released from the system, however, the dispersible gas barrier 1618 must be dispersed. This takes place in the duodenum, as is described below. Carbon dioxide is particularly advantageous as the main component of the dispersible gas barrier 1618 because it dissolves in the neutral secretion of the intestine and reacts with the bicarbonates that are released in the pancreatic secretions. This feature allows a carbon dioxide gas barrier that has been formed in the stomach by the action of the stomach acid on the gas-producing substance to be rapidly dispersed in the duodenum, allowing the ingress of the various pancreatic enzymes into the acid-resistant protease-digestible membrane, as will be described below in more detail.

As shown in FIG. 16, the outer aspect of the matrix 1602 of the orally ingestible delivery system 1600 has been eroded due to acid digestion, with loss of matrix material and loss of some of the therapeutic agent 1604. In order to control for the loss of the therapeutic agent 1604 in the stomach, the system 1600 can be engineered to decrease the erosion of the superficial layer of the matrix 1602. As described above, the system 1600 can be designed with a differential allocation of the hydrophobic and hydrophilic components or the gas formers 1608, so that more of the hydrophobic material and/or more of the gas formers 1608 are located peripherally to resist acid hydrolysis. Also, as described above, the therapeutic agent 1604 can be positioned more centrally, so that it is not as accessible to digestion even as the periphery of the matrix 1602 is digested. In embodiments, additives can be incorporated into the matrix 1602 as a whole, or into the outer portions of the matrix 1602 that improve its acid resistance. In embodiments, the matrix can include agents that impair its digestibility when exposed to proteases, thereby protecting the therapeutic agent 1604 contained within. For example, if the matrix 1602 is formed with gelatin, the delaying substances can be formulated within the gelatin itself.

As would be further understood by skilled artisans, the decomposition time of the matrix 1602 can be further adjusted by adding coatings on top of it, for example a coating possessing delayed release or extended release properties when exposed to stomach acid and/or proteases. Techniques for forming such layers are well-known in the art. In certain embodiments, enteric coatings can be applied to the therapeutic agent packets 1604 so that they are protected from the conditions in the small intestine, thereby allowing the therapeutic agent 1604 to reach a desired location distal to the duodenum, for example, in the jejunum, ileum, or colon. While a wide range of conventional enteric coating formulations can be used, it is envisioned that protective coatings for the therapeutic agent packets 1604 can be selected that are less robust than those materials or thicknesses used for conventional enteric coatings. This is because traditional enteric coatings require greater durability so that they can resist the harsh conditions in the stomach, including acid and protease induced hydrolysis. By contrast, the gas barrier 1618 that forms in the stomach protects the system 1600 from hydrolysis. Therefore, there is a lower performance demand for the enteric coatings that are applied to the therapeutic agent packets 1604, as compared to conventional enteric coatings. Thus, in embodiments an enteric coating can be used that would be considered rather "weak" in resisting acidic- and protease-degradation. In other embodiments, the enteric coating for the therapeutic agent 1604 can be specifically designed for the conditions in the intestine. For example, bile secretion releases copious amounts of lipase and surfactants in addition to protease. Thus, the modified release layer can be a lipid-based formulation, degradable by lipase at neutral pH at a predictable rate. Alternatively, traditional enteric coatings can be employed, but as a thinner than normal layer.

In embodiments, coatings to be applied to the entire system can be selected to improve the ingestibility of the system, to improve its palatability, or to protect it from mechanical trauma. For example, confectioner's glaze or pharmaceutical glaze can provide a glossy finish and protective coating around the entire device. Such coatings are well-known in the formulation field. Such coatings can be formed from natural ingredients, such as shellac (formed from insect excretions) and carnauba wax.

Figure 17:
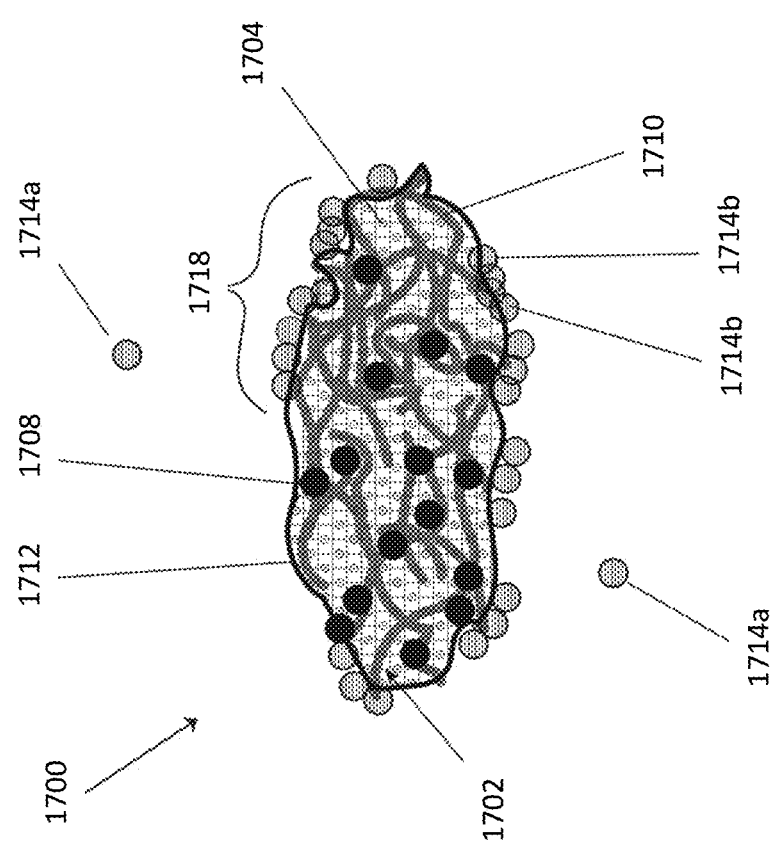
FIG. 17 depicts schematically an embodiment of an orally ingestible delivery system in cross section, following a period of residence in the stomach.

FIG. 17 shows a cross-section of an embodiment of an orally ingestible delivery system 1700 as depicted in FIG. 15, following its ingestion and after a period of residence in the stomach. As shown in this Figure, the orally ingestible delivery system 1700 comprises a hydrophilic matrix 1702 throughout which are dispersed a plurality of discrete packets (e.g., particles, capsules, vesicles, or the like) of a gas-forming substance 1708. The therapeutic agent is dissolved or dispersed within the hydrophilic matrix. The system 1700 further comprises a hydrophobic framework 1710 that is disposed within the hydrophilic matrix 1702. The shape of the system 1700, as shown schematically in FIG. 17, reflects the effects of exposure to the hydrochloric acid in the stomach: as compared to the orally ingestible delivery system shown in FIG. 16, the surface 1712 of the system 1700 is irregular, and the volume of the matrix is decreased, reflecting the erosion of the matrix 1702 by contact with the stomach acid. The integrity of the system 1700 is maintained by the hydrophobic framework 1710 embedded within the matrix 1702. This framework 1710 is not affected by the stomach acid, and thus provides structural support.

As further depicted in FIG. 17, certain of the gas-former packets 1708 still reside within the matrix 1702, as they have not yet been reached by the stomach acid. Certain other gas-former packets have been contacted by the stomach acid and have released gas bubbles 1714a and 1714b; for example, with a PCC gas former, the gas bubbles 1714a and 1714b are carbon dioxide gas. Certain of the gas bubbles 1714a are released within the stomach juice, while others retain contact with the surface 1712 of the system 1700. As the erosion continues, more of the gas-former packets 1708 contact the stomach acid and release gas bubbles 1714b that reside on the system's surface 1712. These bubbles 1714b coalesce to form a dispersible gas barrier 1718 that then protects the underlying matrix 1702 and the therapeutic agent dispersed in the matrix 1702. After the acid erosion depicted in FIG. 17, more superficial regions of the matrix 1702 have been hydrolyzed or digested, as they encountered the stomach acid before the dispersible gas barrier 1718 formed; as the matrix 1702 is eroded, the therapeutic agent contained therein is destroyed as well. However, with the consolidation of the dispersible gas barrier 1718, the remaining matrix 1702 and therapeutic agent dispersed therein can be protected. In embodiments, the therapeutic agent within the matrix 1702 is arranged evenly, so that erosion of the superficial matrix 1702 results in a comparable loss of therapeutic agent. In other embodiments, there is a differential localization of the therapeutic agent within the matrix 1702, for example with a greater concentration of the therapeutic agent more centrally, and less or no therapeutic agent contained in the more superficial matrix 1702. In this arrangement, the digestion or hydrolysis of the superficial matrix 1702 would have less effect on the overall concentration of the therapeutic agent within the system 1700 following exposure to stomach acid: the portion of the matrix 1702 that is eroded by the stomach acid contains relatively less therapeutic agent than the portion of the matrix 1702 that has been protected so that it remains undigested.

As was described in conjunction with FIG. 16, there can be a differential arrangement of gas-former packets 1708 in certain embodiments, so that more of the gas-former packets 1708 are located more superficially within the matrix 1702. This differential arrangement of gas-former packets 1708 can, in embodiments, be combined with a differential localization of the therapeutic agent within the matrix 1702, as previously described, so that there is, for example, a greater concentration of therapeutic agent more centrally in the matrix 1702. If the gas-former packets 1708 are located more superficially, they will encounter the stomach acid first and form the dispersible gas barrier 1718, which then will protect the remaining matrix 1702 and the therapeutic agent disposed therein. If the superficial positioning of the gas-former packets 1708 is combined with a differential and more central localization of the therapeutic agent in the matrix 1702, this affords additional protection to the therapeutic agent, preventing more of its loss to stomach acid erosion as compared to a homogenous dispersal of therapeutic agent throughout the matrix 1702. In embodiments, the matrix 1702 can be penetrated by a plurality of pores or channels (not shown) that can allow the stomach acid to penetrate the matrix via the pores or channels, and to react with the gas-formers 1708 located in the matrix interior. In yet other embodiments, the system 1700 can include fibers or other conduits that wick the stomach acid into the matrix 1702 so that the interior gas-formers 1708 can be activated.

The dispersible gas barrier 1718 that forms on the surface 1712 of the system 1700 protects the remnants of the matrix 1702 and the therapeutic agent disposed therein from the stomach acid and the stomach's digestive enzymes. As was described in conjunction with FIG. 16, carbon dioxide is particularly advantageous as the main component of the dispersible gas barrier 1718 because it dissolves in the neutral secretions of the intestine and reacts with the bicarbonates that are released in the pancreatic secretions. This feature allows a carbon dioxide gas barrier that has been formed in the stomach by the action of the stomach acid on the gas-forming substances to be rapidly dispersed in the duodenum, allowing the ingress of the various pancreatic enzymes into the acid-resistant protease-digestible membrane, as will be described below in more detail.

The Figures above depict embodiments of orally ingestible delivery systems that are assumed to be ingested orally in a relatively intact form (with allowance made for chewing or intra-oral dissolution). As a result of the system's encounter with stomach acid, the matrix is digested, with exposure of gas-formers within the matrix to the stomach acid so that they form gas bubbles that coalesce on the surface of the system and provide the dispersible gas barrier. In embodiments, however, the orally ingestible delivery system can encounter an acid milieu prior to its ingestion, and it would respond to that exposure similarly to how it responds to stomach acid. For example, the orally ingestible delivery system can be provided in an acid milieu for ingestion, or it can be swallowed along with an acid liquid, gel or solid. The pre-stomach contact with acid initiates the mechanisms for producing the dispersible gas barrier, whether within the stomach or before it reaches the stomach. If the ingestible delivery system has been exposed to acid prior to reaching the stomach, it is understood that further contact with stomach acid can continue the reactions with the gas formers in the matrix that produce the dispersible gas barrier.

In embodiments, the delivery system can be engineered to optimize precision dosage of the therapeutic agent or agents. It is understood that there is some erosion of the outside of the matrix within which the therapeutic agent is dissolved or dispersed. If some of the therapeutic agent resides in the outer aspect of the matrix (as therapeutic agent packets or dissolved in the matrix), it is subject to degradation (e.g., digestion, denaturation, inactivation, loss of therapeutic efficacy, instability, or other deleterious effects) if it encounters stomach acid or enzymes. As mentioned previously, a differential deployment of the therapeutic agent and/or the gas former packets can aid in the protection of the therapeutic agent within the device. In embodiments, the therapeutic agent can be deployed more centrally within the matrix, so that it escapes an encounter with the gastric juice while the outer portions of the matrix are digested. In other embodiments, there can be a preponderance of gas former packets in the outer portions of the matrix, so that they are activated by the stomach acid to form the dispersible gas barrier, which in turn protects the therapeutic agent within the matrix.

In yet other embodiments, the calculation of delivered dose for the therapeutic agent can include a correction for the amount of the therapeutic agent originally contained in the matrix that is sacrificed by its encounter with the stomach juices. In embodiments, the amount of the matrix that is digested can be calculated in advance, and the load of therapeutic agent can be adjusted so that the desired dose is administered after accounting for some loss during matrix digestion. Certain mathematical models permit an approximation of matrix loss; empirical methods can also be employed to provide more precise information.

In embodiments, a variety of doses of therapeutic agents can be administered by adjusting the size or shape of the delivery system itself. For example, the matrix can be shaped as a flat ribbon or an elongate strand or a hollow cylinder with the therapeutic agent dispersed or dissolved therein in a uniform manner. An appropriate dosage of the therapeutic agent can then be provided by cutting the ribbon/strand/cylinder to a certain length. For example, in a 5 cm long dosage form containing 100 mg of the therapeutic agent homogeneously distributed within the matrix, a 1 cm long piece would contain 20 mg of the therapeutic agent.

In another embodiment, the delivery system can be shaped into symmetrical three-dimensional objects such as spheres or ovals, with the amount of therapeutic agent in a particular object varying with the volume of the object. For example, a sphere having a radius of 5 mm has a volume of about 0.52 $cm^3$; if the matrix has a concentration of 100 mg per $cm^3$, this sphere contains about 52 mg. A sphere of this size can be suitable for swallowing whole, or it can be chewed. If chewing is to be avoided, the spheres can be made smaller, and the same dose can be achieved by swallowing a larger number of smaller spheres. In this case, a sphere having a radius of 2 mm has a volume of about 0.033 $cm^3$ and contains about 3.3 mg of the therapeutic agent if that agent is present in the matrix at a concentration of 100 mg per $cm^3$. About 16 of the 2 mm-radius spheres would need to be ingested to provide the same dosage of therapeutic agent as the single 0.5 cm radius sphere. However, the plurality of 2 mm radius spheres may be much more suitable for swallowing whole, for example suspended in a liquid or in a food substance that is easy to swallow. Even smaller spheres, ovoids, rods, etc., can lend themselves to even easier ingestion. While symmetrical three-dimensional objects have been described above for illustrative purposes, the three-dimensional delivery systems can be constructed asymmetrically, or molded into attractive shapes, or otherwise fabricated using techniques familiar to pharmaceutical manufacturers, confectioners, and the like.

In embodiments, the delivery system can be coated with a lubricious and/or pleasant-tasting coating (e.g., confectioner's glaze, canuba wax, gelatin, mucilage, and the like) that make its ingestion easier. In embodiments, the delivery systems can be ingested along with a liquid, gel, or solid to facilitate swallowing them. For those delivery systems dimensionally adapted for swallowing whole, adjustments may still need to be made for erosion within the stomach that decreases the delivered dose of the therapeutic agent. An additional challenge for delivery systems intended for chewing, is the fragmentation of the single dosage form into multiple chewed fragments. Following chewing, each of the fragments will contain a portion of the original administered dosage based on the volume of the fragment, but the therapeutic agent residing in each fragment can be attacked by stomach acid and enzymes differently, depending for example on the surface area or the configuration of the fragment. Therefore, chewable delivery systems are particularly suitable for therapeutic agents that do not require precise dosage. For chewable delivery systems that contain therapeutic agents requiring more precise dosage, the dosage amount will require empirical investigation or mathematical modeling to ensure that an appropriate amount of the administered therapeutic agent is available to the patient following passage of the chewed fragments through the stomach.

B. Methods of Treatment Using Orally Ingestible Delivery Systems

1. Definitions and Overview

As used herein, the terms "treatment," "treating," "therapy," "therapeutic" and the like can refer to interventions that are intended to cure, heal, alleviate, improve, remedy, diagnose, or otherwise beneficially affect a disorder or a condition that impacts the well-being of a human person or an animal. A disorder is any condition that alters the homeostatic well-being of a human person or an animal, including but not limited to acute or chronic diseases, or pathological conditions that predispose the mammal to an acute or chronic disease. Non-limiting examples of disorders include cancers, metabolic disorders (for example, diabetes), allergic disorders (for example, asthma), hormonal disorders, dermatological disorders, cardiovascular disorders, respiratory disorders, hematological disorders, musculoskeletal disorders, inflammatory or rheumatological disorders, autoimmune disorders, gastrointestinal disorders, urological disorders, sexual and reproductive disorders, neurological disorders, genetic disorders, and the like. As used herein, the term "condition" includes disorders and non-pathological conditions that are nonetheless characterized by susceptibility to a particular disease or condition. The term "condition" also includes states of wellness in a human person which can be improved, enhanced, or otherwise altered favorably, to the subjective benefit of such person. As used herein, the term "patient" is any person or animal affected by a disorder; the term "patient" can refer in context to any mammal, including humans, domestic animals, pet animals, farm animals, sporting animals, working animals and the like. A patient can be of any age, including mammals in utero. Patients in need of a treatment include both those who already have a specific disorder or condition, whether or not symptomatic, and those for whom prevention of a disorder is desirable.

As used herein, the term "treatment," "treating," "therapy," "therapeutic," and the like can refer to interventions that are intended to diagnose disorders or conditions, or otherwise evaluate the status of disorders or conditions in a patient. Such diagnosis or evaluation can include any sort of intervention, procedure, or process gathers information in order to delineate the state or status of a disorder or a condition. For example, a diagnosis or evaluation can take place using the methods of biology, chemistry, or physics. Exemplary and non-limiting biological methods for diagnosis or evaluation include techniques such as biopsying an area, collecting exfoliated cells from an area, testing a tissue's response to a certain stimulus, and the like. Exemplary and non-limiting chemical methods for diagnosis or evaluation include measuring chemical parameters in bodily fluids or in biological samples, and the like. Exemplary and non-limiting physical methods include visual inspection via direct visualization or image capture, diagnostic imaging via scans, ultrasound, X rays, and the like.

Under appropriate circumstances, the terms "treatment," "treating," "therapy," "therapeutic" and the like can refer to interventions that are intended to promote wellness or other desirable physical or psychological states in a human or non-human subject, so that a "treatment," "therapy," and the like can refer to an intervention that has pleasurable, psychotropic, or other non-medical, holistic, or recreational effects. Examples of such "treatment," "therapy," and the like can include various nutraceuticals or wellness agents intended to improve a subject's sense of well-being and health. Other examples of such "treatment," "therapy," and the like can include substances ingested for recreational, hedonistic, or sensual purposes such as marijuana, marijuana-derived substances, certain cannabinoids, and the like. While medical marijuana, synthetic cannabinoid products such as dronabinol (Marinol® marketed by Unimed) or the cannabidiol (CBD) preparation Epidiolex® (marketed by GW Research Ltd.), and generic cannabidiol "over the counter" preparations have usefulness in treating diseases or disorders, whole-plant marijuana or preparations including the psychotropic cannabinoid delta-9-tetrahydrocannabinol (THC) can be used for non-medical, recreational, or wellness/wellbeing-inducing purposes. Such substances, whether achieving a medical or a non-medical effect, are deemed "treatments," "therapies," etc. for the purposes of this disclosure.

In embodiments, a treatment involves providing a therapeutically effective amount of a therapeutic agent to a patient in need thereof. A "therapeutically effective amount" is at least the minimum concentration of the therapeutic agent administered to the person or animal in need thereof, to effect a treatment of an existing disorder or a prevention of an anticipated disorder (either such treatment or such prevention being a "therapeutic intervention").

A wide range of therapeutic agents are suitable for deployment within the orally ingestible delivery systems described herein. One or more therapeutic agents can be included within the orally ingestible delivery system, using formulation methods familiar to skilled artisans. In embodiments, therapeutic agents are pharmaceutical, nutraceutical (i.e., a pharmaceutical alternative claiming physiological benefits), or diagnostic agents that are formulated for delivery in a liquid, semi-solid, or solid form, or any combination thereof. Solid forms can include powders, pellets, crystals, and the like. Semi-solid forms can include slurries, pastes, gels, gums, and the like. Formulations of therapeutic agents can be produced using familiar techniques in the art, including excipients designed to enhance their physical properties, their uptake rates, their delayed or controlled release, and the like. The therapeutic agents can be enclosed in other membranes or layers intended to encapsulate them, protect them from dissolution, prolong their release, or other adaptations familiar to skilled artisans.

In more detail, therapeutic agents for deployment within the orally ingestible delivery systems described herein can be formulated as dosage forms for immediate release or for modified release. As used herein, the term "dosage form" denotes any form of a formulation that contains an amount of a therapeutic agent sufficient to achieve a therapeutic effect with a single administration. A dosage form may be engineered to provide an immediate release of the active pharmaceutical ingredient, or a modified release of the active pharmaceutical ingredient, or a combination of release patterns.

As used herein, the term "immediate release" refers to a dosage form or delivery system in which the active pharmaceutical ingredient (API) is released from the dosage form with a rapid dissolution profile attained promptly after administration. While the term "immediate release" often refers simply to highly soluble APIs, comparable immediate release profiles can be achieved with less soluble therapeutic agents if excipients such as surfactants are added to the formulation to enhance drug dissolution. A therapeutic agent delivered via the orally ingestible delivery system and intended for immediate release can pass across the intestinal mucosal boundary via mechanisms such as passive diffusion or active transport, reaching its highest plasma level (termed $C_{max}$) in a fairly short time (termed $T_{max}$). Immediate release dosage forms usually release the therapeutic agent in a single action, following a first-order kinetics profile in which the rate of the process is proportional to the concentration of the therapeutic agent.

To counteract the disadvantages of immediate release dosage forms, or to achieve discrete therapeutic results, dosage forms can be designed that modify the release profile of the therapeutic agent. As used herein, the term "modified release" for a formulation or a composition refers to any dosage form that delivers the therapeutic agent at a rate that differs from immediate release as described above. Modified release dosage forms have drug-release characteristics that differ from immediate release dosage forms in time course or in release location. Modified dosage forms can be further classified as "delayed release," wherein the drug is released at a point in time and/or at a location that differs from the time and location of initial administration, and "extended release," wherein the drug's release is prolonged over time as compared to an immediate release version.

In embodiments, therapeutic agents used with the orally ingestible delivery systems described herein can be further coated (e.g., with enteric coatings) to delay release of the therapeutic agent even after it has been released from the delivery system. Delayed release modifications can allow a therapeutic agent released from the delivery system in the small intestine to pass further along the gastrointestinal tract, for uptake at a preselected anatomical location. For example, an oral dosage form can be enteric-coated, to delay release of the medication until the formulation has passed through the stomach, or until the drug has passed through the gastrointestinal tract to the colon. Typically, extended release dosage forms are formulated in such a manner as to make the therapeutic agent available over an extended period of time following administration. Extended release dosage forms can be further characterized as sustained release or controlled release. Sustained release systems maintain the rate of drug release over a prolonged period of time. Sustained release dosage forms can permit the therapeutic agent to release gradually, for example, along the entire small intestine, resulting in a prolonged period for absorption and a consequent prolonged interval of drug concentration in the therapeutic range. Sustained release dosage forms commonly use various polymers that coat granules or tablets, or that form a matrix within which the drug is dissolved or dispersed. Controlled release systems offer a sustained release profile but are engineered to provide a predictably constant plasma concentration of the therapeutic agent that is independent of the biological environment of application. Although the various approaches to modified release dosage forms are not interchangeable, they all have in common the tendency to prolong the time that a drug is in the therapeutic range following a single administration, while decreasing the potential for peaks and troughs in plasma levels that would increase toxicity or decrease therapeutic efficacy. Other approaches to delivery of therapeutic agents can be employed to achieve desirable plasma levels of the agent or agents. For example, two therapeutic agent doses can be combined in one dosage form, with each dose formulated to achieve a different timing for delivery, or two different therapeutic agents can be combined in the dosage form. By adjusting the release profiles of the doses (either the same agent or different agents), the temporal distribution of the one or more agents can be optimized. Additives and formulations to facilitate sustained or controlled release are well-known in the art. For example, polymeric materials such as sodium carboxymethylcellulose, hydroxypropylcellulose, hydroxypropylmethylcellulose and hydroxyethylcellulose, or other cellulose ethers can be used for formulation. Dosage forms can be formulated with enteric coats to tune sustained release. Coating materials familiar in the art include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release). Tablets can be coated using known methods to form osmotically-controlled release tablets. Formulations for delivery in the small intestine and the colon include enteric coated systems, based, e.g., on methacrylate copolymers such as poly(methacrylic acid, methyl methacrylate), which are only soluble at pH 6 and above, so that the polymer only begins to dissolve upon release from the orally ingestible delivery system into the small intestine. The site where such polymer formulations disintegrate is dependent on the rate of intestinal transit and the amount of polymer present. For example, a relatively thick polymer coating can used for delivery to the colon, while a thinner layer will be adequate if a quicker dissolution of the coating is desirable. Polymers capable of providing site-specific colonic delivery can also be used, wherein the polymer relies on the bacterial flora of the large bowel to provide enzymatic degradation of the polymer coat and hence release of the drug. For example, azopolymers, glycosides and a variety of naturally available and modified polysaccharides can be used in such formulations. Multiple therapeutic agents can be delivered as the therapeutic agent deliverable using the orally ingestible delivery system described herein. In embodiments, the multiple therapeutic agents can be attached together, enclosed within a single matrix or covering layer, or otherwise integrated into a single structure that can then be enclosed within the therapeutic agent compartment of the delivery system. In other embodiments, several different dosage forms can be enclosed within a single therapeutic agent compartment, each having its own enclosure and its own delivery properties. Without limitation, a therapeutic agent deliverable can be provided in single or multiple dosage forms, optionally formulated for delayed or extended release, and then enveloped by the orally ingestible delivery systems described herein, with such agents either mixed together or isolated from each other completely or partially, for example by disposing each agent within its own compartment inside the therapeutic agent compartment, or by encasing each agent in its own membrane with particular parameters for breakdown and drug release. Single agents or multiple agents within a therapeutic agent deliverable can be formulated as pellets to be contained within capsules or within other enveloping media. In embodiments, one therapeutic agent can be coated on the surface of a second therapeutic agent either as a single form factor or as a plurality of bilayer coated capsules, and the two-layer medication structure(s) are disposed within the therapeutic agent compartment, thus comprising the therapeutic agent deliverable. The combination of two therapeutic agents in one form factor can achieve bimodal pharmacokinetic release of the two agents, as required by a patient's treatment plan. Alternatively, or in addition, an external enteric coating can be provided that dissolves more distally in the intestine, allowing delayed release. In embodiments, a combination of therapeutic agents can be combined as the therapeutic agent deliverable for delivery by the orally ingestible delivery system, where the combination of therapeutic agents is complementary or synergistic. For example, a combination of treatment agents can be provided for treating diabetes and other glucose regulation disorders, for example a peptide like an incretin (e.g., exenatide) and a small molecule like a biguanide compound (e.g., metformin). In embodiments, a small molecule therapeutic agent can be dissolved in the matrix, while an insoluble or larger-scale therapeutic agent is dispersed in packets throughout the matrix. Dosage preparations of the two agents can be titrated so that appropriate blood levels and therapeutic efficacy is attained.

As another example, a combination of living organisms and nutrient substances can be contained within a single orally ingestible delivery system as the therapeutic agent deliverable (whether intended for pharmaceutical or nutraceutical use), such as probiotic bacteria and prebiotic substances that are synergistic or complementary to each other. Prebiotic substances, as the term is used herein, include non-digestible or minimally digestible food ingredients that can selectively stimulate the growth and/or activity of one or a limited number of bacteria residing in or coming to reside in the intestinal tract, and can include, more broadly, substrates that are selectively used by microorganisms to confer a health benefit on the host. Prebiotic substances can include materials such as undigestible fibers (e.g., galacto-oligosaccharides, fructo-oligosaccharides, oligofructose, chicory fiber, inulin, and the like), which can provide a supportive milieu for the probiotic organisms being introduced. Other prebiotic substances can include natural or partially hydrolyzed collagen and other proteins that can act as supportive milieu for probiotic organisms and/or that have independent nutraceutical effects.

Both the probiotic organisms and the prebiotic substances can benefit from the transit through the stomach into the intestinal tract afforded by the orally ingestible delivery system; the properties of the orally ingestible delivery system and the packaging of the therapeutic agents it contains can be further optimized to deliver the prebiotic substances and the probiotic organisms to a preselected destination in the large or small intestine. In embodiments, a single orally ingestible delivery system can contain an optimized combination of prebiotic substances and probiotic organisms designed to facilitate biome growth and maintenance while minimizing side effects; the combination of prebiotic substances and probiotic organisms can be delivered together within the therapeutic agent compartment of the orally ingestible delivery system. The combination of prebiotics and probiotics administered together can also act as a "synbiotic," understood to be a product combining the prebiotic substance and the probiotic organisms so that they interact synergistically to improving survival and implantation of living microbes in the gastrointestinal tract by selectively stimulating their growth and/or metabolism. The probiotic strains used in synbiotic formulations can include *Lactobacilli, Bifidobacteria* spp, *S. boulardii, B. coagulans* and the like, while the major prebiotics used include oligosaccharides like fructooligosaccharide, galacto-oligosaccharide, xyloseoligosaccharide, inulin, prebiotics from natural sources like chicory and yacon roots, and the like.

The physical proximity of the prebiotic substances and the probiotic organisms can be engineered within the orally ingestible delivery system to maximize downstream interaction of the two therapeutic agents. In embodiments, probiotic organisms and prebiotic substances can be delivered separately in discrete orally ingestible delivery systems, e.g., for example, with one system adapted for delivering probiotic organisms, and a separate system adapted for delivering prebiotic substances; in this example, the two delivery systems can be administered simultaneously or sequentially, based on the patient's clinical needs. In yet other embodiments, probiotic organisms can be formulated in combination with other substances besides prebiotic ingredients to enhance the viability of the probiotic organisms or to augment their therapeutic effect, and these combinations can be delivered as a therapeutic agent deliverable within the orally ingestible delivery system. Preparations using living organisms such as probiotic bacteria can be formulated using conventional methods, for example into pellet form, with optional enteric coatings to tune their delivery to preselected areas of the intestine; in other embodiments, preparations containing lyophilized living bacteria can be pelletized and encased in enteric coating substances to facilitate their delivery to the designated target site within the intestine. As would be understood by skilled artisans, other formulations using multiple pellets containing probiotic organisms can be envisioned, for example a formulation process that mixes the probiotic-loaded pellets with cushioning agents (microcrystalline cellulose, lactose monohydrate, corn starch, porous calcium, and the like) and compresses the mixture into tablets that can then be contained within the therapeutic agent compartment of the orally ingestible delivery system.

Therapeutic agents can be specially formulated to optimize aspects of their pharmacokinetics as they are released from the orally ingestible delivery systems described herein. Using the orally ingestible delivery system, certain therapeutic agents can be delivered in an intact or an active or an activatable form into the small intestine, for example, from whence they must be taken up through the intestinal mucosa so that they can reach the systemic circulation to exert their desired effect. In an embodiment, this can be accomplished by formulating the therapeutic agent or agents in a liquid or gel matrix so that they are taken up by endocytosis (including without limitation, phagocytosis, pinocytosis and potocytosis) and are thereby transported in vesicles across the cells of the intestinal villi to enter the circulation. Following the therapeutic agent's uptake by endocytosis, it travels across the intestinal cell for discharge into the extracellular fluid within the intestinal wall, from whence it can enter the lymphatics and/or the systemic circulation.

For certain therapeutic agents' formulations, the therapeutic agent itself can first be dissolved in an aqueous medium, for example, a water-soluble protein in a hydrophilic environment such as a viscous matrix loaded with oligosaccharides to minimize water content of the solution. The aqueous medium can be pH buffered and contain other protective excipients as would be found in a formulation of the protein for parenteral administration, along with one or more oligosaccharides, e.g., inulin, trehalose, dextran, and the like. The aqueous medium can then be admixed in an oil phase to form a water-in-oil emulsion, wherein the aqueous droplets are suspended within the oily matrix. The oil phase can include edible oils and fats familiar in the art, for example, coconut oil, palm oil, olive oil, omega-3 and -6 containing fish oils, and the like, and/or their corresponding monoglycerides or long-chain fatty acids (or mixtures thereof). Using known techniques in pharmaceutical formulation and engineering such as ultrasonic vibration and homogenization, the aqueous phase and the oil phase can be combined so that the oil phase contains ultrafine nanodroplets (e.g., from tens to hundreds of nanometers in diameter) of the aqueous phase as the starting oil phase. Edible surfactants such as lecithin and phospholipids can be employed to stabilize the emulsions. Upon release of this therapeutic agent formulation from the orally ingestible delivery system, the oily material containing the aqueous nanodroplets can be ingested by the small intestine through transcytosis; in addition, while the oily phase is susceptible to the action of lipases within the small intestine, it protects the therapeutic agent in the nanodroplets from the enzymatic action of intestinal proteases in the intestine. As a consequence, the aqueous nanodroplets within the oily matrix can be taken up by the small intestine and delivered across the mucosa into the extracellular fluid for further absorption into the systemic circulation.

The oil-based vehicle can transport other types of therapeutic agents without their inclusion in aqueous nanodroplets. For example, lyophilized protein particles can be durably suspended in the oil matrix and carried along within the oil as it is taken up by the small intestine following its release from the orally ingestible delivery system. Similarly, living organisms can be suspended in an oily matrix alone, or can be contained within a viscous aqueous matrix that is then emulsified with the oily matrix to form a water-in-oil emulsion containing aqueous nanodroplets bearing the living organisms within, with the aqueous nanodroplets being suspended within the oily matrix. In certain embodiments, the aqueous nanodroplets can also contain nutrients to preserve and protect the living cells; in other embodiments, the aqueous nanodroplets can contain other organisms instead of living cells, for example virus particles, lyophilized cells, and the like.

Other combinations for treatment can be readily envisioned by skilled artisans, for conditions such as cancer treatment, or treatment of HIV, where the treatment requires a plurality of drugs having different pharmacokinetic properties and different dosages. Encasing the drug combinations having different properties (e.g., solid, semi-solid, gelled, emulsions, single phase aqueous vehicles, oil vehicles, and the like) within the orally ingestible delivery system allows them to bypass the stomach and its effects on the different therapeutic agents and be delivered to designated target areas, permitting more focused, specific, and/or predictable absorption distal to the stomach.

Therapeutic systems and methods of treatment as disclosed herein are suitable for a wide range of illnesses, diseases, and conditions. It is particularly advantageous to deliver therapeutic agents via the orally ingestible delivery system as described herein for those therapeutic agents that would otherwise require parenteral administration because of their susceptibility to breakdown in the stomach. For example, certain small molecules undergo hydrolysis when exposed to acid in the stomach. When these are used in conventional oral formulations, they require special preparation or even modification of their chemical structure to allow them to withstand the effects of stomach acid. As another example, molecules characterized by one or more peptide bonds, such as peptides, proteins, and related structures, are susceptible to enzymatic attack in the stomach via its proteases; therapeutic formulations comprising these molecules typically require parenteral administration. As yet another example, preparations containing beneficial bacteria ("probiotics") or other living organisms are vulnerable to damage in the stomach, reducing the number of viable bacteria cells or other viable cells (as applicable) that ultimately reach the colon or other intestinal target. For example, although various coating strategies and tablet preparations are under investigation to protect probiotics when they are administered orally, preparations containing viable bacterial cells are commonly delivered by enema to ensure that they reach the colon in a healthy state. The systems and methods described herein offer an alternative route of delivery and/or a better milieu for conveying viable cells to their intestinal destination for these fragile but important therapeutic agents.

As an additional benefit, the orally ingestible delivery system protects the stomach from therapeutic agents that could harm it. Certain classes of drugs, for example corticosteroids or non-steroidal anti-inflammatory agents, inflict well-recognized damage on the stomach lining, causing gastritis and ulcer formation. Bypassing the stomach can help protect this organ from these effects, while allowing the therapeutic agent to exert its beneficial effects in a non-destructive manner.

Without limitation, a wide variety of therapeutic agents are suitable for administration using an orally ingestible delivery system as described herein. Certain of these therapeutic agents are currently available in oral dosage forms, for example various antibiotics, antiviral agents, antiparasitic agents, immune suppression agents, and the like. Use of the orally ingestible delivery system disclosed herein can offer other advantages, for example it can improve pharmacokinetics and prevent gastric-related side effects. Other therapeutic agents not currently available for oral administration, in particular peptides and proteins that are susceptible to breakdown in the stomach, can be advantageously delivered orally using the orally ingestible delivery system disclosed herein. Further description of the therapeutic uses of the orally ingestible delivery system is provided below, with specific exemplification of its use with therapeutic agents that are currently available for oral ingestion, and with therapeutic agents that are currently not available for oral ingestion and are presently delivered parenterally or transrectally. The orally ingestible delivery systems disclosed herein are suitable to replace current delivery mechanisms for, without limitation, orally ingested therapeutic agents, parenterally delivered therapeutic agents, and rectally delivered therapeutic agents.

2. Orally Ingested Therapeutic Agents Suitable for Delivery Via Orally Ingestible Delivery Systems a. Active Pharmaceutical Ingredients Certain therapeutic agents (for example, active pharmaceutical ingredients or "APIs") are currently formulated for oral ingestion. In embodiments, these APIs can be small molecules rather than macromolecules such as peptides and proteins. Without specific formulation to control gastric absorption, APIs can be altered or modified in the stomach, for example by hydrolysis or by a change in their ionization state, with effects on their absorption profiles: for example, drugs that are weak acids (e.g., aspirin) will exist mainly in their non-ionic form in the stomach, permitting their absorption in the stomach, while drugs that are weak bases will be in their ionic form and will not be absorbed in the stomach. Moreover, certain of these APIs can damage the stomach itself. For both of these reasons (to control absorption in the stomach and to avoid contact between the drug and the stomach leading to damage), it is desirable to allow certain APIs to pass through the stomach without encountering its environment or its tissues.

Currently, a number of APIs have been formulated to withstand exposure to gastric acid, with variable results. As an example, certain antibiotics, such as the macrolide antibiotics (e.g., erythromycin) are unstable under the low pH conditions in the stomach. Bypassing the stomach can improve bioavailability if these drugs can be delivered to the small intestine for uptake without having been damaged by the gastric pH. As another example, certain drugs can be delivered orally, but they are known to have deleterious effects. For those drugs, (for example NSAIDs, COX inhibitors, corticosteroids, bisphosphonates, clopidogrel, potassium supplements, and a variety of cytotoxic agents used in cancer chemotherapy), both local and systemic factors have been identified that produce their adverse effects on the gastric mucosa. Bypassing the gastric mucosa can reduce the local deleterious effects, potentially reducing the morbidity associated with their use.

b. Wellness Products

In other examples, certain therapeutic agents are intended to achieve non-medical benefits, such as enhancing wellness, improving sense of well-being, or providing recreational or hedonic benefits. An example of a class of therapeutic agents providing both medical and non-medical benefits is the cannabinoid family. Oral administration of cannabinoids via whole-plant or cannabis-infused foods (so-called "edibles") is well-known. Bioavailability of the bioactive cannabinoids via oral ingestion is variable, however. While oral preparations are desirable for various social, economic, and hedonic reasons, consistent and reproducible bioavailability is desirable too. A delivery system such as the orally ingestible delivery system provided herein can result in more predictable absorption, bioavailability, and physiological effects.

Probiotic treatments represent a hybrid treatment modality, with both oral and rectal administration currently being employed. The systems and methods disclosed herein offer an alternative to both routes of delivery. Documented beneficial effects of probiotics include the prevention or treatment of diarrhea, constipation, changes in bile salt conjugation, enhancement of anti-bacterial activity, and anti-inflammatory effects. Various diarrhea conditions (for example, acute infantile diarrhea, antibiotic-associated diarrhea, and travelers' diarrhea) have been successfully treated with probiotics, implicating mechanisms such as stimulation of the immune system, competition for binding sites on the intestinal epithelial cells, and secretion of bactericidins. Irritable bowel syndrome (IBS), a chronic condition characterized by recurrent bouts of abdominal discomfort, bloating, and abnormal bowel habits, has been treated effectively with probiotic organisms in several studies. Administration of probiotic organisms also holds promise for treating inflammatory bowel disorder (IBD), a chronic, relapsing, multifactorial disorder causing inflammation of the intestinal tract and producing severe diarrhea and abdominal pain; IBD occurs throughout the intestinal tract and includes the diagnoses of ulcerative colitis (affecting the colon and rectum) and Crohn's disease (affecting any part of the gastrointestinal tract). Mechanisms for the efficacy of probiotic administration in these conditions include their competitive interaction with pathogenic flora and their effect on the immune system. IBS and IBD have also been treated with certain prebiotic substances (for example, hydrolyzed guar gum), raising the possibility that a synbiotic approach can yield even better therapeutic responses. Probiotics have also been used for treating non-gastrointestinal conditions, such as allergies, cancer, AIDS, respiratory and urinary tract infections, cardiovascular diseases and hypercholesterolemia, metabolic diseases. Rectal delivery of probiotic organisms is typically reserved for the treatment of serious diseases, as described in more detail below, while oral administration is used for treatment of milder diseases and for achieving health benefits.

Use of the orally ingestible delivery system as described herein can protect the living organisms as they pass through the stomach and proximal intestine en route to their target destination. Therefore, the oral route for administration can be used for serious diseases, where delivery of the living organisms in sufficient quantities and to designated anatomic loci can be crucial. The oral route can also be used for wellness purposes, with greater precision in the dose of living organisms delivered and with more assurance of their viability. One example, described herein in more detail, is the delivery of probiotic bacteria using these systems and methods. While probiotic bacteria can be delivered by commercial food products, foods such as cheese, yogurt, milk, and the like do not deliver a large number of viable bacteria to their targets, because the bacteria they contain are unable to survive the physiological conditions in the stomach and intestines. Conventional pharmaceutical products use delivery systems such as beads, capsules, and tablets in an attempt to deliver viable functional bacteria to their targets in sufficient numbers to achieve the desired health benefits. Typically, however, doses of $10^8$-$10^9$ healthy bacteria must reach the intestine to exert the desired health-related effect, but studies have shown that up to 60% of viable bacteria administered orally via conventional formulations can be killed in the stomach. An orally ingestible delivery system as disclosed herein offers an oral delivery route for probiotic bacteria that protects them from conditions in the stomach, allowing them to arrive at their target area in the large or small intestine in a viable state and in sufficient numbers to provide their intended beneficial effects.

In embodiments, the probiotic bacteria can be advantageously combined with prebiotic substances or other agents that can enhance the viability or efficacy of the living organisms. As described previously, the probiotic organisms can be combined with prebiotic substances to enhance their viability and/or therapeutic efficacy, to be delivered together in a single orally ingestible delivery system, or to be delivered separately in separate delivery systems. The synergy of a combination of probiotic organisms and prebiotic substances (for example, in a synbiotic formulation) can offer therapeutic advantages. In embodiments, the probiotic organisms can be combined with other agents that enhance their viability and/or therapeutic efficacy, said combination being administered within a single orally ingestible delivery system to optimize the administration of the organisms in sufficient quantities and to the designated area. Ancillary agents can be included in the probiotic payload along with the viability/efficacy enhancers, for example mucins and other adhesive agents that can facilitate the attachment of the probiotic organisms to the intestinal mucosa and/or facilitate the repair the surface of the mucosa, which may be of particular benefit in derangements of the intestinal mucosa such as exist in various diarrheal conditions.

Whether for treatment of disease or enhancement of wellness, the therapeutic potential of probiotic organism treatment depends on the survival of these organisms as they reach their target destination. The therapeutic efficacy of probiotic bacteria stems from several factors. First, these bacteria must transit the stomach and the intestine, so that they can attach to the mucosal cells in the targeted area of the gastrointestinal tract. This attachment can inhibit the binding of enteric pathogens by a process of competitive exclusion. This attachment also can initiate signaling events that stimulate the production of cytokines. At the same time, probiotic bacteria can produce lactic acid and other bactericidal substances, which affect the growth of commensal micro-organisms within the gut.

Furthermore, probiotic bacteria can produce substances like butyric acid that affect the turnover of intestinal mucosal cells, inhibit the growth of pathogens, neutralize potential carcinogens, and generally improve the health of the enteric ecosystem. While certain mechanisms (for example, formulation adjustments, selection of acid-resistant strains, and microencapsulation) can increase the number of viable organisms, it is well recognized that only a small portion of administered probiotic organisms survive to reach their destinations within the gastrointestinal tract. The systems and methods disclosed herein can be advantageously adapted for the oral administration of probiotic bacteria and prebiotic-probiotic formulations, with the expectation of good bacterial survival due to bypassing the regions of the gastrointestinal tract where these organisms are subject to attack.

3. Parenterally Delivered Therapeutic Agents Suitable for Delivery Via Orally Ingestible Delivery System Parenteral administration, i.e., by routes besides the gastrointestinal tract, is presently required in situations where the therapeutic agent cannot achieve sufficient bioavailability when it is administered through the gastrointestinal tract. Drugs not suitable for oral administration, for example therapeutic agents susceptible to degradation in the stomach such as proteins and peptides, are typically delivered parenterally.

In an embodiment, therapeutic agents suitable for use with the orally ingestible delivery system described herein include peptides and proteins. As used herein, the term "protein" refers to a sequence of amino acids connected together by peptide bonds and having a chain length long enough to produce a discrete tertiary structure, typically with a molecular weight between 1-3000 kD. In contrast to the term "protein," the term "peptide" refers to a sequence of amino acids that are connected together by peptide bonds but that does not have a discrete tertiary structure. Typically, peptides contain 50 or fewer amino acids, although larger peptides or polypeptides exist with more amino acids in their chains but lacking the tertiary structure of a protein.

a) Proteins

A wide variety of biopolymers are included within the scope of the term "protein," including but not limited to protein structures such as antibodies, fusion proteins, enzymes, PEGylated proteins, synthetic polypeptides, protein fragments, lipoproteins, enzymes, structural peptides, anti-infectives, antiproliferatives, cytokines, vaccines, and the like. Illustrative but non-limiting categories of proteins for which the oral ingestible delivery system can be used advantageously are described below in more detail.

As used herein, the term "antibody" refers to an immunoglobulin produced by the plasma cells and used by the immune system to neutralize foreign substances such as bacteria, viruses, or tumor cells. Antibodies are classified as monoclonal or polyclonal. Monoclonal antibodies are produced by identical immune cells that are clones of a parent cell, having affinity for a single epitope; polyclonal antibodies are produced by multiple different immune cell lineages and bind multiple epitopes. A bispecific monoclonal antibody can be engineered to allow affinity with two targets.

In embodiments, antibodies can be combined with other substances, for example active pharmaceutical ingredients, to permit the targeted delivery of the API to a preselected area. Such combinations, termed antibody-drug conjugates (ADCs) are typically monoclonal antibodies attached to biologically active drugs by chemical linkers having breakable bonds. For cancer treatment, the ADC's monoclonal antibody can be specific for surface antigens on particular tumor cells, so that the ADC can bring a powerful anti-tumor agent into closer contact with the tumor cells themselves. Coupling antibodies with cytotoxic agents can permit greater control of drug pharmacokinetics while greatly increasing the delivery of the anti-cancer drug to the malignant tissue, while minimizing impact on healthy tissue. ADCs exert their activity by (1) selectively binding to the tumor cells via the antibody moiety, (2) promoting internalization into intracellular compartment via receptor-mediated endocytosis, and (3) releasing the cytotoxic payload into the cell following lysosomal degradation, thus causing cell death. Representative ADCs include Ado-trastuzumab emtansine (KADCYLA®, Genentech/Roche), and Fam-trastuzumab deruxtecan-nxki (ENHERTU®, Daiichi Sankyo and AstraZeneca), each used in the treatment for metastatic breast cancer; Brentuximab vedotin (ADCETRIS®, Seattle Genetics), and Polatuzumab vedotin-piiq (POLIVY™, Genentech/Roche), each used in the treatment of various lymphomas; Enfortumab vedotin (PADCEV™, Astellas Pharma/Seattle Genetics), used in the treatment of metastatic urothelial cancers; and Gemtuzumab Ozogamicin (MYLOTAG®, Pfizer) and Inotuzumah ozogamicin (BESPONSA®, Pfizer), each used in the treatment of various leukemias.

In certain embodiments, antibodies can be PEGylated or otherwise derivatized, which can prolong their half-lives and/or enhance their bioavailability. PEGylated antibodies and other PEGylated proteins have poly(ethylene glycol) or other stealth polymer groups covalently attached thereto, which can reduce their removal by renal filtration or decrease their uptake by the reticuloendothelial system or diminish their enzymatic degradation. Antibodies are well-recognized treatment agents for a wide variety of human disorders or conditions, wherein their affinity for a particular target can be exploited to lead to amelioration of the disorder or condition. Monoclonal antibodies, for example, can be engineered to bind specifically to certain cells or proteins, which then stimulates the patient's immune system to attack the targets so tagged. Antibodies, as proteins, are susceptible to denaturation and enzymatic digestion in the stomach, resulting in inactivation, loss of therapeutic efficacy, instability, or other deleterious effects, so that they require parenteral administration. Non-limiting examples of antibodies suitable for delivery with the orally ingestible delivery system disclosed herein can include the following:

Adalimumab (HUMIRA®, marketed by AbbVie) is a tumor necrosis factor (TNF) blocker used to treat a variety of inflammatory and autoimmune conditions, including ulcerative colitis, rheumatoid arthritis, psoriatic arthritis, Crohn's disease, plaque psoriasis, and the like. Bevacizumab (AVASTIN®, marketed by Genentech) is an angiogenesis inhibitor (anti VEGF-A) used to treat a number of cancers such as colon cancer, lung cancer, breast cancer, brain cancer, ovarian cancer and renal cancer by intravenous infusion; for cancer treatment, it can be combined with standard small-molecule chemotherapeutic agents such as 5-fluorouracil, paclitaxel, and carboplatin. Cetuximab (ER- BITUX®, marketed by Eli Lilly) is an epidermal growth factor receptor (EGFR) inhibitor used to treat head and neck cancer, metastatic colon cancer, and metastatic lung cancer. Denosumab (PROLIA®, marketed by Amgen) inhibits the maturation of pre-osteoclasts into osteoclasts by affecting their RANK surface receptors; it is used to treat osteoporosis, giant cell tumors of the bone, and cancers that have metastasized to bones. Infliximab (REMICADE®, marketed by Janssen Biotech) is a TNF blocker that is used to treat various autoimmune diseases such as Crohn's disease, ulcerative colitis, rheumatoid arthritis, ankylosing spondylitis, psoriatic arthritis, psoriasis, and Behcet's disease. Natalizumab (TYSABRI®, marketed by Biogen Idec) is an antibody against the cell adhesion molecule alpha-4 integrin, used to treat multiple sclerosis and Crohn's disease. Rituximab (RITUXAN®, marketed by Biogen and Genentech) binds to the protein CD20, which is found on the surface of immune system B cells, triggering cell death as it binds to this protein; this monoclonal antibody is used to treat blood cancers having malignant B cells, and autoimmune diseases such as rheumatoid arthritis, thrombocytopenic purpuras, hemolytic anemias, bullous skin diseases, and other disorders mediated by having too many B cells, overactive B cells or dysfunctional B cells. Ustekinumab (STELARA®, marketed by Janssen Biotech) is a monoclonal antibody that acts as an interleukin 12 and interleukin 23 antagonist, proteins that regulate the immune system and are implicated in certain autoimmune inflammatory disorders; it is used to treat psoriasis, psoriatic arthritis, and Crohn's disease.

As used herein, the term "fusion protein" or "chimeric protein" refers to a protein that is created from two different proteins encoded by two different genes, with the resulting protein retaining certain or all of the functional properties of the component proteins. Some fusion proteins can contain the whole functional domain of the original proteins. In other cases, fusion proteins are engineered to retain beneficial segments of component proteins while replacing other segments with domains from another component protein. For example, a therapeutic antibody produced using mouse genes may contain segments that elicit immune reactions when given to humans; using the chimerization processes of genetic engineering, a fusion protein can be produced in which the immunogenic portions of the protein are replaced with corresponding domains from human antibodies, so that its specificity for its therapeutic target is retained without the immunological side effects. Fusion proteins, as proteins, are susceptible to degradation (for example, inactivation, loss of therapeutic efficacy, instability, or other deleterious effects), in particular denaturation and enzymatic digestion in the stomach, so that they require parenteral administration. Non-limiting examples of fusion proteins suitable for delivery with the orally ingestible delivery system disclosed herein can include the following:

Abatacept (ORENCIA®, marketed by Bristol-Myers Squibb) is a fusion protein that binds to T-cells and prevents their activation, used to treat rheumatoid arthritis, psoriatic arthritis, and juvenile idiopathic arthritis. Etanercept (ENBREL®, marketed by Amgen) is a TNF inhibitor used to treat autoimmune disorders such as rheumatoid arthritis, juvenile idiopathic arthritis, psoriatic arthritis, and ankylosing spondylitis. Rilonacept (ARCALYST®, marketed by Regeneron) is an interleukin-1 inhibitor given "orphan drug" status by the FDA, used for the treatment of cryopyrin-associated periodic syndromes. Romiplostim (NPLATE®, marketed by Amgen) is a fusion protein analogue of thrombopoietin, a hormone that stimulates the production and differentiation of megakaryocytes, the precursor cells of platelets; it is used to treat chronic idiopathic thrombocytopenic purpura.

As used herein, the term "enzyme" refers to a macromolecule that is a catalyst for biochemical reactions. The specificity of an enzyme for a particular reaction is mainly derived from its three-dimensional structure. Enzymes are typically proteins, although certain catalytic RNA molecules can also act as enzymes (these RNA molecules being known as ribozymes). Enzymes can be used as therapies in disorders characterized by enzyme deficiency. For such treatments, termed enzyme replacement therapy (ERT), enzymes are replaced exogenously by administering solutions intravenously that contain the enzyme. Currently, ERT is used to treat a number of genetic diseases in which a crucial enzyme is not formed. Non-limiting examples of enzyme deficiencies suitable for treatment with the orally ingestible delivery system disclosed herein can include the following:

For example, certain lysosomal storage diseases (for example, Gaucher disease, Fabry disease, the mucopolysaccharidoses MPS I, II, and VI, and Pompe disease) are treated by replacing the enzyme that is lacking; lysosomal storage diseases are a group of childhood-onset, genetically-mediated diseases, fatal without treatment, in which certain enzymes used in the lysosomes are absent, leading to a buildup of a substrate or metabolite within the cells. As another example, patients with severe combined immunodeficiency (SCID) syndrome resulting from an adenosine deaminase deficiency can be treated with ERT to replace that enzyme; SCID syndrome is a childhood-onset genetically-mediated disease, fatal without treatment, in certain cases of which the enzyme adenosine deaminase is lacking, leading to a buildup of metabolites in the lymphocytes that impair their development and immunological function. ERT does not offer a cure for these diseases, and they require lifelong intravenous infusions of the deficient enzyme in order to provide palliation. Enzymes, as proteins, are susceptible to denaturation and enzymatic digestion in the stomach, so that they require parenteral administration.

As used herein, the term "cytokine" refers to a family of small proteins, peptides, and glycoproteins that act in nano-picomolar concentrations as humoral regulators to modulate the functional activities of individual cells and tissues, to mediate interactions between cells, and to regulate cellular interaction with the extracellular environment. Certain cytokines resemble hormones in their biological activities and systemic effects, for example mediating biological phenomena such as inflammation, sepsis, and wound healing. Other cytokines have structures or activities similar to enzymes, acting to stimulate or inhibit activities of other biomolecules, although at much lower concentrations than circulating hormones. Although cytokines tend to have divergent primary sequences, some can have similar three-dimensional features that allow them to be grouped into families. Cytokine subfamilies include, inter alia, interleukins, lymphokines, monokines, interferons, colony stimulating factors, and chemokines. Cytokines that are secreted by cells can be processed through intracellular organelles that perform glycosylation, so that these cytokines are released as glycoproteins. Cytokines, as proteins, glycoproteins, or peptides, are susceptible to degradation (for example, inactivation, loss of therapeutic efficacy, instability, or other deleterious effects), in particular, denaturation and enzymatic digestion in the stomach, so that they require parenteral administration. Non-limiting examples of cytokines suitable for delivery with the orally ingestible delivery system disclosed herein can include the following: Epoetin alfa (EPO- GEN®, marketed by Amgen or PROCRIT®, marketed by Janssen Biotech) is a recombinant form of erythropoietin, a glycoprotein cytokine that stimulates red blood cell production, used to treat chronic anemia, for example in chronic renal disease and during cancer chemotherapy. Filgrastim (NEUPOGEN®, marketed by Amgen) is a recombinant form of granulocyte-colony stimulating factor, a glycoprotein cytokine that stimulates the bone marrow to produce neutrophils and stem cells, used to treat neutropenia produced, for example, by cancer chemotherapy, by radiation poisoning, or in HIV/AIDS. Granulocyte-macrophage colony-stimulating factor (GM-CSF) is a monomeric glycoprotein that stimulates white blood cell growth; it has been sold in recombinant versions for use in neutropenic conditions such as following cancer chemotherapy, and for stimulating white blood cell growth after bone marrow transplantation. Interferons, another type of cytokines, are a large family of signaling proteins that act as antiviral agents and that modulate the immune system. They can also suppress angiogenesis and the proliferation of endothelial cells, and they activate immune cells such as macrophages and natural killer cells. Various interferons are currently being used clinically: pegylated interferon alfa-2b (PEGINTRON®, marketed by Merck, and often combined with other antiviral agents such as protease inhibitors and retroviral agents) for treatment of hepatitis, including hepatitis B and chronic hepatitis C, and for treatment of melanoma (SYLATRON®, marketed by Merck); interferon beta-1a (AVONEX®, marketed by Biogen, REBIF®, marketed by EMD Serono) for treatment of relapsing multiple sclerosis; interferon-gamma (ACTIMMUNE®, marketed by Horizon Pharma) used for treatment of chronic granulomatous disease and malignant osteopetrosis, with potential applications for malignancies. Of note, the various cytokines all require parenteral administration. They often have significant side effects that can be related to the pharmacokinetics of administration. As an example, for interferon-gamma, systemic side effects such as fever, fatigue, nausea, vomiting, diarrhea, neurotoxicity, and leukopenia have been attributed to dosage requirements associated with parenteral administration.

b) Vaccines, Living Organisms, Nucleic Acids

As used herein, the term "vaccine" refers to a biological preparation that incites active acquired immunity to a particular disease. Vaccines can contain various agents related to the organism that they protect against: live attenuated vaccines contain live viruses but weakened so that their administration does not cause illness (for example, measles-mumps-rubella, chicken pox, influenza); inactivated or killed vaccines contain the virus but in a non-living or non-pathogenic state (for example, hepatitis A, polio); toxoids contain inactivated toxins, where the toxins produced by the pathogenic organisms are responsible for the disease produced by disease-causing organisms (for example, diphtheria, tetanus); subunit/conjugate vaccines include subunits of the pathogen (hepatitis B, pertussis, meningococcal or pneumococcal vaccines). Vaccines typically contain proteins or peptides, and they are thus susceptible to degradation (for example, inactivation, loss of therapeutic efficacy, instability, or other deleterious effects), in particular, denaturation and enzymatic digestion in the stomach. Most vaccines require parenteral administration. While some vaccines are suitable or even preferable for oral administration, for example vaccines against enteric pathogens, the oral forms of vaccines often do not produce enough of an immune response to be consistently effective. Using the orally ingestible delivery system as disclosed herein can offer advantages for vaccination programs by allowing more convenient and economical access to disease prophylaxis.

Other living organisms can also be delivered using the orally ingestible delivery system disclosed herein. The therapeutic agent compartment and the differentially permeable (for example, digestible) capsule system can be engineered to promote viability of living organisms while protecting them as the pass through the stomach and proceed along the gastrointestinal tract to their preselected target site within the intestine. For example, as previously described, probiotic organisms can be disposed within the therapeutic agent compartment (either with or without prebiotic substances) and formulated so as to optimize their viability when they reach their intended intestinal target. Because probiotic organism formulations presently administered encounter the harsh conditions of the stomach, with resulting low viability of the organism population, the orally ingestible delivery system disclosed herein can open up new therapeutic dimensions for this treatment modality: protected from exposure to stomach acid, the probiotic organisms can reach their target within the small intestine and exert their beneficial effects. Similarly, viable stem cells and other viable cells can be disposed within the therapeutic agent compartment, formulated appropriately (for example, to provide them with media and other factors to promote their viability, or to allow their delayed release at a preselected time or site), and allowed to disperse upon reaching the preselected site in the large or small intestine.

The field of gene therapy involves the delivery of genetic material (DNA or RNA) to target cells. This genetic material then enters the target cells and, in the case of DNA, the target cell nucleus, where it directs the manufacture of desirable protein products. Therapeutic DNA, for example, can be used as a temporary template for protein synthesis, or it can be incorporated permanently into the host's DNA to produce ongoing therapeutic effects. The delivery of genetic material can take place using viral or non-viral vectors. While systemic intravenous delivery is commonly employed for gene therapy, local delivery methods are also applicable, including surgical, percutaneous, and catheter-based delivery systems. Oral delivery of gene therapy technologies has been hindered by the challenges posed by the gastrointestinal system: the acidic pH of the stomach, the enzymes in the stomach and small intestine, and the mucus barrier preventing access to the mucosal cells. To achieve therapeutic efficacy, the genetic material must be transported to the cells of the target tissues.

Use of the orally ingestible delivery system as disclosed herein can provide protection for gene therapy modalities as they traverse the stomach and small intestine. Upon reaching their designated location in the small intestine, the genetic material can exit the delivery vehicle and achieve local, targeted cellular access. The genetic material can be formulated to facilitate its cell-specific targeting, and to improve its ability to access and enter the target cells. For example, the genetic material can be encapsulated to improve its stability, its release properties, or its uptake, and the genetic material can be further formulated (for example, in a dual material or multi-compartmental particulate system) to allow for its efficient uptake and cell penetration.

As used herein, the terms "viable cell" and "living organism" encompass any living cell whether naturally produced or genetically modified. In embodiments, genetically modified viable cells can be engineered to serve as treatments for genetically-based disorders. As an example, Hemophilia B, an X-linked clotting disorder caused by the lack of clotting factor IX (FIX) due to mutations in the FIX gene, lends itself to treatment with gene or cell therapy via the infusion of living organisms. To date, gene therapies using adeno-associated viral vectors have been employed experimentally, but with significant side-effects.

Use of genetically modified cells has been offered as an alternative. In one set of animal studies, induced pluripotential stem cells were collected from hemophiliac animals, and then genetically modified to correct the relevant gene defect. These cells were then transplanted into the animals, with good results. Such cells, with their genetic modification, fall within the scope of the term "viable cells." Other examples of engineered organisms (for example, live bacteria that have been modified to express certain proteins, stem cells that include genetic correction or that can be induced to express certain proteins or other factors, and the like) can be readily envisioned by artisans having ordinary skill in the art; such engineered organisms are included, without limitation, within the definition of "viable cells" or "living organisms," as used herein.

c) Peptides

Peptides have a variety of uses as therapeutic agents. For example, they can act as hormones, signaling molecules, receptor agonists, or structural components of larger macromolecular assemblies. Peptide families in nature include antimicrobial peptides, tachykinin peptides, vasoactive intestinal peptides, pancreatic polypeptides, opioid peptides, calcitonin peptides, cytokines, and the like. Peptide therapies (both peptide agonists and antagonists) are directed at metabolic disorders such as non-insulin-dependent diabetes, cardiovascular disorders such as high blood pressure, oncological disorders, hormone-related disorders such as osteoporosis and abnormal growth, and the like. Non-limiting examples of peptides suitable for delivery with the orally ingestible delivery system disclosed herein can include the following:

Exenatide (BYETTA®) is a synthetic form of a 39-amino-acid peptide secreted by the salivary glands of the desert Gila monster; it is a potent agonist of mammalian GLP-1R, allowing it to be used in the treatment of Type 2 diabetes; however, it presently requires periodic subcutaneous injection.

Teriparatide (FORTEO®, marketed by Eli Lilly) is a recombinant human protein that includes 34 of the N-terminal amino acids of endogenous parathyroid hormone; it is used to treat severe osteoporosis by stimulating bone regrowth. However, as a peptide, teriparatide must be injected subcutaneously. Parathyroid hormone itself is a hormone that regulates serum calcium through its effects on bone, kidney, and intestine. It is an 84 amino acid peptide prohormone that interacts with its target cells to activate them. When certain conditions and surgical interventions can result in low parathyroid hormone levels, there is currently no specific replacement for the hormone itself. Instead, the effects of low parathyroid hormone on calcium metabolism are currently treated by combinations of calcium and vitamin D supplementations and teriparatide.

Somatostatin (growth hormone-inhibiting hormone) is a peptide hormone that has a 14 amino acid active form and a 28 amino acid active form. This hormone regulates the endocrine system and affects neurotransmission and cell proliferation, via interaction with certain G-protein-coupled receptors and inhibition of secondary hormone release. Somatostatin inhibits insulin and glucagon secretion. Synthetic peptides can produce somatostatin-like effects and are in clinical use. Octreotide (SANDOSTATIN Novartis) and lanreotide (SOMATULINE Ipsen Pharmaceuticals) inhibit growth hormone, glucagon, and insulin; they are used to treat carcinoid syndrome, acromegaly, and polycystic diseases of the liver and kidney. Both are currently administered parenterally.

Somatotropin (human growth hormone) is a peptide hormone formed as a single chain of 191 amino acids. It controls cell reproduction, cell regeneration, and human growth and development. In its recombinant form, it is used to treat conditions such as short stature or growth failure in children (for example, Turner syndrome, idiopathic short stature, SHOX deficiency, failure to catch up in height after small for gestational age birth), and adult-onset growth hormone deficiency in adults. It is administered parenterally. Gonadotropin-releasing hormone (GnRH) is a linear decapeptide hormone released by the hypothalamus and targeting the anterior pituitary, where it stimulates the release of the gonadotrophic hormones follicle-stimulating hormone and luteinizing hormone. Analogues of GnRH are used clinically, either to stimulate release of gonadotrophins or to suppress their release. One analogue, leuprorelin, is used to treat breast cancer, prostate cancer, and precocious puberty. Other conditions responsive to GnRH analogues include estrogen-dependent conditions such as endometriosis or uterine fibroids and control of ovarian stimulation during in vitro fertilization. GnRH analogues are delivered by continuous intravenous infusion. Incretins are a family of hormones that stimulate insulin release and/or inhibit glucagon release, thereby lowering blood glucose. Medications based on incretins or synthetic analogues of incretins are used in treating Type 2 diabetes. Incretins include the intestinal peptide GLP-1 (glucagon-like peptide) and GIP (gastric inhibitory peptide, also termed glucose-dependent insulinotropic peptide). The GLP-1 peptide acts to stimulate the GLP-1 receptors on the beta cells of the pancreas, thereby increasing the release of insulin, which in turn lowers blood glucose. Included among the incretin analogues are peptides such as exenatide (discussed above), liraglutide (an acylated 30-31 amino acid peptide, marketed as Victoza® by Novo Nordisk), lixisenatixe (a 44 amino acid peptide, derived from Gila monster venom), albiglutide (a 645 amino acid peptide, marketed as TANZEUM® by GSK), dulaglutide (a peptide having 90% amino acid homology with endogenous GLP-1 and covalently linked to a human IgG4-Fc heavy chain by a small peptide linker, marketed as TRULICITY® by Eli Lilly). All of these agents are typically administered parenterally. In September 2019, RYBELSUS®, an oral form of the GLP-1 receptor agonist semaglutide, was approved by the FDA for treatment of Type 2 diabetes; this peptide had previously only been available in an injectable form.

Insulin is a peptide hormone that controls the entry of glucose into cells, removing circulating glucose from the bloodstream and providing cells with a source of energy. Insulin is produced by the islet cells of the pancreas. Lack of effective insulin is the key feature of both Type 1 and Type 2 diabetes: in both cases, the glucose stays in the bloodstream, causing deleterious effects, while the cells are deprived of adequate glucose for energy production. Type 1 diabetes occurs when the patient's own immune system attacks the islet cells so that they cease to produce insulin; for these patients to survive, insulin must be supplied externally. Type 2 diabetes has a more insidious onset, occurring when insulin is inadequate to transport glucose into the cells. In Type 2 diabetes, the tissues develop a resistance to the normal effects of insulin, and the islet cells cannot produce enough insulin to overcome the tissue resistance. Treatments exist to overcome insulin resistance in Type 2 diabetes, since insulin is still being produced. However, in Type 2 diabetes, endogenous insulin can be insufficient, and exogenous insulin administration is required. Insulin is formed from two peptide chains linked together by disulfide bonds, one with 21 amino acids and the other with 30 amino acids. To date, the only delivery forms for insulin are parenteral, because the peptide cannot survive the harsh conditions of the stomach and duodenum; insulin shots, insulin pens, insulin pumps, and insulin inhalers are available to deliver this hormone to patients on various regular dosage schedules, and insulin can be infused intravenously for emergency intervention. Oral dosage forms, though, are desirable so that a diabetic patient can avoid frequent needle sticks or other invasive measures. Several companies have taken on the challenge of oral insulin delivery, for example with formulations as developed by Novo Nordisc and by Oramed Pharmaceuticals Inc., and with devices such as those produced by Rani Therapeutics and by scientists at MIT.

Amylin is a small (37 amino acid) hormone released into the bloodstream by the beta cells of the pancreas, along with insulin release after a meal. This hormone is completely absent in patients with Type 1 diabetes. An analog of amylin, pramlintide (SYMLIN®, marketed by Astra Zeneca), is synergistic with exogenously administered insulin in regulating blood glucose in diabetic patients, slowing gastric emptying, stimulating hypothalamic receptors to promote satiety, and inhibiting the release of the catabolic hormone glucagon. Pramlintide is administered parenterally.

Vasopressin and vasopressin analogues such as desmopressin and terlipressin are peptides that regulate urinary output, plasma osmolality, blood pressure, and various clotting factors. Parenteral and oral dosage forms are available for treating conditions including polyuria and polydipsia, diabetes insipidus, hemophilia and von Willebrand disease, sickle cell disease, and primary nocturnal enuresis. The oral dosage forms deliver a much lower effective dose than the parenteral forms, so that they tend to be used for conditions requiring lower doses of the peptide. For higher doses, especially in non-pediatric patients, parenteral dosage is employed.

d) Endogenous Chemical Messengers

Small molecules such as amino acids and monoamines and peptides can act as endogenous chemical messengers, for example neurotransmitters. Such chemical messengers include amino acids (for example, glutamate, aspartate, D-serine, gamma-aminobutyric acid, glycine), monoamines (for example, dopamine, norepinephrine, epinephrine, histamine, serotonin), trace amines (for example, phenethylamine, N-methylphenethylamine, tyramine, tryptamine), purines (for example, adenosine, adenosine triphosphate), and a wide range of neuropeptides. When functioning as a neurotransmitter, the molecule can carry messages between neurons via influence on the postsynaptic membrane, without affecting membrane voltage. A neurotransmitter acts directly on the neuron either to excite it or inhibit it. Certain diseases and disorders result from overactivity, deficiency, or imbalance of particular neurotransmitters: for example, Parkinson's disease is due to inadequate dopamine production mainly in the substantia nigra; other neurological and neuropsychiatric disorders have been attributed to imbalances of neurotransmitters such as serotonin and glutamate; addictive behavior is linked to the effect of the addictive substances on dopamine in the brain. Treatment of neurotransmitter-related disorders can involve the administration of neurotransmitter precursors, which can act to increase the effective amount of the designated neurotransmitter in the brain. Other treatments of neurotransmitter-related disorders can involve the administration of active pharmaceutical ingredients that regulate the release or breakdown of neurotransmitters. These agents and neurotransmitters themselves are suitable for delivery with the orally ingestible delivery system disclosed herein. Signaling molecules traveling via the circulatory system rather than within the nervous system are termed hormones.

Hormones are a class of signaling molecules produced by specific organs (glands) in the body, to be transported by the circulatory system to distant target organs, thereby regulating their behavior. Certain hormones are proteins or peptides; examples have been provided above that use the orally ingestible delivery system as disclosed herein to deliver proteins or peptides, including protein or peptide hormones. Hormones can include other chemical structures, however. There are three other classes of hormones besides those that are configured as proteins or peptides: amines or small molecule amino acid derivatives; eicosanoids; and steroids. Many hormones and their structural and functional analogs are useful as medications, for example, estrogens, progestogens, thyroxine, anabolic steroids, and corticosteroids. Certain of these are formulated for oral administration, while others are administered parenterally. These non-protein/peptide hormones can be advantageously delivered using the orally ingestible delivery system as disclosed herein to afford more therapeutic options.

4. Rectally Delivered Therapeutic Agents Suitable for Delivery Via Orally Ingestible Delivery System Rectal routes of administration are suitable for certain therapeutic agents for therapeutic agents intended for systemic uptake via the colonic vasculature, or for therapeutic agents intended to exert their effects on the colon. For this first category, a number of drugs are available by suppository for situations where rapid adsorption is desired: rectal administration can achieve better plasma levels and therapeutic effectiveness when compared to orally or intramuscularly administered drugs at a similar dose. Rectal administration can also be used to deliver drugs when modes of parenteral administration are not available or are undesirable, for example for delivering medication at home instead of in a medical setting, or for treating pediatric patients or other patient populations for whom injections would be painful or poorly tolerated. Certain categories of therapeutic agents are delivered rectally and intended to act within the colon itself. An example of this category is seen in the treatment of ulcerative colitis, where the therapeutic agent is delivered to the site of the pathology and exerts its effects directly on the affected tissues, for example mesalazine suppositories for the treatment of distal colonic ulcerative colitis.

Inflammatory bowel disease ("IBD"), including ulcerative colitis and Crohn's disease, is a chronic inflammatory disorder of the GI tract, with symptoms including abdominal pain, diarrhea, rectal bleeding, and damage to the intestinal mucosa. In recent years, biological agents such as anti-TNF-$\alpha$, anti-$\alpha 4\beta 7$, and anti-interleukin monoclonal antibodies have become available to treat IBD, with good results. However, these treatments are not uniformly successful. Therefore, other treatment modalities are being investigated, including those that involve stem cell delivery. The healthy intestinal mucosa is formed as a monolayer of intestinal epithelial cells that are maintained by intestinal stem cells residing at the bottom of the mucosal crypts. Since mucosal ulceration is the hallmark lesion of IBD, renewing or regenerating the mucosa through stem cell administration offers a potentially useful approach to treatment of IBD.

Trials of stem cell transplantation in patients refractory to other treatments have, to date, involved parenteral administration of hematopoietic stem cells or mesenchymal stem cells using conventional systemic stem cell transplantation protocols. Those protocols are strenuous for patients, with frequent serious adverse events. Local or topical transplantation of intestinal stem cells or other stem cells is an option that avoids the systemic effects of conventional stem cell transplantation, while offering the possibility of an effective treatment for IBD. Delivery of the stem cells to the target tissue needs to be accomplished in a way that preserves their viability, however. Rectal delivery of appropriate stem cells (or their delivery via a stoma for patients lacking a rectum or for patients with other diversions of their intestinal anatomy) may accomplish this, although that delivery route may only be available for ulcerative colitis patients, and not for patients with Crohn's disease afflicting the small bowel. Delivery via the orally ingestible delivery system as disclosed herein offers another route of administration, one that avoids physical manipulation of the region that has been damaged by IBD, and one that can be engineered to deposit the stem cells in the region(s) of the intestine that have need of stem cell treatment. In embodiments, the stem cells can be advantageously combined with media to enhance the viability or efficacy of the living organisms, or with other pharmaceutical or non-pharmaceutical agents that can act synergistically or cooperatively with the living organisms to enhance their viability or efficacy. Delivery of stem cells via the orally ingestible delivery system is compatible with multiple successive doses of the therapeutic agent, with the doses each engineered to reach the same or different anatomic regions. Other adaptations of the orally ingestible delivery systems disclosed herein can be envisioned by skilled artisans familiar with the therapeutic demands of IBD and similar disorders.

In embodiments, therapeutic agents are delivered rectally for conditions or disorders characterized by damage to the normal gastrointestinal flora, whose therapy involves populating the intestine (especially the colon) with so-called "beneficial bacteria," otherwise known as probiotic bacteria, living microorganisms that provide beneficial health effects by replenishing natural gastrointestinal flora. The orally ingestible delivery systems disclosed herein offer advantages for the delivery of probiotic bacteria to the human intestinal tract.

Probiotic bacteria can be transplanted from a healthy individual into a recipient suffering from a derangement of colonic microflora by a procedure known as stool transplant or fecal microbiota transplant (FMT). FMT is used to treat infections such as *Clostridium difficile* (*C. diff*) infection often caused by prolonged administration of antibiotics to treat another infection, where the original antibiotics also kill off the healthy bacteria in the gut, permitting overgrowth with *C. diff*. Refractory cases of *C. diff* infections can be treated with FMT, with the transplanted bacteria competing with and ultimately supplanting the *C. diff*. FMT has been used for treatment of other diseases, notably ulcerative colitis. While *C. diff* infections may be cured by a single FMT, other diseases may require multiple or chronic treatments. Preparations of colonic microflora as freeze-dried and other gastric-resistant oral formulations exist, but they are still vulnerable to attack and damage in the stomach. Typically, FMT requires introducing the donor's healthy and viable colonic microflora through an infusion of stool into the colon via colonoscopy or enema. An orally ingestible delivery system as disclosed herein offers an oral delivery route for probiotic bacteria such as would be otherwise delivered to a patient rectally, as in FMT. Allowing viable bacteria in therapeutically effective amounts to access their target areas in the large or small intestines via an oral route of intake can eliminate the need for the inconvenience and discomfort of rectal administration, particularly valuable in cases where repeated or chronic treatment is required, or in cases where delicate patient populations (for example, children, elderly, or medically tenuous patients) are involved.

Probiotic bacteria are widely touted as therapeutic agents in nutraceutical products for the supplementation of natural intestinal flora and the improvement of a person or animal's health or well-being. The degree to which a probiotic bacteria supplement affords benefit varies, depending on how they are delivered. Rectal administration is not employed for non-medical conditions, i.e., for uses intended to improve health or enhance well-being rather than treat major disease.

EXAMPLES

The following materials can be or were used in Examples 1-10 below.
  Xanthan gum, manufacturer Bob's Red Mill, source Amazon
  Yellow Organic Beeswax, manufacturer Mary Taylor, source Amazon
  White Organic Beeswax, manufacturer Mary Taylor, source Amazon
  Bio Case pancreatic enzyme formula, manufacturer Thomas Labs, source Amazon
  Gelatin capsule blanks size 00, manufacturer Herb Affair, source Amazon
  ¼" loose bicycle ball bearings, source Amazon
  Soy lecithin powder, manufacturer Will Powder, source Amazon
  Pure raw linseed oil, manufacturer Sunnyside, source Amazon
  Steel blue layout fluid, manufacturer Dykem, source Amazon
  Master Airbrush model G22, manufacturer Master Airbrush, source Amazon
  Sodium bicarbonate, source Sigma
  Span 20, source Sigma
  Poly(ethylene glycol) diglycydal ether, source Sigma
  Benzyltriethylammonium chloride, source Sigma
  Bovine gelatin, source Sigma

Example 1

Capsule blanks were prepared as follows.

Three ¼" steel ball bearings were placed inside a gelatin capsule blank (Gelatin capsule blanks size 00, manufacturer Herb Affair, source Amazon). To this was added five drops of blue layout fluid. The capsule was closed.

Coated capsules were prepared as follows.

Coating layer: Two beakers, B1 (hydrophobic phase) and B2 (hydrophilic phase) were prepared, as detailed below. B1 contained 6 grams of organic yellow beeswax. To this wax was added 0.1 grams of linseed oil by pipette. B1 is placed on a hotplate to a temperature 60-80° C. until melted. The wax melted and a stir bar was used on the hotplate (combination unit) to stir the linseed into the wax phase; the two phases were then miscible. To this mixture was added roughly 0.1 grams of surfactant (Span 20) by pipette. B2 contained the hydrophilic phase. The base of the hydrophilic phase was deionized water that had 10% sodium bicarbonate by mass diluted into it to the point of saturation. 6 grams of sodium bicarbonate/water solution was pipetted into a beaker. The measured sodium bicarbonate/water solution was placed on a hot plate to reach 60-80° C. With a stir bar rotating, the hydrophilic phase in B2 was added to the waxy B1 and allowed to mix on a 60-80° C. hotplate for one (1) minute until thoroughly mixed.

Coating process: The resulting coating solution was poured into the reservoir of an airbrush. A heat gun was used to keep the airbrush reservoir and nozzle above 60° C. Prepared capsules were partially wrapped with a rolled piece of paper to hold securely. The exposed half was sprayed by the airbrush to form half-coated capsules. The half-coated capsules were placed in a tray to dry for ten minutes. The half-coated capsules were then wrapped with a piece of paper so that the uncoated end was exposed. This uncoated end was sprayed by the airbrush and coating solution. Coated capsules prepared according to the methods of Example 1 are termed "Sample 1" hereinafter, and coated capsules prepared according to the methods of other Examples are designated with numbers corresponding to such Examples.

Example 2

Coated capsules were prepared according to the methods of Example 1, with the following modifications.

Coating layer: For this Example, B1 and B2 were prepared as Example 1, except that the surfactant was not added to B1. In B2, 0.01 g of xanthan gum was added and mixed at high shear for five (5) minutes. The solution of mixed sodium bicarbonate/water and xanthan gum was heated to 60-80° C. and added to the melted wax/linseed oil in B1 at 60-80° C. The combined solution was stirred for 1 minute at 60-80° C. before the coating process. Coated capsules prepared according to the methods of Example 2 are termed "Sample 2" hereinafter.

Example 3

Coated capsules were prepared according to the methods of Example 1, with the following modifications.

Coating layer: In B1 0.03 g poly(ethylene glycol) diglycidyl ether was added to the wax instead of linseed oil. The combination in B1 was heated to 60-80° C. on a hotplate and subsequently stirred for one minute. In B2, 0.1 g benzyltriethylammonium chloride was added instead of xanthan gum. The combination in B2 was mixed for five minutes and heated to 60-80° C. on a hotplate. B1 and B2 were combined and stirred for five minutes at 60-80° C. before the coating was applied to the capsules as described in Example 1. Coated capsules prepared according to the methods of Example 3 are termed "Sample 3" hereinafter.

Example 4

Coated capsules were prepared according to the methods of Example 2, with the following modifications.

Additive solutions: The following solutions were prepared, to be added to the coating layer as described below.

Preparation of Polyisobutylene Hexane Solution:

1 gram of polyisobutylene was cut into about 0.2 gram pieces, and the pieces were placed in a beaker. Into the beaker was added hexane of volume such that the solution was 1% by mass polyisobutylene. The solution was stirred on high shear until the polyisobutylene was dissolved.

Preparation of Polyisobutylene Toluene Solution:

1 gram of polyisobutylene was cut into about 0.2 gram pieces, and pieces were placed in a beaker. Into the beaker was added toluene of volume such that the solution was 1% by mass polyisobutylene. The solution was stirred on high shear until the polyisobutylene was dissolved.

Preparation of Polyisobutylene Benzene Solution:

1 gram of polyisobutylene was cut into about 0.2 gram pieces, and pieces were placed in a beaker. Into the beaker was added benzene of volume such that the solution was 1% by mass polyisobutylene. The solution was stirred on high shear until the polyisobutylene was dissolved.

Coating layer: In B1 6 grams of yellow beeswax was melted at 60-80° C. on a hot plate. 0.01-0.04 g of a solution of polyisobutylene hexane, polyisobutylene toluene, or polyisobutylene benzene was added to the melted beeswax by pipette. The combination was stirred for one minute at 60-80° C. In B2, to 3-6 g sodium bicarbonate/water was added 0.005-0.01 g xanthan gum. The combination was mixed at high shear for five minutes. B2 was then heated to 60-80° C. on a hotplate. B1 and B2 were combined and mixed for one minute at 60-80° C. before the coating process.

Combinations prepared in Example 4 are listed Table 1 below. Each combination followed the same preparation steps as discussed in Example 4 above except that the absolute amount was varied according to the test. The composition of the samples prepared according to the methods of Example 4 are listed below:

TABLE 1

| Sample | Polyisobutylene (hexane) grams | Sodium bicarbonate/ water solution (grams) |
| --- | --- | --- |
| 4a | 0.01 | 6 |
| 4b | 0.02 | 6 |
| 4c | 0.03 | 6 |
| 4d | 0.03 | 3 |

Example 5

B1 was prepared as Experiment 4. B2 was prepared as in Example 3 except that xanthan was replaced with gelatin powder at 0.01, 0.05, and 0.11 grams. Each combination in B2 was mixed at 60-80° C. for one minute until dissolved. B1 and B2 were combined as in Example 4, and the coating process described in Example 1 was carried out.

Combinations prepared in Example 5 are listed in Table 2 below. Each combination followed the same preparation steps as described above except that the absolute amount was varied according to the test. The composition of the samples prepared according to the methods of Example 5 are listed below:

TABLE 2

| Sample | Polyisobutylene (hexane) grams | Sodium bicarbonate/ water solution (grams) | Gelatin (grams) |
| --- | --- | --- | --- |
| 5a | 0.02 | 6 | 0.1 |
| 5b | 0.02 | 3 | 0.05 |

Example 6

For this Example, B1 was prepared as in Example 4 except that organic white wax was used instead of organic yellow wax, but in the same amount. 0.6 grams of Span 20 was added by pipette to the melted wax in B1. B2 was prepared with 2.7 grams of sodium bicarbonate/water and 0.3 grams gelatin. The combination in B2 was mixed for one minute at 60-80° C. until dissolved. B1 and B2 were combined as in Example 4 before the coating process. Coated capsules prepared according to the methods of Example 6 are termed "Sample 6" hereinafter.

Example 7

Coated capsules as prepared in Examples 2 through 6 were tested for their susceptibility to hydrochloric acid and to protease by creating experimental conditions analogous to those in the conditions in the human stomach. Two test solutions were prepared. A hydrochloric acid solution was prepared using a pH 2 hydrochloric acid stock solution. A protease solution was prepared by mixing 1.5 grams of Thomas Lab Bio Case pancreatic enzyme formula in 13.5 grams of water at high shear. In this and all the Examples below, the first solution is termed the "Acid Solution" and the second solution is termed the "Protease Solution." Each mixed solution was placed in a water bath at 37° C.

Coated capsules prepared as in Examples 2-6 were tested by dipping them in each of the test solutions. Sufficient test solution was used so that the coated capsule being tested was entirely immersed (about 20 ml per test). Observations were made while the coated capsules were immersed in the test solution. The first sign of breakage of the capsule was noted, indicated by the visibility of the colored fluid from within the capsule, and time between the initial immersion and this first sign of breakage is designated as the "survival time" for each immersion test. The results of these tests are set forth in Table 3 below.

TABLE 3

| Sample Number | Acid Solution survival time | Protease Solution survival time |
| --- | --- | --- |
| Control (blank capsule) | ~60 seconds | 5 minutes |
| Sample 2 | 64 minutes | (not tested) |
| Sample 3 | 70 minutes | 19 minutes |
| Sample 4a | <20 minutes | (not tested) |
| Sample 4b | 24 minutes, 30 minutes | (not tested) |
| Sample 4c | 35 minutes | 15 minutes |
| Sample 4d | ~7 hours | (not tested) |
| Sample 5a | 20 minutes | (not tested) |
| Sample 5b | (not tested) | (not tested) |

Example 8

Capsule blanks can be prepared as follows: Three ¼" steel ball bearings can be placed inside a capsule blank. To this can be added water-soluble orange seasoning, such as Sazon Goya. The capsule can then be closed.

Coated capsules can be prepared by preparing a coating layer and using it to coat the capsule.

Coating layer: A hydrophobic coating can be prepared using 6 grams of organic yellow beeswax. The beaker containing the beeswax can be placed on a hotplate to a temperature 60-80° C. until melted. When the wax melts, 0.1 grams of 1% polyisobutylene in hexane can be added by pipette and left to mix for one minute. Citric acid can be added to the beeswax phase and left to mix on a 60-80° C. hotplate for one (1) minute until thoroughly mixed.

Coating process: The resulting coating layer mixture as described above can be poured into the reservoir of an airbrush. A heat gun can be used to keep the airbrush reservoir and nozzle above 60° C. Capsules prepared as described above can be partially wrapped with a rolled piece of paper to hold securely. The exposed half can be sprayed by the airbrush to form half-coated capsules. The half-coated capsules can be placed in a tray to dry for ten minutes. The half-coated capsules can then be wrapped with a piece of paper so that the uncoated end is exposed. This uncoated end can be sprayed by the airbrush and coating solution with another layer and left to dry for at least ten minutes.

Gelatin overcoat: A gelatin overcoating can then be added on top as an optional sacrificial layer. This gelatin coating can be made by following these steps: first, a beaker of water can be heated on a hot plate to 80° C. while stirring. Palm oil glycerin is added to form a 0.1% solution of palm oil glycerin in deionized water. While the heated solution is being stirred vigorously, gelatin (bovine gelatin, source Sigma) can be added to form a 2% solution. The solution can be left to stir until the gelatin powder is dissolved. The final solution containing the gelatin and the glycerin is then added to the airbrush reservoir and sprayed in the same manner as described previously to form a uniform gelatin coating on top of the capsule structure. Thus formed, the coated capsule can be left to dry overnight.

Testing procedure: Three capsules can be made for testing as described above. The prepared coated capsules can be tested for their susceptibility to hydrochloric acid and to protease by creating experimental conditions analogous to those in the conditions in the human stomach. Two test solutions can be prepared as outlined in Experiment 7: (a) a hydrochloric acid solution can be prepared using a pH 2 hydrochloric acid stock solution (the Acid Solution); and (b) a protease solution can be prepared by mixing 1.5 grams of Thomas Lab Bio Case pancreatic enzyme formula in 13.5 grams of water at high shear (the Protease Solution). Each mixed solution can be placed in a water bath at 37° C. The coated capsules can be tested by dipping them in each of the test solutions and observing their results. Sufficient test solution should be used so that the coated capsule being tested can be entirely immersed (about 20 ml per test). Survival time, as described above can be measured. Possible results of these tests are set forth in Table 4 below.

TABLE 4

| Sample Number | Acid Solution survival time | Protease Solution survival time |
| --- | --- | --- |
| Control (blank capsule) | ~60 seconds | 4 minutes |
| Sample 8a | 184 minutes | 22 minutes |
| Sample 8b | 176 minutes | 18 minutes |
| Sample 8c | 188 minutes | 21 minutes |

Example 9

To prepare a wax sheet, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. 1.2 g of alginate fibers can be mixed in as well. While heated, the wax/fiber suspension may be poured directly onto a table-top or other flat surface. A wet film coating applicator with 200 um clearance can be carefully placed on top of the hot suspension and dragged across an area of the table until no material is left to spread. This layer can be left to dry for about 10 minutes. Once the layer is dried, a razor can be used to cut off the four ends of the sheet to make a rectangular shaped sheet, and the sheet can also be cut into 25 mm×32 mm rectangles. Each rectangle can be tested separately by placing it onto a sheet of pH paper and applying the Acid Solution or the Protease Solution to it, as was described in previous experiments. The pH paper can identify the change of pH that indicates the seepage of the Acid Solution through the rectangle, and the time for this seepage can be measured; if the Protease Solution seeps through, no pH change may be noted, but the paper will appear wet, which will allow time of seepage to be measured. As another experiment, each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in the Acid Solution and the Protease Solution as described in previous experiments.

Example 10

To prepare a wax sheet, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. A paste can be prepared including 0.6 g of starch, 0.6 g of calcium carbonate, and 1 g of Tween 80 surfactant. This paste can be mixed into the wax. While heated, the wax/fiber suspension can be poured directly onto a table-top or other flat surface. A wet film coating applicator with 200 um clearance can be carefully placed on top of the hot suspension and dragged across an area of the table until no material is left to spread. This layer can be left to dry for about 10 minutes.

Once the layer is dried, a razor can be used to cut off the four ends of the sheet to make a rectangular shaped sheet, and the sheet can also be cut into 25 mm×32 mm rectangles. Each rectangle can be tested separately by placing it onto a sheet of pH paper and applying the Acid Solution or the Protease Solution to it, as was described in previous experiments. The pH paper can identify the change of pH, or it can show wetness, either of which can indicate the seepage of the respective Solution through the rectangle, allowing the time for this seepage can be measured. As another experiment, each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in the Acid Solution and the Protease Solution as described in previous experiments.

Coated capsules can be prepared as in Examples 1-2 were tested by dipping them in each of the test solutions. Sufficient test solution can be used so that the coated capsule being tested is entirely immersed (about 20 ml per test). Capsule blanks can be prepared in the same manner as previously described in Example 8. Possible results of these tests are set forth in Table 5 below.

TABLE 5

| Sample Number | Acid Solution survival time | Protease Solution survival time |
| --- | --- | --- |
| Control (blank capsule) | ~60 seconds | 5 minutes |
| Sample 1a | 185 minutes | 18 minutes |
| Sample 1b | 177 minutes | 23 minutes |
| Sample 1c | 183 minutes | 19 minutes |

TABLE 5-continued

| Sample Number | Acid Solution survival time | Protease Solution survival time |
| --- | --- | --- |
| Sample 2a | 173 minutes | 15 minutes |
| Sample 2b | 168 minutes | 15 minutes |
| Sample 2c | 159 minutes | 16 minutes |

Materials for Examples 11-17: The following materials can be used in Examples 11-17 below:
  Gelatin capsules (size 000)
  Gelatin capsules (size 0)
  Gelatin sheets
  Soybean wax
  Ethanol
  Powdered bovine gelatin
  DI water
  Hexane
  Polyisobutylene
  Soy lecithin
  Cellulose fibers Example 11

A gelatin solution can be made by mixing 5 g of powdered gelatin into 13 g of water and allowing it to bloom/sit to absorb the water for 3-5 minutes. Then 7 g of ethanol can be added as a volatile component that minimizes amount of water used to prevent degradation of the gelatin capsule, and the solution can be mixed, covered, on stir plate around 50° C.-60° C. 6 g of $CaCO_3$ and 0.3 g of soy lecithin can be added and mixed in as well. While heated, the suspension can be poured into the reservoir of an airbrush sprayer, sprayed onto a gelatin capsule (size 0) as a relatively even coating, and left to dry for an hour.

To prepare a second coating, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. While heated, the wax solution can be poured into the reservoir of an airbrush sprayer, sprayed onto a gelatin capsule as a relatively even coating, and left to dry for an hour.

As a final coating, the coated gelatin capsule can be encapsulated in a larger gelatin capsule (size 000), to form a capsule having three layers: inner gelatin layer, middle wax layer, outer gelatin layer. Three of these three-layer capsules can be made for subsequent testing in the Acid Solution and the Protease Solution as described in previous experiments.

Example 12

A pre-formed gelatin sheet can be laid out on top of a substrate.

To prepare a wax coating, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. 1.2 g of $CaCO_3$ and 0.3 g of soy lecithin can be added and mixed in as well. While heated, the suspension may be poured into the reservoir of an airbrush sprayer, sprayed onto the gelatin sheet as a relatively even coating.

While the coating is still sticky, a final gelatin sheet can be place on top of the wax coating to form a three-layer sheet having an inner gelatin layer, a middle wax layer, an outer gelatin layer. Three of these sheets can be made for subsequent testing in the Acid Solution and the Protease Solution as described in previous experiments.

Example 13

A gelatin solution can be made by mixing 5 g of powdered gelatin into 20 g of water, and the solution can be mixed on a stir plate around 50° C.-60° C. 6 g of $CaCO_3$ can be added and mixed in as well. While heated, the suspension may be poured onto a tabletop, and a wet film coating applicator with 100 um clearance can be carefully placed on top of the hot suspension and dragged across an area of the table until no material is left to spread. This layer can be left to dry for about 10 minutes.

To prepare a second layer, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. 1.2 g of cellulose fibers and 0.3 g of soy lecithin can be mixed in as well. While heated, the wax/fiber suspension the suspension may be poured directly on top of one side of the previously made gelatin sheet. The wet film coating applicator with 200 um clearance can be carefully placed on top of the hot suspension and dragged across the gelatin sheet until no material is left to spread. This layer can be left to dry for about 10 minutes.

As a final layer, the same gelatin solution as described above can be made by mixing 5 g of powdered gelatin into 20 g of water, and the solution can be mixed, covered, on a stir plate around 50° C.-60° C. While heated, the gelatin solution can be poured directly on top of one side of the previously made wax sheet. The wet film coating applicator with 100 um clearance can be carefully placed on top of the hot solution and dragged across the wax sheet until no material is left to spread. This can be left to dry for an hour.

Once the layers are dried, a razor can be used to cut off the four ends of the sheets to make a rectangular shaped sheet, and the sheet can also be cut into 25 mm×32 mm rectangles. Each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in the Acid Solution and Protease Solution as described in previous experiments.

Example 14

A gelatin solution can be made by mixing 5 g of powdered gelatin into 20 g of water, and the solution can be mixed on a stir plate around 50° C.-60° C. 6 g of $CaCO_3$ can be added and mixed in as well. While heated, the suspension may be poured onto a tabletop, and a wet film coating applicator with 100 um clearance can be carefully placed on top of the hot suspension and dragged across an area of the table until no material is left to spread. This layer can be left to dry for about 10 minutes.

To prepare a second layer, a 1% solution of polyisobutylene in hexane can be prepared. 6 g of soybean wax can be melted and stirred on a hot plate around 50° C.-60° C., and 3 g of the 1% polyisobutylene solution can be added into the melted wax and left to stir for a few minutes until the hexane has evaporated. 1.2 g of cellulose fibers and 0.3 g of soy lecithin can be mixed in as well. While heated, the wax/fiber suspension the suspension may be poured directly on top of one side of the previously made gelatin sheet. The wet film coating applicator with 400 um clearance can be carefully placed on top of the hot suspension and dragged across the gelatin layer until no material is left to spread. This layer can be left to dry for about 10 minutes.

As a final layer, a similar gelatin solution as described above can be made by mixing 5 g of powdered gelatin into 20 g of water, and the solution can be mixed, covered, on a stir plate around 50° C.-60° C. While heated, the gelatin solution may be poured directly on top of one side of the previously made wax sheet. The wet film coating applicator with 100 um clearance can be carefully placed on top of the hot solution and dragged across the wax layer until no material is left to spread. This can be left to dry for an hour.

Once the layers are dried, a razor can be used to cut off the four ends of the sheets to make a rectangular shaped sheet, and the sheet can also be cut into 25 mm×32 mm rectangles. Each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in the Acid Solution and the Protease Solution as described in previous experiments.

Example 15

A gelatin sheet can be purchased and used as the initial coating and laid out on a substrate.

To prepare a second layer on top of the gelatin sheet, a 1% solution of polyisobutylene in hexane can be prepared. Separately, a suspension of $CaCO_3$ in water (~20%) can be made, and cellulose fibers can be added to this suspension and allowed to stir on a stir plate. This beaker can then be placed into the oven at around 120° C. to allow the water to evaporate out completely. This may coat the fibers. In yet another beaker, 6 g of soybean wax can be melted and stirred on a hot plate around 50° C.-60° C., and 3 g of the 1% polyisobutylene solution can be added into the melted wax and left to stir for a few minutes until the hexane has evaporated. 1.2 g of coated cellulose fibers and 0.3 g of soy lecithin can be mixed in as well. While heated, the wax/fiber suspension may be poured directly on top of the edge of the gelatin sheet. The wet film coating applicator with 200 um clearance can be carefully placed on top of the hot suspension and dragged across the gelatin sheet until no material is left to spread.

As a final layer, another gelatin sheet can be placed on top of a mildly heated wax layer.

Once everything has dried, a razor can be used to cut off the four ends of the sheets to make a rectangular shaped sheet with uniform thickness, and the sheet can also be cut into 25 mm×32 mm rectangles. Each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in the Acid Solution and the Protease Solution as described in previous experiments.

Example 16

A gelatin solution can be made by mixing 5 g of powdered gelatin into 20 g of water, and the solution can be mixed on a stir plate around 50° C.-60° C. 6 g of CaCO₃ and 0.3 g of soy lecithin can be added and mixed in as well. While heated, the suspension can be poured onto a tabletop, and a wet film coating applicator with 100 um clearance can be carefully placed on top of the hot suspension and dragged across an area of the table until no material is left to spread. This layer can be left to dry for about 10 minutes.

To prepare a second layer on top of the gelatin layer, a 1% solution of polyisobutylene in hexane can be prepared. Separately, 6 g of soybean wax can be melted and stirred on a hot plate around 50° C.-60° C., and 3 g of the 1% polyisobutylene solution can be added into the melted wax and left to stir for a few minutes until the hexane has evaporated. While heated, the wax suspension may be poured directly on top of the edge of the gelatin layer. The wet film coating applicator with 200 um clearance can be carefully placed on top of the hot suspension and dragged across the gelatin sheet until no material is left to spread. After ten minutes of drying, the microneedle roller can be carefully rolled on top of the wax layer to create micropores in the wax layer, being careful that the needles do not penetrate the gelatin layer.

As a final layer, another gelatin sheet can be made similarly as stated above by mixing 5 g of powdered gelatin into 20 g of water, and the solution can be mixed, covered, on a stir plate around 50° C.-60° C. While heated, the gelatin solution may be poured onto another blank tabletop substrate. The wet film coating applicator with 100 um clearance can be carefully placed on top of the hot suspension and dragged across the tabletop until no material is left to spread. This can be left to dry for about 10 minutes, and the previous gelatin/wax layer can be placed on top (wax side down).

A razor can then be used to cut off the four ends of the sheets to make a rectangular shaped sheet with uniform thickness, and the sheet can also be cut into 25 mm×32 mm rectangles. Each rectangle can be rolled into a cylinder, and the edges can be lightly melted with a nearby lighter to create a seam. The sides can also be folded over and lightly melted to allow the sides to close in the same manner. Three of these closed cylinders can be made for subsequent testing in stomach acid and duodenum juices as described in previous experiments.

Example 17

Coated capsules prepared according to Examples 11-16 can be tested using the following protocol:

Coated capsules could be prepared as in Examples 11-16 can tested by dipping them in each of the Acid Solution and Protease Solution. Sufficient amounts of test solution can be used so that the coated capsule being tested is entirely immersed (about 20 ml per test). Prophetic results of these tests are set forth in Table 6 below. Capsule blanks can be prepared in the same manner as described in Example 1, using three ¼" steel ball bearings and a water-soluble orange food coloring or seasoning, as described in previous Examples. The survival time can be determined as set forth in Example 6.

TABLE 6

| Sample Number | Acid Solution survival time | Protease Solution survival time |
| --- | --- | --- |
| Control (blank capsule) | ~60 seconds | 5 minutes |
| Sample 1a | 181 minutes | 19 minutes |
| Sample 1b | 179 minutes | 19 minutes |

TABLE 6-continued

| Sample Number | Acid Solution survival time | Protease Solution survival time |
| --- | --- | --- |
| Sample 1c | 183 minutes | 23 minutes |
| Sample 2a | 167 minutes | 18 minutes |
| Sample 2b | 166 minutes | 15 minutes |
| Sample 2c | 158 minutes | 14 minutes |
| Sample 3a | 172 minutes | 19 minutes |
| Sample 3b | 177 minutes | 16 minutes |
| Sample 3c | 173 minutes | 17 minutes |
| Sample 4a | 183 minutes | 18 minutes |
| Sample 4b | 183 minutes | 20 minutes |
| Sample 4c | 186 minutes | 20 minutes |
| Sample 5a | 175 minutes | 22 minutes |
| Sample 5b | 177 minutes | 21 minutes |
| Sample 5c | 185 minutes | 23 minutes |
| Sample 6a | 184 minutes | 18 minutes |
| Sample 6b | 184 minutes | 20 minutes |
| Sample 6c | 186 minutes | 20 minutes |

Materials for Examples 18-25: The following materials can be used in Examples 18-25 below.

Bovine gelatin, source Sigma

Yellow Organic Beeswax, manufacturer Mary Taylor, source Amazon

Precipitated calcium carbonate powder, source Amazon

Span 80, source Sigma

Sodium stearate, source Sigma

Pectin, source Sigma

Hexane, source Sigma

Polyisobutylene, source Sigma

Cellulose fiber, source Sigma

Vitamin A, source Sigma

Vitamin D, source Sigma

Vitamin E, source Sigma

Vitamin K, source Sigma

Example 18

For this Example, an aqueous phase is prepared by dissolving 2 grams of bovine gelatin in 6 grams of heated water to create a 25% bovine gelatin solution by weight. If cooled to room temperature, the gelatin solidifies into a gel-like matrix. Prior to the cooling period, about 0.8 grams of precipitated calcium carbonate (PCC) is added with stirring. It is observed that the PCC does not dissolve into the gelatin water. Instead, the stirring distributes the PCC crystals within the cooling gelatin solution. As the gelatin cools the PCC is suspended uniformly as little crystals. Separately, a hydrophobic phase is prepared by melting at about 60 degrees Celsius grams of unrefined yellow beeswax, and adding 1% or less by wt of Span 80 into the melted unrefined yellow beeswax, mixing the two together well with constant heat applied. Then the aqueous phase containing the PCC crystals and the hydrophobic phase are mixed vigorously in a ratio 1:5 wax:aqueous, thereby blending the two phases while both are still liquid. The mixture is poured into molds and allowed to cool. The final product looks uniform and is compressible with a springy property so that it returns to its original shape if not much force is applied.

Example 19

In this Example, we modify Example 18 by adding polyisobutylene (PIB) into the hydrophobic phase prepared in Example 18, in order to bolster the mechanical property of the final product formulation. To prepare the PIB additive as a dilute solution, we dissolve 1% PIB by weight into hexane solvent at room temperature, using a stirring motion. As described in Example 18, the hydrophobic phase is prepared by melting the unrefined yellow beeswax and adding Span 80. The aqueous phase is prepared as in Example 18, yielding a solution of 25% by wt bovine gelatin dissolved in warm water, to which is added 10% by wt PCC. Prior to mixing these hydrophobic and aqueous phases, we add 3% by wt (of the hydrophobic phase) of PIB solution directly to the hydrophobic phase at 60° C., with brief stirring. The hexane evaporates, leaving behind the PIB entrained within the hydrophobic phase. With the dissolved PIB thus added to the hydrophobic phase, we combine the hydrophobic and the aqueous phases to yield the final product.

Example 20

In this Example, we modify Example 18 or 19 by adding a small amount (1-3%) pectin to the aqueous phase. Pectin is a polysaccharide that helps the process of gelling in a calcium environment by being attracted to the calcium ion. In this Example, a 1-3% by wt pectin solution is added into the 8 grams of gelatin/water that forms the aqueous phase in Examples 18 and 19. At the same time or shortly thereafter, we add the PCC into the aqueous phase and stir to disperse the PCC and pectin throughout the aqueous phase. The pectin is attracted to the calcium ions in PCC and helps to present a hydrophilic surface layer around the PCC. This helps disperse the PCC throughout the aqueous phase during the final mixing of the aqueous and hydrophobic phases.

Example 21

In this Example, we modify Example 18 or 19 or 20 by adding cellulose fiber to the unrefined yellow beeswax in the hydrophobic phase. 1-2 grams of cellulose fiber is added to the hydrophobic phase prepared in accordance with Example 18 (melted unrefined yellow beeswax plus 1% Span 80 by weight) to yield a total mass of 3 grams, stirring in the cellulose at 60° C. After forming the hydrophobic phase with its cellulose additive, we combined this phase with the aqueous phase as described in the previous Examples and stir before continuing with further formulation.

Example 22

This Example provides a modification of Examples 18 or 19 or 20 or 21, by adding one or more fat-soluble (water-insoluble) vitamins to the hydrophobic phase of Examples 18, 19, 20, or 21. Between 0.5-1 grams total of the combinations of vitamins A, D, E, and K are added to the 3 grams net wt of the hydrophobic phase of Examples 18, 19, 20, or 21 at 60° C. and stirring in the vitamin(s), for example in powdered form. After adding the fat-soluble vitamin to the hydrophobic phase, it is combined with the aqueous phase as describe in the previous examples.

Example 23

We prepared a stock solution of precipitated calcium carbonate (PCC) by combining 109 grams of DI water, 10 grams PCC, and 0.3 grams of sodium stearate (stearic acid) at a temperature above 60° C. and stirred for several minutes. In a second beaker we melted 4 grams of unrefined yellow beeswax at 60° C. In a third beaker we prepared a stock solution of melted gelatin by combining 12 grams of DI water and 3 grams of bovine gelatin at 60 Celsius and stirring. In the hydrophobic phase beaker we added 2 grams of the PCC water solution to the 4 grams of melted unrefined yellow beeswax. We poured 8 grams of the gelatin stock solution into the hydrophobic phase beaker and stirred at 60° C. We poured the resulting product into molds and allowed the mixture to cool. The result was that the aqueous and hydrophobic phases completed separated.

Example 24

We combined 7 grams of the stock gelatin solution prepared in accordance with Example 23 with 1.80 grams of melted unrefined yellow beeswax and 0.2 grams of the PCC stock solution (prepared in accordance with Example 23) at 60° C. and stirred. To this we added about 2 ml of Span 80 surfactant and continued to mix at 60° C. and high shear stirring. We poured this product into molds and allowed it to set. The result was a product with a preponderance of the aqueous phase, and with a low amount of mechanical rigidity.

Example 25

In one beaker we combined 13.86 grams of DI water and 3.26 grams of bovine gelatin and stirred at 60° C., to form the aqueous phase. In a second beaker, we melted 3.9 grams of unrefined yellow beeswax at 60° C. and added about 2 ml of Span 80 surfactant to form the hydrophobic phase. Into the first beaker with the gelatin and water we added 1.45 grams of PCC in its powder form and stirred to mix it into the solution. We added the hydrophobic phase directly to the aqueous phase at 60° C. and stirred to mix. We poured this product into molds and allowed it to cool. The result was a uniform material with gummy and springy consistency.

While this invention has been particularly shown and described with references to preferred embodiments thereof, it will be understood by those skilled in the art that various changes in form and details may be made therein without departing from the scope of the invention encompassed by the appended claims.

While specific embodiments of the subject invention have been disclosed herein, the above specification is illustrative and not restrictive. While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. A method of delivering a therapeutic agent into an intestine of a mammal, comprising:
orally administering an orally ingestible delivery system (OIDS) to the mammal, wherein the OIDS comprises a therapeutic agent and a differentially permeable capsule system, wherein the therapeutic agent is contained within a therapeutic agent compartment;

wherein the differentially permeable capsule system comprises an acid-resistant protease-digestible membrane and a gas-producing substance;

wherein the acid-resistant protease-digestible membrane comprises an inner protease-digestible layer and an outer acid-resistant layer, wherein the inner protease-digestible layer surrounds the therapeutic agent compartment;

wherein the outer acid-resistant layer is perforated by a system of pores providing fluid communication between the external surface of the acid-resistant protease-digestible membrane and the inner protease-digestible layer, and wherein the gas-producing substance is contained within the system of pores;

wherein the OIDS passes into the stomach of the mammal after the oral administration, and the gas-producing substance reacts with stomach acid to form a dispersible acid barrier, wherein the dispersible acid barrier is a gas and is formed within the pores and on the exterior surface of the outer acid-resistant layer, and wherein the dispersible acid barrier inhibits contact between the acid-resistant protease-digestible membrane and the gastric juice of the stomach; and wherein the gas-producing substance is a carbonate and wherein the gas is carbon dioxide;

and wherein the OIDS comprising the dispersible acid barrier passes into the intestine, wherein the dispersible acid barrier is dispersed by interaction of the carbon dioxide with bicarbonate in the intestine, and the intestinal fluids penetrate the acid-resistant protease-digestible membrane following the dispersal of the dispersible acid barrier to release the therapeutic agent from the therapeutic agent compartment;

thereby delivering the therapeutic agent to the intestine.

2. The method of claim 1, wherein the intestinal fluids impair integrity of the inner protease-digestible layer, thereby facilitating release of the therapeutic agent from the therapeutic agent compartment.

3. The method of claim 1, wherein the therapeutic agent is a protein or a peptide.

4. The method of claim 1, wherein the therapeutic agent is a living organism.

5. The method of claim 1, wherein the carbonate is selected from the group consisting of calcium carbonate, sodium bicarbonate, potassium bicarbonate, and magnesium carbonate.

6. The method of claim 1, the method further comprising orally administering an acid to the patient before, during or after oral administration of the OIDS.

7. The method of claim 1, wherein the inner protease-digestible layer comprises gelatin.

8. The method of claim 1, wherein the carbonate is solid bicarbonate.

9. The method of claim 1, wherein the intestine is the small intestine.

10. The method of claim 9, wherein the bicarbonate is a component of duodenal fluid.

11. The method of claim 1, wherein the therapeutic agent is a prebiotic.

12. The method of claim 1, wherein the therapeutic agent is a probiotic.

13. The method of claim 1, wherein therapeutic agent is a small molecule.

14. The method of claim 1, wherein the system of pores is an interconnected system of pores.

15. The method of claim 1, wherein the outer acid-resistant layer comprises a wax.

16. The method of claim 15, wherein the wax is selected from the group consisting of beeswax, soybean wax, and carnauba wax.

* * * * *

UNITED STATES PATENT AND TRADEMARK OFFICE
CERTIFICATE OF CORRECTION

| | | |
|---|---|---|
| PATENT NO. | : 11,918,694 B2 | |
| APPLICATION NO. | : 17/075030 | |
| DATED | : March 5, 2024 | |
| INVENTOR(S) | : David S. Soane, Allison H. Greene and Alexander V. Soane | |

It is certified that error appears in the above-identified patent and that said Letters Patent is hereby corrected as shown below:

In the Claims

Column 106, Claim 13, Line 29: insert --the-- after "wherein"

Signed and Sealed this
Twenty-third Day of April, 2024

Katherine Kelly Vidal
*Director of the United States Patent and Trademark Office*